(12) United States Patent
Harris et al.

(10) Patent No.: US 11,192,929 B2
(45) Date of Patent: Dec. 7, 2021

(54) SITE-SPECIFIC DNA BASE EDITING USING MODIFIED APOBEC ENZYMES

(71) Applicant: Regents of the University of Minnesota, Minneapolis, MN (US)

(72) Inventors: Reuben S. Harris, St. Paul, MN (US); Hideki Aihara, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 85 days.

(21) Appl. No.: 15/836,598

(22) Filed: Dec. 8, 2017

(65) Prior Publication Data

US 2018/0170984 A1 Jun. 21, 2018

Related U.S. Application Data

(60) Provisional application No. 62/431,703, filed on Dec. 8, 2016.

(51) Int. Cl.
| | | |
|---|---|---|
| *C12N 15/00* | (2006.01) | |
| *C07K 14/47* | (2006.01) | |
| *C12N 9/22* | (2006.01) | |
| *C12N 15/10* | (2006.01) | |

(52) U.S. Cl.
CPC ............ *C07K 14/4703* (2013.01); *C12N 9/22* (2013.01); *C12N 15/102* (2013.01); *C12N 15/1082* (2013.01); *C07K 2319/80* (2013.01); *C07K 2319/85* (2013.01); *C12N 2310/20* (2017.05); *C12Y 302/02027* (2013.01); *C12Y 305/04005* (2013.01)

(58) Field of Classification Search
CPC ............ C07K 14/4703; C07K 2319/80; C07K 2319/85; C12N 9/22; C12N 15/102; C12N 15/1082; C12N 2310/20; C12Y 302/02027; C12Y 305/04005
See application file for complete search history.

(56) References Cited

U.S. PATENT DOCUMENTS

| | | |
|---|---|---|
| 2007/0033666 A1 | 2/2007 | Harris et al. |
| 2009/0269831 A1 | 10/2009 | Harris et al. |
| 2016/0304846 A1 | 10/2016 | Liu et al. |
| 2017/0121693 A1* | 5/2017 | Liu .......................... A61P 35/00 |
| 2018/0170984 A1 | 6/2018 | Harris et al. |
| 2019/0017055 A1 | 1/2019 | Harris et al. |
| 2020/0131496 A1 | 4/2020 | Harris et al. |

FOREIGN PATENT DOCUMENTS

| | | | |
|---|---|---|---|
| WO | WO 2004/067736 | 8/2004 | |
| WO | WO-2017070632 A2 * | 4/2017 | ............... A61P 19/02 |

OTHER PUBLICATIONS

Komor et al in "Programmable editing of a target base in genomic DNA without double-stranded DNA cleavage." (Nature vol. 533, pp. 420-424, published online Apr. 20, 2016). (Year: 2016).*

Supplemental Material for Komor et al in "Programmable editing of a target base in genomic DNA without double-stranded DNA cleavage." (Nature vol. 533, pp. 420-424, published online Apr. 20, 2016). (Year: 2016).*
Liu & Komor Ha Kim Score result for WO 2017070632. (Year: 2016).*
Adams et al., "PHENIX: a comprehensive Python-based system for macromolecular structure solution," Acta. Crystallogr. D. Biol. Crystallogr., 66(Pt 2):213-221, Feb. 2010.
Almog et al., "Three-dimensional structure of the R115E mutant of T4-bacteriophage 2'-deoxycytidylate deaminase," Biochemistry, 43(43): 13715-13723, Nov. 2004.
Boch et al., "Breaking the code of DNA binding specificity of TAL-type III effectors," Science, 326(5959):1509-1512, Dec. 2009.
Bogdanove et al., "TAL effectors: finding plant genes for disease and defense," Curr. Opin. Plant Biol., 13(4):394-401, Aug. 2010.
Bohn et al., "Crystal structure of the DNA cytosine deaminase APOBEC3F: the catalytically active and HIV-1 Vif-binding domain," Structure, 21(6): 1042-1050, Jun. 2013.
Bohn et al., "The ssDNA Mutator APOBEC3A Is Regulated by Cooperative Dimerization," Structure, 23(5):903-911, May 2015.
Bulliard et al., "Structure-function analyses point to a polynucleotide-accommodating groove essential for APOBEC3A restriction activities," J. Virol., 85(4): 1765-1776, Feb. 2011.
Burns et al., "APOBEC3B is an enzymatic source of mutation in breast cancer," Nature, 494(7437):366-370, Feb. 2013.
Burns et al., "Evidence for APOBEC3B mutagenesis in multiple human cancers," Nat. Genet., 45(9):977-983, Sep. 2013.
Byeon et al., "NMR structure of human restriction factor APOBEC3A reveals substrate binding and enzyme specificity," Nat. Commun., 4:1890, 2013.
Byeon et al., "Nuclear Magnetic Resonance Structure of the APOBEC3B Catalytic Domain: Structural Basis for Substrate Binding and DNA Deaminase Activity," Biochemistry, 55(21):2944-2959, May 2016.
Carpenter et al., "Determinants of sequence-specificity within human AID and APOBEC3Gm," DNA Repair (Amst), 9(5):579-587, May 2010.
Carpenter et al., "Methylcytosine and normal cytosine deamination by the foreign DNA restriction enzyme APOBEC3A," J. Biol. Chem., 287(41):34801-34808, Oct. 2012.
Caval et al., "A prevalent cancer susceptibility APOBEC3A hybrid allele bearing APOBEC3B 3'UTR enhances chromosomal DNA damage," Nat. Commun., 5:5129, Oct. 2014.
Caval et al., "Molecular basis of the attenuated phenotype of human APOBEC3B DNA mutator enzyme," Nucleic. Acids. Res., 43(19):9340-9349, Oct. 2015.
Cescon et al., "APOBEC3B expression in breast cancer reflects cellular proliferation, while a deletion polymorphism is associated with immune activation," Proc. Natl. Acad. Sci. USA., 112(9):2841-2846, Mar. 2015.
Chan et al., "An APOBEC3A hypermutation signature is distinguishable from the signature of background mutagenesis by APOBEC3B in human cancers," Nat. Genet., 47(9): 1067-1072, Sep. 2015.
Chen et al., "APOBEC3A is a potent inhibitor of adeno-associated virus and retrotransposons," Curr. Biol., 16(5):480-485, Mar. 2006.

(Continued)

*Primary Examiner* — Catherine S Hibbert
(74) *Attorney, Agent, or Firm* — Fish & Richardson P.C.

(57) ABSTRACT

Materials and methods for using modified Cas9-APOBEC fusion polypeptides for targeted modification of specific DNA sequences are provided herein.

16 Claims, 17 Drawing Sheets

Specification includes a Sequence Listing.

(56) References Cited

OTHER PUBLICATIONS

Chen et al., "Fusion protein linkers: property, design and functionality," Adv. Drug Deliv. Rev., 65(10): 1357-1369, Oct. 2013.
Chen et al., "Structure of the DNA deaminase domain of the HIV-1 restriction factor APOBEC3G," Nature, 452(7183): 116-119, Mar. 2008.
Cho et al., "Targeted genome engineering in human cells with the Cas9 RNA-guided endonuclease," Nat. Biotechnol., 31(3):230-232, Mar. 2013.
Cong et al., "Multiplex genome engineering using CRISPR/Cas systems," Science, 339(6121):819-823, Jan. 2013.
Conticello, "The AID/APOBEC family of nucleic acid mutators," Genome. Biol., 9(6):229, Oct. 2008.
Crooks et al., "WebLogo: a sequence logo generator," Genome. Res., 14(6):1188-1190, Jun. 2004.
Deltcheva et al., "CRISPR RNA maturation by trans-encoded small RNA and host factor RNase III," Nature, 471(7340):602-607, Mar. 2011.
Demorest et al., "Phosphorylation directly regulates the intrinsic DNA cytidine deaminase activity of activation-induced deaminase and APOBEC3G protein," J. Biol. Chem., 286(30):26568-26575, Jul. 2011.
Di Noia and Neuberger, "Altering the pathway of immunoglobulin hypermutation by inhibiting uracil-DNA glycosylase," Nature, 419(6902):43-48, Sep. 2002.
Di Noia and Neuberger, "Molecular mechanisms of antibody somatic hypermutation," Annu. Rev. Biochem., 76:1-22, Jul. 2007.
DiCarlo et al., "Genome engineering in *Saccharomyces cerevisiae* using CRISPR-Cas systems," Nucleic. Acids. Res., 41(7):4336-43, Apr. 2013.
Dong et al., "The crystal structure of Cpf1 in complex with CRISPR RNA," Nature, 532(7600):522-526, Apr. 2016.
Emsley and Cowtan, "Coot: model-building tools for molecular graphics," Acta. Crystallogr. D. Biol. Crystallogr., 60(Pt 12 Pt 1):2126-2132, Dec. 2004.
Ferretti et al., "Complete genome sequence of an M1 strain of *Streptococcus pyogenes*," Proc. Natl. Acad. Sci. USA., 98(8):4658-4663, Apr. 2001.
Fossat and Tam, "Re-editing the paradigm of Cytidine (C) to Uridine (U) RNA editing," RNA Biol 11(10): 1233-1237, Oct. 2014.
Fu et al., "DNA cytosine and methylcytosine deamination by APOBEC3B: enhancing methylcytosine deamination by engineering APOBEC3B," Biochem. J., 471(1):25-35, Oct. 2015.
Gaborek, "Conformational free-energy landscapes for a peptide in saline environments," Biophys. J., 103(12):2513-2520, Dec. 2012.
Genbank Accession No. NC_015683.1, "Corynebacterium ulcerans BR-AD22, complete genome," Jul. 30, 2015, 2 pages.
Genbank Accession No. NC_016782.1, "Corynebacterium diphtheriae 241, complete genome," Aug. 13, 2015, 2 pages.
Genbank Accession No. NC_016786.1, "Corynebacterium diphtheriae HC01, complete genome," Aug. 13, 2015, 2 pages.
Genbank Accession No. NC_017053.1, "*Streptococcus pyogenes* MGAS1882, complete genome," Aug. 13, 2015, 2 pages.
Genbank Accession No. NC_017317.1, "Corynebacterium ulcerans 809, complete genome," Aug. 13, 2015, pp. 2.
Genbank Accession No. NC_017861.1, "Prevotella intermedia 17 chromosome II, complete sequence," Aug. 13, 2015, 2 pages.
Genbank Accession No. NC_018010.1, "Belliella baltica DSM 15883, complete genome," Aug. 18, 2015, 2 pages.
Genbank Accession No. NC_018721.1, "Psychroflexus torquis ATCC 700755, complete genome," Aug. 14, 2015, 2 pages.
Genbank Accession No. NC_021284.1, "Spiroplasma syrphidicola EA-1, complete genome," Aug. 14, 2015, 2 pages.
Genbank Accession No. NC_021314.1, "*Streptococcus iniae* SF1, complete genome," Dec. 18, 2014, 1 page.
Genbank Accession No. NC_021846.1, "Spiroplasma taiwanense CT-1, complete genome," Aug. 22, 2015, 2 pages.

Genbank Accession No. NM_001644, "*Homo sapiens* apolipoprotein B mRNA editing enzyme catalytic subunit 1 (APOBEC1), transcript variant 1, mRNA," Oct. 8, 2016, 3 pages.
Genbank Accession No. NM_004900, "*Homo sapiens* apolipoprotein B mRNA editing enzyme catalytic subunit 3B (APOBEC3B), transcript variant 1, mRNA," Oct. 7, 2016, 3 pages.
Genbank Accession No. NM_014508, "*Homo sapiens* apolipoprotein B mRNA editing enzyme catalytic subunit 3C (APOBEC3C), mRNA," Sep. 1, 2016, 3 pages.
Genbank Accession No. NM_020661, "*Homo sapiens* activation induced cytidine deaminase (AICDA), transcript variant 1, mRNA," Sep. 5, 2016, 4 pages.
Genbank Accession No. NM_021822, "*Homo sapiens* apolipoprotein B mRNA editing enzyme catalytic subunit 3G (APOBEC3G), transcript variant 1, mRNA," Oct. 7, 2016, 4 pages.
Genbank Accession No. NM_145298, "*Homo sapiens* apolipoprotein B mRNA editing enzyme catalytic subunit 3F (APOBEC3F), transcript variant 1, mRNA," Sep. 1, 2016, 5 pages.
Genbank Accession No. NM_145699, "*Homo sapiens* apolipoprotein B mRNA editing enzyme catalytic subunit 3A (APOBEC3A), transcript variant 1, mRNA," Oct. 7, 2016, 4 pages.
Genbank Accession No. NM_152426, "*Homo sapiens* apolipoprotein B mRNA editing enzyme catalytic subunit 3D (APOBEC3D), mRNA," Sep. 1, 2016, 4 pages.
Genbank Accession No. NM_181773, "*Homo sapiens* apolipoprotein B mRNA editing enzyme catalytic subunit 3H (APOBEC3H), transcript variant SV-183, mRNA," Sep. 1, 2016, 3 pages.
Genbank Accession No. NP_472073.1, "hypothetical protein lin2744 [Listeria innocua Clip11262]," Dec. 17, 2014; 2 pages.
Genbank Accession No. YP_002342100.1, "hypothetical protein NMA0631 [Neisseria meningitidis Z2491]," Dec. 16, 2014, 2 pages.
Genbank Accession No. YP_002344900.1, "CRISPR-associated protein [*Campylobacter jejuni* subsp. *jejuni* NCTC 11168 = ATCC 700819]," Aug. 3, 2016, 2 pages.
Genbank Accession No. YP_820832.1, "CRISPR-system-like protein [*Streptococcus thermophilus* LMD-9]," Dec. 16, 2014, 2 pages.
Guilinger et al., "Fusion of catalyticaily inactive Cas9 to FokI nuclease improves the specificity of genome modification," Nat. Biotechnol., 32(6):577-582, Jun. 2014.
Harjes et al., "Impact of H216 on the DNA binding and catalytic activities of the HIV restriction factor APOBEC3G," J. Virol., 87(12):7008-7014, Jun. 2013.
Harris and Dudley, "APOBECS and Virus restriction," Virology, 479-480:131-145, May 2015.
Harris et al., "DNA deamination mediates innate immunity to retroviral infection," Cell, 113(6):803-809, Jun. 2003.
Helleday et al., "Mechanisms underlying mutational signatures in human cancers," Nat. Rev. Genet, 15(9):585-598, Sep. 2014.
Holden et al., "Crystal structure of the anti-viral APOBEC3G catalytic domain and functional implications," Nature, 456(7218):121-124, Nov. 2008.
Holtz et al., "APOBEC3G cytosine deamination hotspots are defined by both sequence context and single-stranded DNA secondary structure," Nucleic. Acids. Res., 41(12):6139-6148, Jul. 2013.
Hwang et al., "Efficient genome editing in zebrafish using a CRISPR-Cas system," Nat. Biotechnol., 31(3):227-229, Mar. 2013.
Ireton et al., "The 1.14 A crystal structure of yeast cytosine deaminase: evolution of nucleotide salvage enzymes and implications for genetic chemotherapy," Structure, 11(8):961-972, Aug. 2003.
Jiang et al., "RNA-guided editing of bacterial genomes using CRISPR-Cas systems," Nat. Biotechnol., 31(3):233-239, Mar. 2013.
Jinek et al., "A programmable dual-RNA-guided DNA endonuclease in adaptive bacterial immunity," Science, 337(6096):816-821, Aug. 2012.
Kabsch, "XDS," Acta. Crystallogr. D. Biol. Crystallogr., 66(Pt 2): 125-132, Feb. 2010.
Kim et al., "Human APOBEC3 induced mutation of human immunodeficiency virus type-1 contributes to adaptation and evolution in natural infection," PLoS Pathog., 10(7):e1004281, Jul. 2014.

(56) References Cited

OTHER PUBLICATIONS

Ko et al., "Crystal structure of yeast cytosine deaminase. Insights into enzyme mechanism and evolution," J. Biol. Chem., 278(21): 19111-19117, May 2003.
Kohli et al., "Local sequence targeting in the AID/APOBEC family differentially impacts retroviral restriction and antibody diversification," J. Biol. Chem., 285(52):40956-40964, Dec. 2010.
Koito and Ikeda, "Intrinsic immunity against retrotransposons by APOBEC cytidine deaminases," Front. Microbiol., 4:28, Feb. 2013.
Komor et al., "Programmable editing of a target base in genomic DNA without double-stranded DNA cleavage," Nature, 533(7603):420-424, May 2016.
Koning et al., "Defining APOBEC3 expression patterns in human tissues and hematopoietic cell subsets," J. Virol., 83(18):9474-9485, Sep. 2009.
Law et al., "The DNA cytosine deaminase APOBEC3B promotes tamoxifen resistance in ER-positive breast cancer," Sci. Adv., 2(10):e1601737, Oct. 2016.
Li et al., "First-in-class small molecule inhibitors of the single-strand DNA cytosine deaminase APOBEC3G," ACS. Chem. Biol., 7(3):506-517, Mar. 2012.
Logue et al., "A DNA sequence recognition loop on APOBEC3A controls substrate specificity," PLoS One., 9(5):e97062, May 2014.
Makarova et al., "Evolution and classification of the CRISPR-Cas systems," Nat. Rev. Microbiol., 9(6):467-477, Jun. 2011.
Mali et al., "CAS9 transcriptional activators for target specificity screening and paired nickases for cooperative genome engineering," Nat. Biotechnol., 31(9):833-838, Sep. 2013.
Mali et al., "RNA-guided human genome engineering via Cas9," Science, 339(6121):823-826, Feb. 2013.
Malim and Bieniasz, "HIV Restriction Factors and Mechanisms of Evasion," Cold Spring Harb. Perspect. Med., 2(5):a006940, May 2012.
Matthews et al., "Structures of human ADAR2 bound to dsRNA reveal base-flipping mechanism and basis for site selectivity," Nat. Struct. Mol. Biol., 23(5):426-433, May 2016.
McCoy et al., "Phaser crystallographic software," J. Appl. Crystallogr., 40(Pt 4):658-674, Aug. 2007.
Mitra et al., "Structural determinants of human APOBEC3A enzymatic and nucleic acid binding properties," Nucleic. Acids. Res., 42(2): 1095-1110, Jan. 2014.
Mol et al., "Crystal structure of human uracil-DNA glycosylase in complex with a protein inhibitor: protein mimicry of DNA," Cell, 82(5):701-708, Sep. 1995.
Narvaiza et al., "Deaminase-independent inhibition of parvoviruses by the APOBEC3A cytidine deaminase," PLoS. Pathog., 5(5):e1000439, May 2009.
Nik-Zainal et al., "Association of a germline copy number polymorphism of APOBEC3A and APOBEC3B with burden of putative APOBEC-dependent mutations in breast cancer," Nat. Genet. 46(5):487-491, May 2014.
Nik-Zainal et al., "Landscape of somatic mutations in 560 breast cancer whole-genome sequences," Nature, 534(7605):47-54, Jun. 2016.
Pham et al., "A biochemical analysis linking APOBEC3A to disparate HIV-1 restriction and skin cancer," J. Biol. Chem., 288(41):29294-29304, Oct. 2013.
Porteus and Baltimore, "Chimeric nucleases stimulate gene targeting in human cells," Science, 300(5620):763, May 2003.
Porteus, "Plant biotechnology: Zinc fingers on target," Nature, 459(7245):337-338, May 2009.
Qi et al., "Repurposing CRISPR as an RNA-guided platform for sequence-specific control of gene expression," Cell, 152(5): 1173-83, Feb. 2013.
Rathore et al., "The local dinucleotide preference of APOBEC3G can be altered from 5'-CC to 5'-TC by a single amino acid substitution," J. Mol. Biol., 425(22):4442-4454, Nov. 2013.
Rausch et al., "Dissecting APOBEC3G substrate specificity by nucleoside analog interference," J. Biol. Chem., 284(11):7047-7058, Mar. 2009.
Refsland et al., "Quantitative profiling of the full APOBEC3 mRNA repertoire in lymphocytes and tissues: implications for HIV-1 restriction," Nucleic. Acids. Res., 38(13):4274-4284, Jul. 2010.
Robbiani and Nussenzweig, "Chromosome translocation, B cell lymphoma, and activation-induced cytidine deaminase," Annu. Rev. Pathol., 8:79-103, Jan. 2013.
Roberts and Gordenin, "Hypermutation in human cancer genomes: footprints and mechanisms," Nat. Rev. Cancer., 14(12):786-800, Dec. 2014.
Roberts et al., "An APOBEC cytidine deaminase mutagenesis pattern is widespread in human cancers," Nat. Genet., 45(9):970-976, Sep. 2013.
Sheldrick, "Experimental phasing with SHELXC/D/E: combining chain tracing with density modification," Acta. Crystallogr. D. Biol. Crystallogr., 66(Pt 4):479-485, Apr. 2010.
Shi et al., "Crystal Structure of the DNA Deaminase APOBEC3B Catalytic Domain," J. Biol. Chem., 290(47):28120-28130, Nov. 2015.
Shirakawa et al., "Phosphorylation of APOBEC3G by protein kinase A regulates its interaction with HIV-1 Vif," Nat. Struct. Mol. Biol., 15(11): 1184-1191, Nov. 2008.
Sieuwerts et al., "Elevated APOBEC3B correlates with poor outcomes for estrogen-receptor-positive breast cancers," Horm. Cancer, 5(6):405-413, Dec. 2014.
Simon et al., "Intrinsic host restrictions to HIV-1 and mechanisms of viral escape," Nat. Immunol., 16(6):546-553, Jun. 2015.
Starrett et al., "The DNA cytosine deaminase APOBEC3H haplotype I likely contributes to breast and lung cancer mutagenesis," Nat. Commun., 7:12918, Sep. 2016.
Stenglein et al., "APOBEC3 proteins mediate the clearance of foreign DNA from human cells," Nat. Struct. Mol. Biol., 17(2):222-229, Feb. 2010.
Swanton et al., "APOBEC enzymes: mutagenic fuel for cancer evolution and heterogeneity," Cancer Discov., 5(7):704-712, Jul. 2015.
Teh et al., "The 1.48 A resolution crystal structure of the homotetrameric cytidine deaminase from mouse," Biochemistry, 45(25):7825-7833, Jun. 2006.
Vagin and Teplyakov, "Molecular replacement with MOLREP," Acta. Crystallogr. D. Biol. Crystallogr., 66(Pt 1):22-25, Jan. 2010.
Walker et al., "Mutational Spectrum, Copy Number Changes, and Outcome: Results of a Sequencing Study of Patients With Newly Diagnosed Myeloma," J. Clin, Oncol., 33(33):3911-3920, Nov. 2015.
Wang et al., "Altering the spectrum of immunoglobulin V gene somatic hypermutation by modifying the active site of AID," J. Exp. Med., 207(1): 141-153, Jan. 2010.
Xiao et al., "Crystal structures of APOBEC3G N-domain alone and its complex with DNA," Nat. Commun., 7:12193, Aug. 2016.
Yamano et al., "Crystal Structure of Cpf1 in Complex with Guide RNA and Target DNA," Cell, 165(4):949-962, May 2016.
Yan et al., "Increased APOBEC3B Predicts Worse Outcomes in Lung Cancer: A Comprehensive Retrospective Study," J. Cancer, 7(6):618-625, Mar. 2016.
Yu et al., "Single-strand specificity of APOBEC3G accounts for minus-strand deamination of the HIV genome," Nat. Struct. Mol. Biol., 11(5):435-442, May 2004.
Albin et al., "Long-Term Restriction by APOBEC3F Selects Human Immunodeficiency Virus Type 1 Variants with Restored Vif Function," J. Virol. 84(19): 10209-10219, Oct. 2010.
Apolonia et al., "Promiscuous RNA Binding Ensures Effective Encapsidation of APOBEC3 Proteins by HIV-1," PLoS Pathogens, 11(1):e1004609, Jan. 15, 2015, 22 pages.
Ara et al., "Different Mutagenic Potential of HIV-1 Restriction Factors APOBEC3G and APOBEC3F is Determined by Distinct Single-Stranded DNA Scanning Mechanisms," PLoS Pathog, 10(3):e1004024, Mar. 20, 2014, 21 pages.
Basu et al., "The RNA Exosome Targets the AID Cytidine Deaminase to Both Strands of Transcribed Duplex DNA Substrates," Cell, 144(3):353-363, Feb. 4, 2011.
Bogerd et al., "Single-stranded RNA facilitates nucleocapsid: APOBEC3G complex formation," RNA, 14(6): 1228-1236, Jun. 1, 2008.

(56) References Cited

OTHER PUBLICATIONS

Bouzidi et al., "APOBEC3DE Antagonizes Hepatitis B Virus Restriction Factors APOBEC3F and APOBEC3G," J. Mol. Biology, 428(17):3514-3528, Aug. 28, 2016.

Bransteitter et al., "Activation-induced cytidine deaminase deaminates deoxycytidine on single-stranded DNA but requires the action of Rnase," Proceedings of the National Academy of Sciences, 100(7):4102-4107, Apr. 1, 2003.

Browne et al., "Restriction of HIV-1 by APOBEC3G is cytidine deaminase-dependent," Virology, 387(2):313-321, May 10, 2009.

Cen et al., "The Interaction between HIV-1 Gag and APOBEC3G," Journal of Biological Chemistry, 279(32):33177-33184, Aug. 6, 2004.

Chelico et al., "APOBEC3G DNA deaminase acts processively 3'→5' on single-stranded DNA," Nat. Struct. Mol. Biology, 13(5):392-399, May 2006.

Chiu et al., "High-molecular-mass APOBEC3G complexes restrict Alu retrotransposition," Proceedings of the National Academy of Sciences, 103(42):15588-15593, Oct. 17, 2006.

Emsley et al., "Features and development of Coot," Acta. Crystallogr. D. Biol. Crystallography, 66(Pt 4):486-501, Apr. 2010.

Feng et al., "Deamination-independent restriction of LINE-1 retrotransposition by APOBEC3H," Scientific Reports, 7(1): 10881, Sep. 7, 2017, 11 pages.

Gallois-Montbrun et al., "Antiviral Protein APOBEC3G Localizes to Ribonucleoprotein Complexes Found in P Bodies and Stress Granules," J. Virology, 81(5):2165-2178, Mar. 1, 2007.

Gallois-Montbrun et al., "Comparison of Cellular Ribonucleoprotein Complexes Associated with the APOBEC3F and APOBEC3G Antiviral Proteins," J. Virology, 82(11):5636-5642, Jun. 1, 2008.

GenBank Accession No. AAH69023.1, "Apolipoprotein B mRNA editing enzyme, catalytic polypeptide-like 3H [*Homo sapiens*]," Mar. 6, 2012, 2 pages.

GenBank Accession No. ACH69768.1, "APOBEC3Z3 [Sus scrofa]," Dec. 16, 2008, 1 page.

GenBank Accession No. ACJ60858.1, "apolipoprotein B mRNA editing enzyme catalytic polypeptide-like protein 3H [Gorilla gorilla]," Mar. 9, 2010, 1 page.

GenBank Accession No. ACJ60860.1, "apolipoprotein B mRNA editing enzyme catalytic polypeptide-like protein 3H [Symphalangus syndactylus]," Mar. 9, 2010, 1 page.

GenBank Accession No. ACJ60861.1, "apolipoprotein B mRNA editing enzyme catalytic polypeptide-like protein 3H [*Homo sapiens*]," Mar. 9, 2010, 1 page.

GenBank Accession No. ACK77772.1, "APOBEC3H [*Homo sapiens*]," Dec. 22, 2008, 1 page.

GenBank Accession No. ACK77773.1, "APOBEC3H [*Homo sapiens*]," Dec. 22, 2008, 1 page.

GenBank Accession No. ACK77774.1, "APOBEC3H [*Homo sapiens*]," Dec. 22, 2008, 1 page.

GenBank Accession No. ACK77775.1, "APOBEC3H [*Homo sapiens*]," Dec. 22, 2008, 1 page.

GenBank Accession No. ACK77776.1, "APOBEC3H [*Homo sapiens*]," Dec. 22, 2008, 1 page.

GenBank Accession No. ACK77778.1, "APOBEC3H [*Homo sapiens*]," Dec. 22, 2008, 1 page.

GenBank Accession No. AGI04217.1, "apolipoprotein B editing enzyme catalytic polypeptide-like 3H [*Homo sapiens*]," Mar. 30, 2013, 1 page.

GenBank Accession No. FJ376614.1, "*Homo sapiens* clone HapII RDD-SV183 APOBEC3H (APOBEC3H) mRNA, complete cds, alternatively spliced," Dec. 22, 2008, 1 page.

GenBank Accession No. NP_001106181.2, "DNA dC->dU-editing enzyme APOBEC-3H [Felis catus]," Sep. 10, 2017, 2 pages.

GenBank Accession No. NP_001136078.1, "DNA dC->dU-editing enzyme APOBEC-3H [Pan troglodytes]," Sep. 21, 2016, 1 page.

GenBank Accession No. NP_001154853.1, "apolipoprotein B mRNA editing enzyme, catalytic polypeptide-like [Ovis aries]," Sep. 24, 2016, 1 page.

GenBank Accession No. NP_001159474.2. "DNA dC->dU-editing enzyme APOBEC-3H isoform SV-182 [*Homo sapiens*]," Oct. 9, 2017, 3 pages.

GenBank Accession No. NP_001159475.2, "DNA dC->dU-editing enzyme APOBEC-3H isoform SV-200 [*Homo sapiens*]," Oct. 9, 2017, 3 pages.

GenBank Accession No. NP_001159476.2, "DNA dC->dU-editing enzyme APOBEC-3H isoform SV-154 [*Homo sapiens*]," Oct. 9, 2017, 3 pages.

GenBank Accession No. NP_001229380.1, "DNA dC->dU-editing enzyme APOBEC-3H [Equus caballus]," Oct. 23, 2017, 1 page.

GenBank Accession No. NP_001332864.1, "DNA dC->dU-editing enzyme APOBEC-3H isoform 1 [Macaca mulatta]," Apr. 15, 2017, 2 pages.

GenBank Accession No. NP_001332865.1, "DNA dC->dU-editing enzyme APOBEC-3H [Papio anubis]," Jul. 28, 2017, 1 page.

GenBank Accession No. NP_001332866.1, "apolipoprotein B mRNA editing enzyme catalytic subunit 3H [Chlorocebus sabaeus]," Sep. 16, 2016, 1 page.

GenBank Accession No. NP_001333053.1, "apolipoprotein B mRNA editing enzyme, catalytic polypeptide-like 3F [Bos taurus]," Oct. 23, 2017, 2 pages.

GenBank Accession No. NP_001333059.1, "apolipoprotein B mRNA editing enzyme, catalytic polypeptide-like 3Z3 [Canis lupus familiaris]," Oct. 23, 2017, 1 page.

GenBank Accession No. NP_001635.2, "C->U-editing enzyme APOBEC-1 isoform a [*Homo sapiens*]," Oct. 3, 2017, 3 pages.

GenBank Accession No. NP_004891.4, "DNA dC->dU-editing enzyme APOBEC-3B isoform a [*Homo sapiens*]," Oct. 24, 2017, 3 pages.

GenBank Accession No. NP_055323.2, "DNA dC->dU-editing enzyme APOBEC-3C [*Homo sapiens*]," Sep. 10, 2017, 3 pages.

GenBank Accession No. NP_065712.1, "single-stranded DNA cytosine deaminase isoform 1 [*Homo sapiens*]," Oct. 3, 2017, 3 pages.

GenBank Accession No. NP_068594.1, "DNA dC->dU-editing enzyme APOBEC-3G isoform 1 [*Homo sapiens*]," Sep. 25, 2017, 3 pages.

GenBank Accession No. NP_660341.2, "DNA dC->dU-editing enzyme APOBEC-3F isoform a [*Homo sapiens*]," Oct. 2, 2017, 3 pages.

GenBank Accession No. NP_689639.2, "DNA dC->dU-editing enzyme APOBEC-3D [*Homo sapiens*]," Oct. 2, 2017, 3 pages.

GenBank Accession No. NP_861438.3, "DNA dC->dU-editing enzyme APOBEC-3H isoform SV-183 [*Homo sapiens*]," Oct. 9, 2017, 3 pages.

GenBank Accession No. XP_009232662.1, "PREDICTED: DNA dC->dU-editing enzyme APOBEC-3H isoform X1 [Pongo abelii]," Sep. 23, 2014, 1 page.

GenBank Accession No. XP_011528292.1, "PREDICTED: DNA dC->dU-editing enzyme APOBEC-3H isoform X1 [*Homo sapiens*]," Jun. 6, 2016, 1 page.

GenBank Accession No. XP_011528293.1, "PREDICTED: DNA dC->dU-editing enzyme APOBEC-3H isoform X1 [*Homo sapiens*]," Jun. 6, 2016, 1 page.

GenBank Accession No. XP_011528294.1, "PREDICTED: DNA dC->dU-editing enzyme APOBEC-3H isoform X2 [*Homo sapiens*]," Jun. 6, 2016, 1 page.

GenBank Accession No. XP_011710626.1, "PREDICTED: DNA dC->dU-editing enzyme APOBEC-3H isoform X1 [Macaca nemestrina]," Mar. 30, 2015, 1 page.

Gross et al., "The structure of the chromophore within DsRed, a red fluorescent protein from coral," Proc. Natl. Acad. Sci. USA, 97(22):11990-11995, Oct. 2000.

Gu et al., "Biochemical Characterization of APOBEC3H Variants: Implications for Their HIV-1 Restriction Activity and mC Modification," J. Mol. Biology, 428(23):4626-4638, Nov. 20, 2016.

Haché et al., "Evolution of HIV-1 isolates that use a novel Vif-independent mechanism to resist restriction by human APOBEC3G," Curr. Biology, 18(11):819-824, Jun. 2008.

Harari et al., "Polymorphisms and Splice Variants Influence the Antiretroviral Activity of Human APOBEC3H," J. Virol., 83(1):295-303, Jan. 2009.

(56) References Cited

OTHER PUBLICATIONS

Harris et al., "RNA editing enzyme APOBEC1 and some of its homologs can act as DNA mutators," Mol. Cell, 10(5):1247-1253, Nov. 2002.
Hultquist et al., "Human and Rhesus APOBEC3D, APOBEC3F, APOBEC3G, and APOBEC3H Demonstrate a Conserved Capacity to Restrict Vif-Deficient HIV-1," J. Virology., 85(21):11220-11234, Nov. 2011.
Huthoff et al., "Identification of Amino Acid Residues in APOBEC3G Required for Regulation by Human Immunodeficiency Virus Type 1 Vif and Virion Encapsidation," J. Virology, 81(8):3807-3815, Apr. 15, 2007.
Izumi et al., "Mov10 and APOBEC3G Localization to Processing Bodies is Not Required for Virion Incorporation and Antiviral Activity," J. Virology, 87(20):11047-11062, Oct. 15, 2013.
Jiang et al., "Structural basis of RNA recognition and activation by innate immune receptor RIG-I," Nature, 479(7373):423-427, Nov. 2011.
Kelley et al., "The Phyre2 web portal for protein modeling, prediction and analysis," Nat. Protocols, 10(6):845-858, Jun. 2015.
Khan et al., "Viral RNA is Required for the Association of APOBEC3G with Human Immunodeficiency Virus Type 1 Nucleoprotein Complexes," J. Virology, 79(9):5870-5874, May 1, 2005.
Köck et al., "Hypermutation of hepatitis B virus genomes by APOBEC3G, APOBEC3C and APOBEC3H," J. Gen. Virology, 89(5):1184-1191, May 1, 2008.
Kozak et al., "The Anti-HIV-1 Editing Enzyme APOBEC3G Binds HIV-1 RNA and Messenger RNAs That Shuttle between Polysomes and Stress Granules," J. Bio. Chemistry, 281 (39):29105-19, Sep. 29, 2006.
LaRue et al., "The artiodactyl APOBEC3 innate immune repertoire shows evidence for a multi-functional domain organization that existed in the ancestor of placental mammals," BMC Mol. Biology, 9(1): 104, Dec. 1, 2008, 20 pages.
Leonard et al., "The PKC/NF-kB Signaling Pathway Induces APOBEC3B Expression in Multiple Human Cancers," Cancer Research, 75(21):4538-4547, Nov. 2015.
Li et al., "APOBEC3 Multimerization Correlates with HIV-1 Packaging and Restriction Activity in Living Cells," J. Mol. Biology, 426(6):1296-1307, Mar. 20, 2014.
Li et al., "Polymorphism in Human APOBEC3H Affects a Phenotype Dominant for Subcellular Localization and Antiviral Activity," J. Virology, 85(16):8197-8207, Aug. 2011.
McDougall et al., "Direct evidence that RNA inhibits APOBEC3G ssDNA cytidine deaminase activity," Biochem. Biophys. Res. Communications, 412(4):612-617, Sep. 9, 2011.
Mitra et al., "Sequence and structural determinants of human APOBEC3H deaminase and anti-HIV-1 activities," Retrovirology, 12(1):3, Dec. 2015, 15 pages.
Miyagi et al., "Enzymatically Active APOBEC3G is Required for Efficient Inhibition of Human Immunodeficiency Virus Type 1," J. Virology, 81 (24): 13346-53, Dec. 15, 2007.
Münk et al., "Functions, structure, and read-through alternative splicing of feline APOBEC3 genes," Genome Biology, 9(3):R48, Mar. 1, 2008, 20 pages.
Nakano et al., "HIV-1 competition experiments in humanized mice show that APOBEC3H imposes selective pressure and promotes virus adaptation," PLoS Pathogens, 13(5):e1006348, May 5, 2017, 24 pages.
Nowak et al., "The splicing regulator PTBP2 interacts with the cytidine deaminase AID and promotes binding of AID to switch-region DNA," Nat. Immunology, 12(2): 160-166, Feb. 2011.
OhAinle et al., "Antiretroelement Activity of APOBECH Was Lost Twice in Recent Human Evolution," Cell Host Microbe, 4(3)249-259, Oct. 2008.
Ooms et al., "APOBEC3A, APOBEC3B, and APOBEC3H Haplotype 2 Restrict Human T-lymphotropic Virus Type 1,". J. Virology, 86(11):6097-108, Jun. 1, 2012.
Ooms et al., "HIV-1 Vif Adaptation to Human APOBEC3H Haplotypes," Cell Host Microbe, 14(4):411-421, Oct. 16, 2013.
Otwinowski et al., "Processing of X-Ray Diffraction Data Collected in Oscillation Mode," Methods in Enzymology, 276:307-326, Jan. 1997.
Peden et al., "Changes in growth properties on passage in tissue culture of viruses derived from infectious molecular clones of HIV-1LAI, HIV-1MAL, and HIV-1ELI," Virology 185(2):661-672, Dec. 1991.
Phalora et al., "HIV-1 Replication and APOBEC3 Antiviral Activity Are Not Regulated by P Bodies," J. Virology, 86(21):11712-11724, Nov. 1, 2012.
Pletnev et al., "Rotational order-disorder structure of fluorescent protein FP480," Acta Crystallogr D Biol Crystallography, 65(9):906-912, Sep. 2009.
Pletnev et al., "The rotational order-disorder structure of the reversibly photoswitchable red fluorescent protein rsTagRFP," Acta Crystallogr D Biol Crystallogr, 70(1):31-39, Jan. 2014.
Qiao et al., "AID Recognizes Structured DNA for Class Switch Recombination," Molecular Cell, 67(3):361-373, Aug. 3, 2017.
Refsland et al., "Natural Polymorphisms in Human APOBEC3H and HIV-1 Vif Combine in Primary T Lymphocytes to Affect Viral G-to-A Mutation Levels and Infectivity," PLoS Genetics, 10(11):e1004761, Nov. 2014, 12 pages.
Schäfer et al., "Specific packaging of APOBEC3G into HIV-1 virions is mediated by the nucleocapsid domain of the gag polyprotein precursor," Virology, 328(2): 163-168, Oct. 25, 2004.
Schumacher et al., "The DNA Deaminase Activity of Human APOBEC3G is Required for Ty1, MusD, and Human Immunodeficiency Virus Type 1 Restriction," J. Virology, 82(6)2652-2660, Mar. 15, 2008.
Shaban et al., "The Antiviral and Cancer Genomic DNA Deaminase APOBEC3H Is Regulated by an RNA-Mediated Dimerization Mechanism," Mol. Cell, 69(1):75-86, Jan. 4, 2018.
Shaban, "RNA Inhibits Human APOBEC3H by a Novel RNA Duplex-Mediated Enzyme Dimerization Mechanism," Presented at West Coast Retrovirus Meeting, Palm Springs, California, USA, Oct. 5-7, 2017, 16 pages.
Shaner et al., "Improved monomeric red, orange and yellow fluorescent proteins derived from Discosoma sp. red fluorescent protein." Nat Biotechnology, 22(12):1567-1572, Dec. 2004.
Sharma et al., "APOBEC3A cytidine deaminase induces RNA editing in monocytes and macrophages," Nat. Communications, 6(1):6881, Apr. 21, 2015, 15 pages.
Shi et al., "Structural basis for targeted DNA cytosine deamination and mutagenesis by APOBEC3A and APOBEC3B," Nat. Struct. Mol. Biology, 24(2):131-139, Dec. 19, 2016.
Shlyakhtenko et al., "Atomic Force Microscopy Studies Provide Direct Evidence for Dimerization of the HIV Restriction Factor APOBEC3G," J. Bio. Chemistry, 286(5):3387-95, Feb. 4, 2011.
Shlyakhtenko et al., "Interaction of APOBEC3A with DNA Assessed by Atomic Force Microscopy," PloS One, 9(6):e99354, Jun. 6, 2014, 6 pages.
St. Martin et al., "A fluorescent reporter for quantification and enrichment of DNA editing by APOBEC-Cas9 or cleavage by Cas9 in living cells," Nucl. Acids Research, 46(14):e84, May 9, 2018, 10 pages.
Stenglein et al., "Two Regions within the Amino-Terminal Half of APOBEC3G Cooperate To Determine Cytoplasmic Localization," J. Virology, 82(19):9591-9599, Oct. 2008.
Svarovskaia et al., "Human Apolipoprotein B mRNA-editing Enzyme-catalytic Polypeptide-like 3G (APOBEC3G) is Incorporated into HIV-1 Virions through Interactions with Viral and Nonviral RNAs," J. Bio. Chemistry, 279(34):35822-35828, Aug. 20, 2004.
Tan et al., "Sole copy of Z2-type human cytidine deaminase APOBEC3H has inhibitory activity against retrotransposons and HIV-1," The FASEB Journal, 23(1):279-287, Jan. 2009.
Teng et al., "Molecular Cloning of an Apolipoprotein B Messenger RNA Editing Protein," Science, 260(5115):1816-1819, Jun. 18, 1993.
Thielen et al., "T Cells Contain an RNase-Insensitive Inhibitor of APOBEC3G Deaminase Activity," PLoS Pathogens, 3(9): 1320-1334, Sep. 2007.
UniProt Accession No. P31941.3, "DNA dC->dU-editing enzyme APOBEC-3A," Oct. 25, 2017.
UniProt Accession No. Q6NTF7.3, "DNA dC->dU-editing enzyme APOBEC-3H," Sep. 27, 2017.
UniProt Accession No. Q9UH17.1, "DNA dC->dU-editing enzyme APOBEC-3B," Sep. 27, 2017, 8 pages.
Wang et al., "7SL RNA Mediates Virion Packaging of the Antiviral Cytidine Deaminase-APOBEC3G," J. Virology, 81(23):13112-13124, Dec. 1, 2007.

(56) References Cited

OTHER PUBLICATIONS

Wang et al., "Analysis of Human APOBEC3H Haplotypes and Anti-Human Immunodeficiency Virus Type 1 Activity," J. Virology, 85(7):3142-3152, Apr. 2011.

Wang et al., "Enhanced base editing by co-expression of free uracil DNA glycosylase inhibitor," Cell Research, 27:1289-1292, Aug. 29, 2017.

Wang et al., "Interaction with 7SL RNA but Not with HIV-1 Genomic RNA or P Bodies is Required for APOBEC3F Virion Packaging," J. Mol. Biology, 375(4): 1098-1112, Jan. 25, 2008.

Wichroski et al., "Human Retroviral Host Restriction Factors APOBEC3G and APOBEC3F Localize to mRNA Processing Bodies," PLoS Pathogens, 2(5):e41, May 12, 2006, 10 pages.

Xiao et al., "Structural determinants of APOBEC3B non-catalytic domain for molecular assembly and catalytic regulation," Nucl. Acids Research, 45(12):7494-7506, Jul. 2017.

York et al., "The RNA Binding Specificity of Human APOBEC3 Proteins Resembles That of HIV-1 Nucleocapsid," PLoS Pathogens, 12(8):e1005833, Aug. 19, 2016, 24 pages.

Zennou et al., "APOBEC3G Incorporation into Human Immunodeficiency Virus Type 1 Particles," J. Virology, 78(21):12058-12061, Nov. 1, 2004.

Zhen et al., "Reduced APOBEC3H Variant Anti-Viral Activities Are Associated with Altered RNA Binding Activities," PloS One, 7(7):e38771, Jul. 30, 2012, 10 pages.

U.S. Appl. No. 16/663,578, filed Oct. 25, 2019, Reuben S. Harris.

\* cited by examiner

FIG. 2

```
A3A  13   MDPHIFTSNFNG---IGRHKTYLCYEVERL｜NG｜SV｜MDQHR｜FI｜NQAKNLLCGFYGR｜HAEL  73
A3B  193  MDPDTFTFNFNNDPLVLRRRQ｜TYLCYEVERL｜NG｜WV｜MDQHM｜EL｜NEAKNLLCGFYGR｜HAEL  256
          *** ::  ::* *       :** *****:** :***** :* *************** ****
              α1           Loop1       β1    β2'      β2        Loop3    α2

A3A  74   RFLDLVPSLQ｜LDPAQ｜IYRVTWFIS｜WSPCFSWG｜CAGEVRAFLQENTH｜VRLRIFA｜ARIY｜DYDPLYK  137
A3B  257  RFLDLVPSLQ｜LDPAQ｜IYRVTWFIS｜WSPCFSWG｜CAGEVRAFLQENTH｜VRLRIFA｜ARIY｜DYDPLYK  320
          ********** ***** ********* ******** ************* ******* **** *******
              α2              β3              α3             β4   Loop7

A3A  138  EALQMLRDAGA｜QVS｜IMTYDEFKHCWDTFV｜DHQGCPFQPWDGLDEHSQALSGRLRAILQ｜NQGN  199  (SEQ ID NO:1)
A3B  321  EALQMLRDAGA｜QVS｜IMTYDEFEYCWDTFV｜YRQGCPFQPWDGLEEHSQALSGRLRAILQ｜NQGN  382  (SEQ ID NO:2)
          *********** *** *******: ***** : ********** ***************** ****
              α4   β5        α5                        α6
```

FIG. 3A
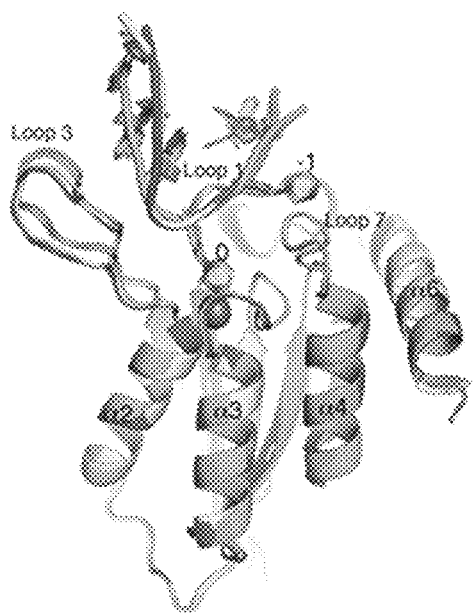
FIG. 3B
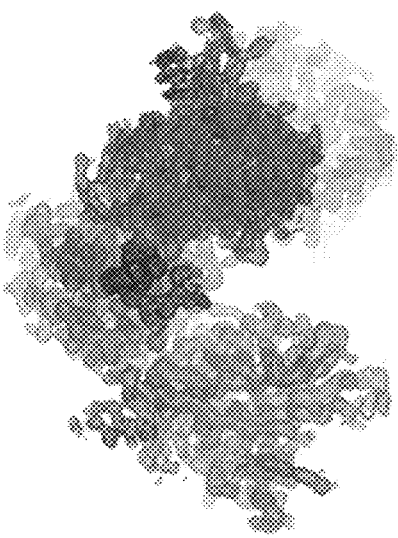
FIG. 3C
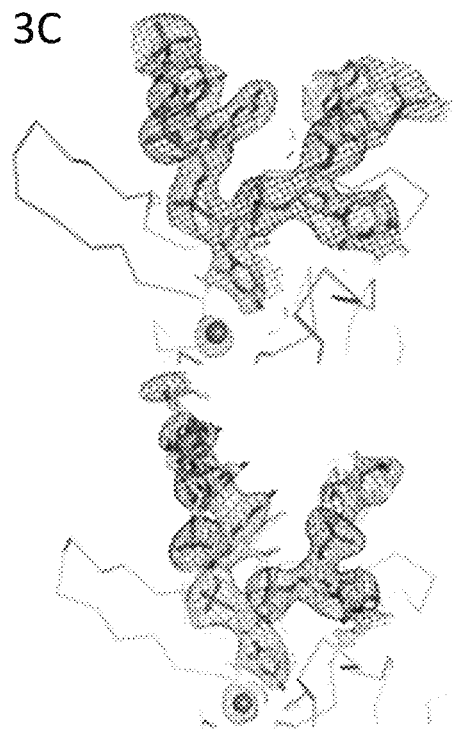
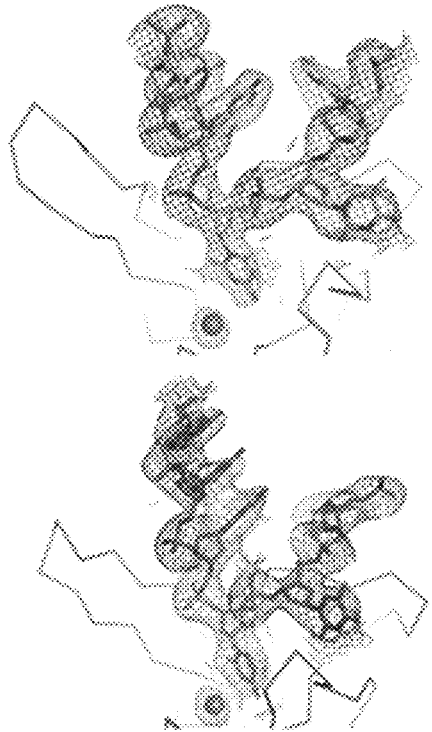

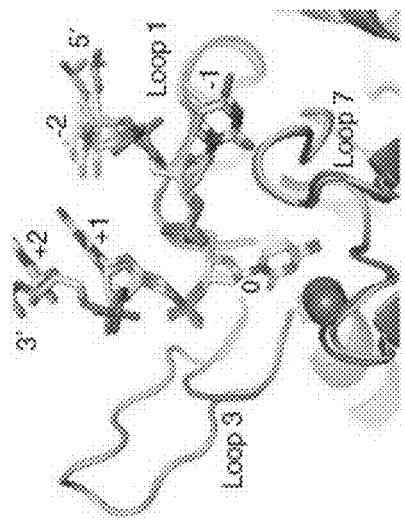
FIG. 5A
FIG. 5B
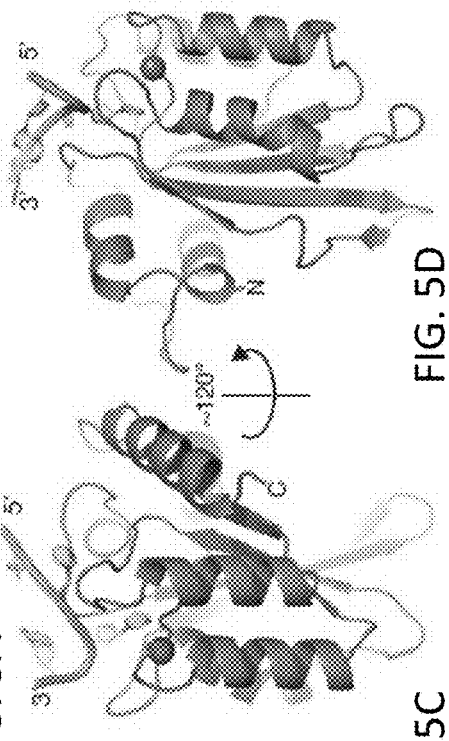
FIG. 5C
FIG. 5D
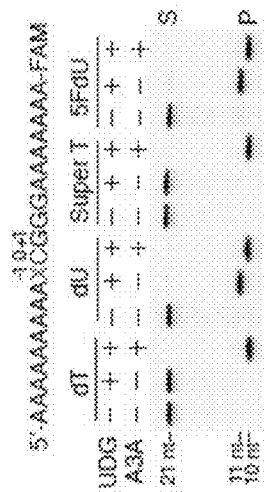
FIG. 5E
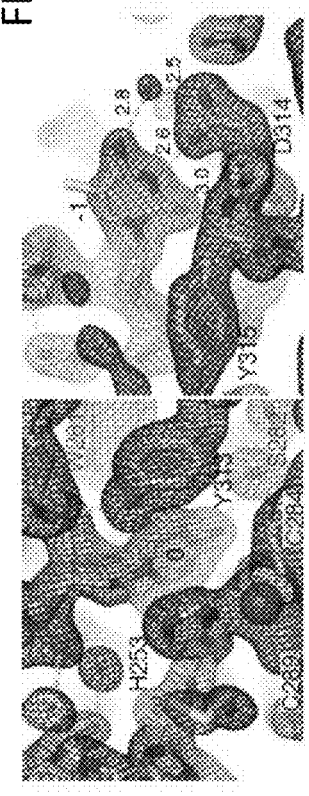
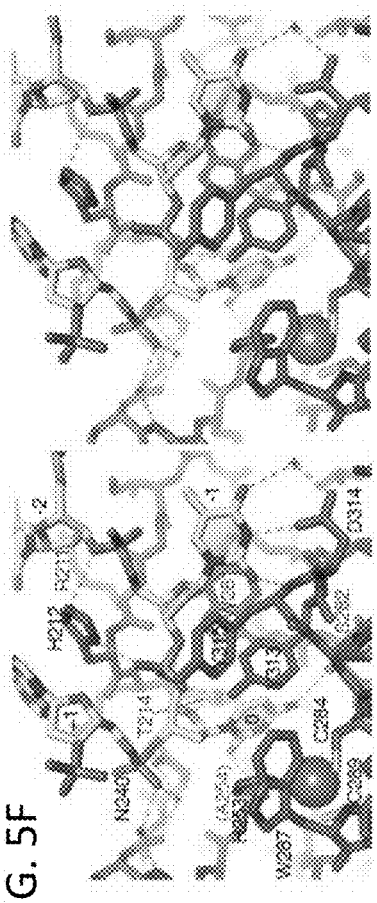
FIG. 5F

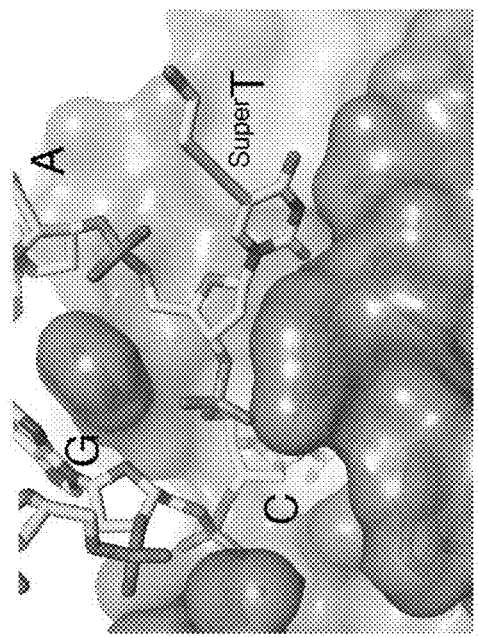
FIG. 7A
5' A9 SuperTCGGGA7
FIG. 7B
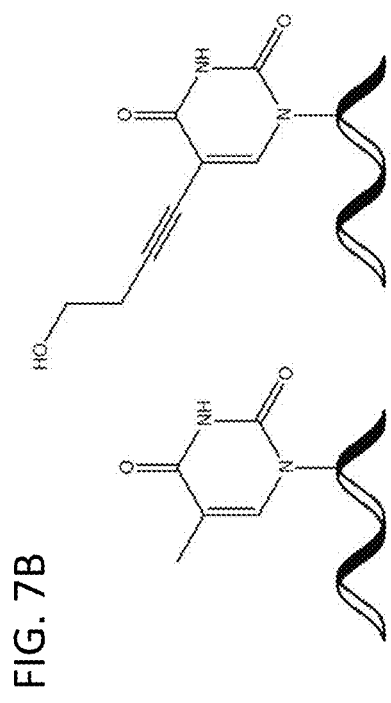
FIG. 7C
FIG. 7D
FIG. 7E

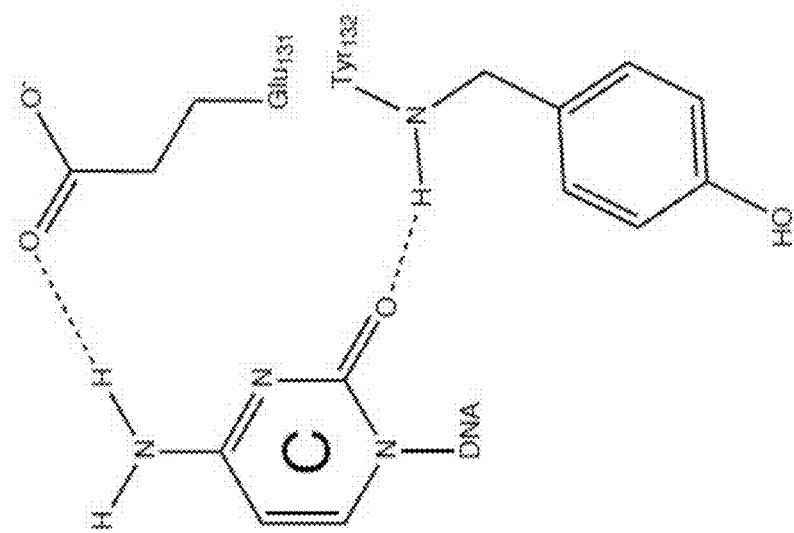
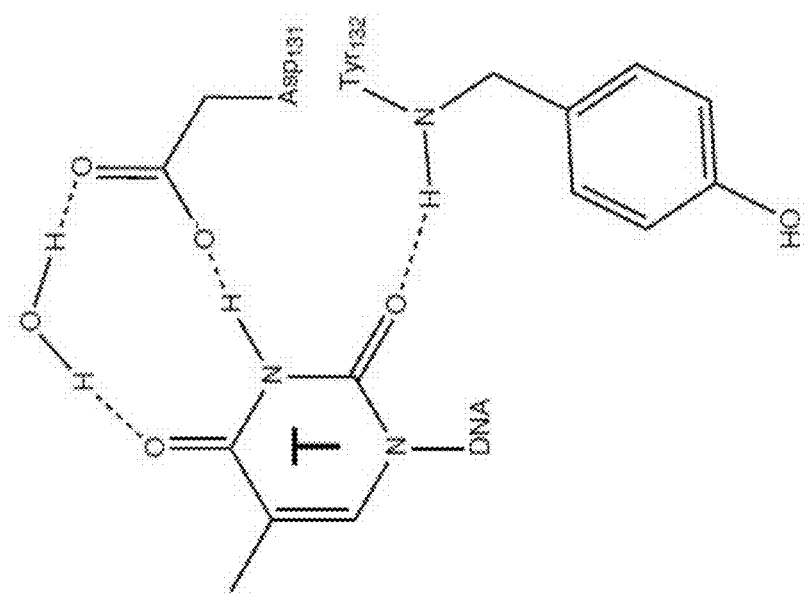
FIG. 11

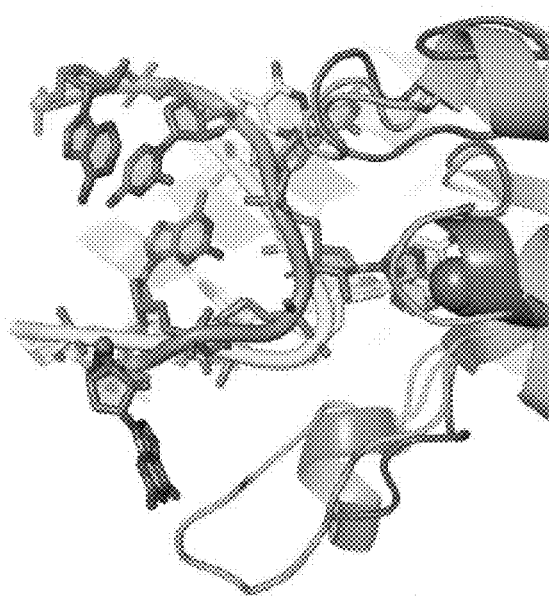
FIG. 12A
A3A-ssDNA
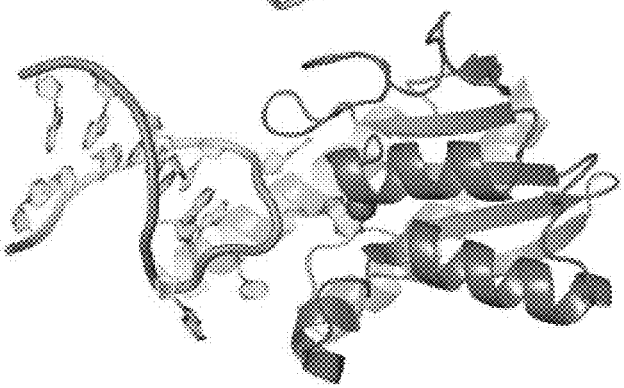
FIG. 12B
TadA-tRNA
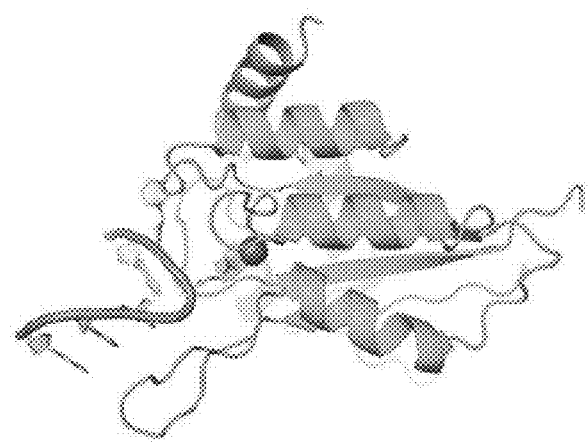

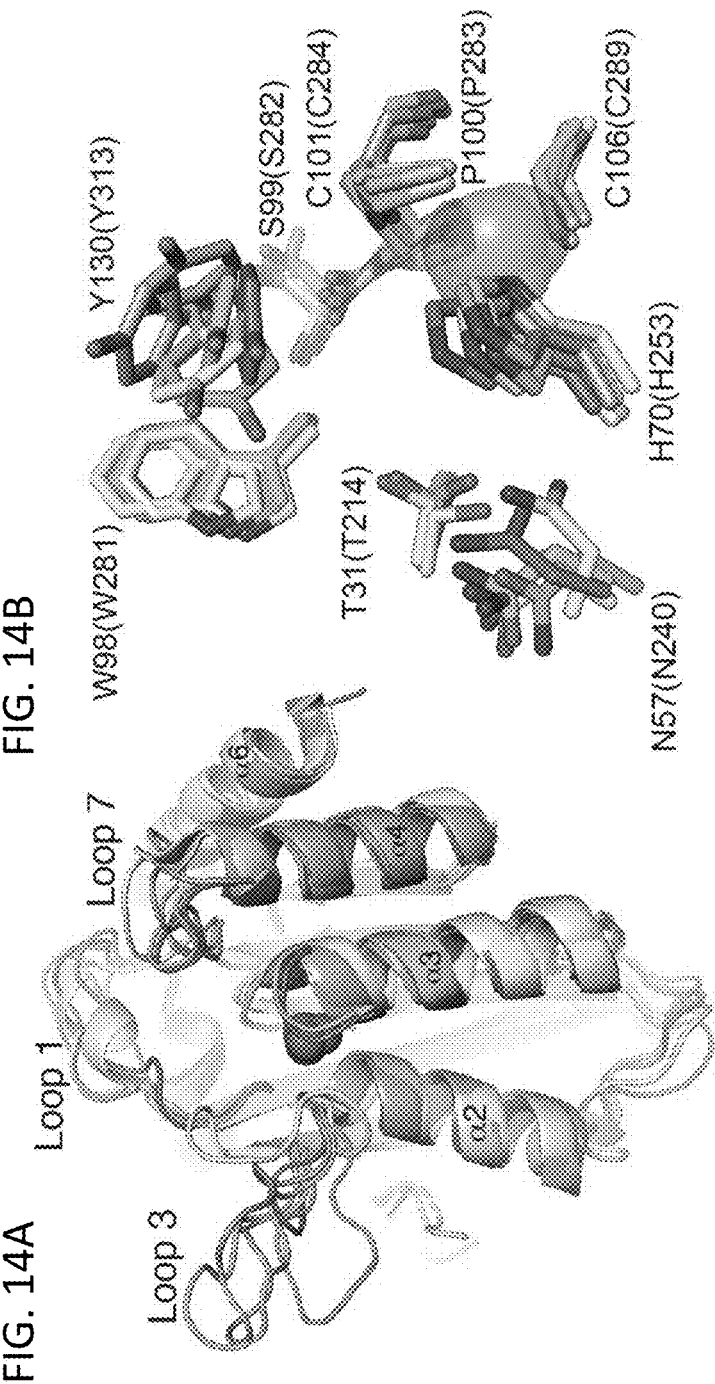

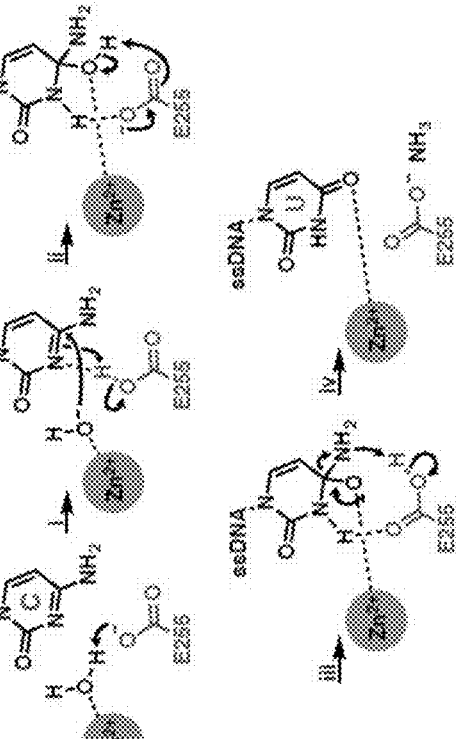
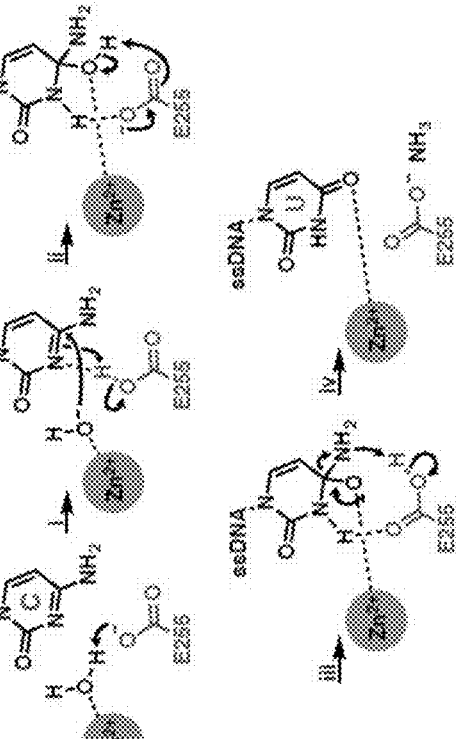
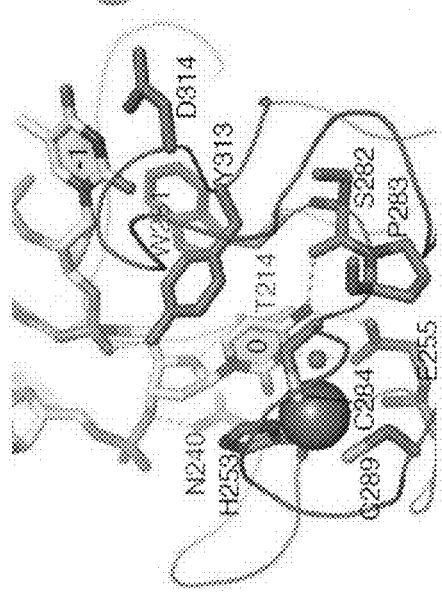
FIG. 15A
FIG. 15B
FIG. 15E
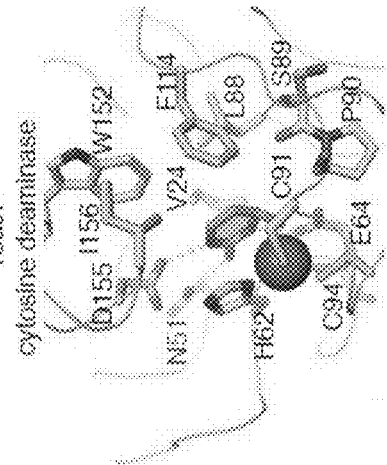
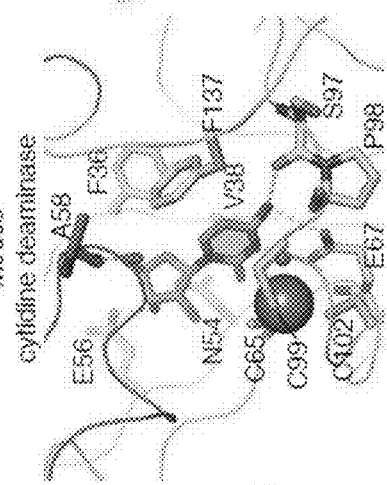
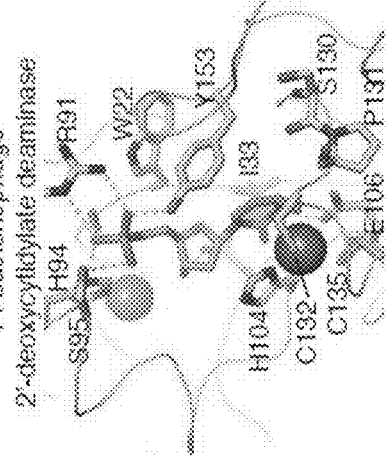
FIG. 15C
FIG. 15D

SEQUENCE LISTING

```
<160> NUMBER OF SEQ ID NOS: 75

<210> SEQ ID NO 1
<211> LENGTH: 187
<212> TYPE: PRT
<213> ORGANISM: Homo sapiens

<400> SEQUENCE: 1

Met Asp Pro His Ile Phe Thr Ser Asn Phe Asn Asn Gly Ile Gly Arg
1               5                   10                  15

His Lys Thr Tyr Leu Cys Tyr Glu Val Glu Arg Leu Asp Asn Gly Thr
            20                  25                  30

Ser Val Lys Met Asp Gln His Arg Gly Phe Leu His Asn Gln Ala Lys
        35                  40                  45

Asn Leu Leu Cys Gly Phe Tyr Gly Arg His Ala Glu Leu Arg Phe Leu
    50                  55                  60

Asp Leu Val Pro Ser Leu Gln Leu Asp Pro Ala Gln Ile Tyr Arg Val
65                  70                  75                  80

Thr Trp Phe Ile Ser Trp Ser Pro Cys Phe Ser Trp Gly Cys Ala Gly
                85                  90                  95

Glu Val Arg Ala Phe Leu Gln Glu Asn Thr His Val Arg Leu Arg Ile
            100                 105                 110

Phe Ala Ala Arg Ile Tyr Asp Tyr Asp Pro Leu Tyr Lys Glu Ala Leu
        115                 120                 125

Gln Met Leu Arg Asp Ala Gly Ala Gln Val Ser Ile Met Thr Tyr Asp
    130                 135                 140

Glu Phe Lys His Cys Trp Asp Thr Phe Val Asp His Gln Gly Cys Pro
145                 150                 155                 160

Phe Gln Pro Trp Asp Gly Leu Asp Glu His Ser Gln Ala Leu Ser Gly
                165                 170                 175

Arg Leu Arg Ala Ile Leu Gln Asn Gln Gly Asn
            180                 185

<210> SEQ ID NO 2
<211> LENGTH: 190
<212> TYPE: PRT
<213> ORGANISM: Homo sapiens

<400> SEQUENCE: 2

Met Asp Pro Asp Thr Phe Thr Phe Asn Phe Asn Asn Asp Pro Leu Val
1               5                   10                  15

Leu Arg Arg Arg Gln Thr Tyr Leu Cys Tyr Glu Val Glu Arg Leu Asp
            20                  25                  30

Asn Gly Thr Trp Val Leu Met Asp Gln His Met Gly Phe Leu Cys Asn
        35                  40                  45
```

```
Glu Ala Lys Asn Leu Leu Cys Gly Phe Tyr Gly Arg His Ala Glu Leu
 50                  55                  60

Arg Phe Leu Asp Leu Val Pro Ser Leu Gln Leu Asp Pro Ala Gln Ile
 65                  70                  75                  80

Tyr Arg Val Thr Trp Phe Ile Ser Trp Ser Pro Cys Phe Ser Trp Gly
                 85                  90                  95

Cys Ala Gly Glu Val Arg Ala Phe Leu Gln Glu Asn Thr His Val Arg
            100                 105                 110

Leu Arg Ile Phe Ala Ala Arg Ile Tyr Asp Tyr Asp Pro Leu Tyr Lys
        115                 120                 125

Glu Ala Leu Gln Met Leu Arg Asp Ala Gly Ala Gln Val Ser Ile Met
130                 135                 140

Thr Tyr Asp Glu Phe Glu Tyr Cys Trp Asp Thr Phe Val Tyr Arg Gln
145                 150                 155                 160

Gly Cys Pro Phe Gln Pro Trp Asp Gly Leu Glu His Ser Gln Ala
                165                 170                 175

Leu Ser Gly Arg Leu Arg Ala Ile Leu Gln Asn Gln Gly Asn
        180                 185                 190

<210> SEQ ID NO 3
<211> LENGTH: 21
<212> TYPE: DNA
<213> ORGANISM: Artificial Sequence
<220> FEATURE:
<223> OTHER INFORMATION: synthetic

<400> SEQUENCE: 3
aaaaaaaaat cgggaaaaaa a                                              21

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
aaaaaaaaau cgggaaaaaa a                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: 5-hydroxybutynl-2'-deoxyuridine

<400> SEQUENCE: 5
aaaaaaaaan cgggaaaaaa a                                              21

<210> SEQ ID NO 6
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: 5-fluorodeoxyuridine
```

<400> SEQUENCE: 6
aaaaaaaaan cgggaaaaaa a                                               21

<210> SEQ ID NO 7
<211> LENGTH: 4104
<212> TYPE: DNA
<213> ORGANISM: Streptococcus pyogenes

<400> SEQUENCE: 7

| | | |
|---|---|---|
| atggataaga aatactcaat aggcttagat atcggcacaa atagcgtcgg atgggcggtg | 60 |
| atcactgatg attataaggt tccgtctaaa aagttcaagg ttctgggaaa tacagaccgc | 120 |
| cacagtatca aaaaaatct tatagggct cttttatttg gcagtggaga gacagcggaa | 180 |
| gcgactcgtc tcaaacggac agctcgtaga aggtatacac gtcggaagaa tcgtatttgt | 240 |
| tatctacagg agattttttc aaatgagatg gcgaaagtag atgatagttt ctttcatcga | 300 |
| cttgaagagt cttttttggt ggaagaagac aagaagcatg aacgtcatcc tatttttgga | 360 |
| aatatagtag atgaagttgc ttatcatgag aaatatccaa ctatctatca tctgcgaaaa | 420 |
| aaattggcag attctactga taaagcggat ttgcgcttaa tctatttggc cttagcgcat | 480 |
| atgattaagt ttcgtggtca ttttttgatt gagggagatt aaatcctga taatagtgat | 540 |
| gtggacaaac tatttatcca gttggtacaa atctacaatc aattatttga agaaaaccct | 600 |
| attaacgcaa gtagagtaga tgctaaagcg attcttctg cacgattgag taaatcaaga | 660 |
| cgattagaaa atctcattgc tcagctcccc ggtgagaaga gaatggctt gtttgggaat | 720 |
| ctcattgctt tgtcattggg attgacccct aattttaaat caattttga tttggcagaa | 780 |
| gatgctaaat tacagctttc aaaagatact tacgatgatg atttagataa tttattggcg | 840 |
| caaattggag atcaatatgc tgatttgttt ttggcagcta agaatttatc agatgctatt | 900 |
| ttactttcag atatcctaag agtaaatagt gaaataacta aggctcccct atcagcttca | 960 |
| atgattaagc gctacgatga acatcatcaa gacttgactc ttttaaaagc tttagttcga | 1020 |
| caacaacttc cagaaaagta taagaaatc ttttttgatc aatcaaaaaa cggatatgca | 1080 |
| ggttatattg atgggggagc tagccaagaa gaatttttata aatttatcaa accaatttta | 1140 |
| gaaaaaatgg atggtactga ggaattattg gtgaaactaa atcgtgaaga tttgctgcgc | 1200 |
| aagcaacgga ccttttgacaa cggctctatt ccccatcaaa ttcacttggg tgagctgcat | 1260 |
| gctattttga agacaagaa agacttttat ccattttaa aagacaatcg tgagaagatt | 1320 |
| gaaaaaatct tgactttcg aattccttat tatgttggtc cattggcgcg tggcaatagt | 1380 |
| cgttttgcat ggatgactcg gaagtctgaa gaaacaatta ccccatggaa ttttgaagaa | 1440 |
| gttgtcgata aggtgcttc agctcaatca tttattgaac gcatgacaaa ctttgataaa | 1500 |
| aatcttccaa atgaaaagt actaccaaaa catagtttgc tttatgagta ttttacggtt | 1560 |
| tataacgaat tgacaaaggt caaatatgtt actgagggaa tgcgaaaacc agcatttctt | 1620 |
| tcaggtgaac agaagaaagc cattgttgat ttactcttca aaacaaatcg aaaagtaacc | 1680 |
| gttaagcaat taaagaaga ttatttcaaa aaatagaat gttttgatag tgttgaaatt | 1740 |
| tcaggagttg aagatagatt taatgcttca ttaggcgcct accatgattt gctaaaaatt | 1800 |
| attaaagata agatttttt ggataatgaa gaaatgaag atatcttaga ggatattgtt | 1860 |
| ttaacattga cettatttga agatagggg atgattgagg aaagacttaa acatatgct | 1920 |
| cacctctttg atgataaggt gatgaaacag cttaaacgtc gccgttatac tggttgggga | 1980 |
| cgtttgtctc gaaaattgat taatggtatt agggataagc aatctggcaa aacaatatta | 2040 |

```
gattttttga aatcagatgg ttttgccaat cgcaattttta tgcagctgat ccatgatgat    2100
agtttgacat ttaaagaaga tattcaaaaa gcacaggtgt ctggacaagg ccatagttta    2160
catgaacaga ttgctaactt agctggcagt cctgctatta aaaaaggtat tttacagact    2220
gtaaaaattg ttgatgaact ggtcaaagta atggggcata agccagaaaa tatcgttatt    2280
gaaatggcac gtgaaaatca gacaactcaa aagggccaga aaaattcgcg agagcgtatg    2340
aaacgaatcg aagaaggtat caagaattta ggaagtcaga ttcttaaaga gcatcctgtt    2400
gaaaatactc aattgcaaaa tgaaaagctc tatctctatt atctacaaaa tggaagagac    2460
atgtatgtgg accaagaatt agatattaat cgtttaagtg attatgatgt cgatcacatt    2520
gttccacaaa gtttcattaa agacgattca atagacaata aggtactaac gcgttctgat    2580
aaaaatcgtg gtaaatcgga taacgttcca agtgaagaag tagtcaaaaa gatgaaaaac    2640
tattggagac aacttctaaa cgccaagtta atcactcaac gtaagtttga taatttaacg    2700
aaagctgaac gtggaggttt gagtgaactt gataaagctg ttttatcaa acgccaattg    2760 gttgaaactc gccaaatcac taagcatgtg gcacaaattt tggatagtcg catgaatact    2820
aaatacgatg aaaatgataa acttattcga gaggttaaag tgattacctt aaaatctaaa    2880 ttagttttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttctt ttactctaat    3120 atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca agtattgtc catgccccaa gtcaatattg tcaagaaaac agaagtacag    3300
acaggcggat tctccaagga gtcaatttta ccaaaaagaa attcggacaa gcttattgct    3360
cgtaaaaaag actgggatcc aaaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaaaga gttcctttg aaaaaaaatcc gattgacttt    3540 ttagaagcta aaggatataa ggaagttaaa aaagacttaa tcattaaact acctaaatat    3600 agtcttttttg agttagaaaa cggtcgtaaa cggatgctgg ctagtgccgg agaattacaa    3660
aaaggaaatg agctggctct gccaagcaaa tatgtgaatt ttttatattt agctagtcat    3720
tatgaaaagt tgaagggtag tccagaagat aacgaacaaa acaattgtt tgtggagcag    3780 cataagcatt atttagatga gattattgag caaatcagtg aattttctaa gcgtgttatt    3840
ttagcagatg ccaatttaga taaagttctt agtgcatata acaaacatag agacaaacca    3900
atacgtgaac aagcagaaaa tattattcat ttatttacgt tgacgaatct ggagctccc    3960 gctgctttta aatattttga tacaacaatt gatcgtaaac gatatacgtc tacaaaagaa    4020
gttttagatg ccactcttat ccatcaatcc atcactggtc tttatgaaac acgcattgat    4080
ttgagtcagc taggaggtga ctga                                            4104
```

<210> SEQ ID NO 8
<211> LENGTH: 1367
<212> TYPE: PRT
<213> ORGANISM: Streptococcus pyogenes

```
<400> SEQUENCE: 8

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

-continued

```
Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830
```

-continued

```
Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Asp Ser Pro Thr Val Ala Tyr Ser Val Leu
            1130                1135                1140

Val Val Ala Lys Val Glu Lys Gly Lys Ser Lys Lys Leu Lys Ser
            1145                1150                1155

Val Lys Glu Leu Leu Gly Ile Thr Ile Met Glu Arg Ser Ser Phe
            1160                1165                1170

Glu Lys Asn Pro Ile Asp Phe Leu Glu Ala Lys Gly Tyr Lys Glu
            1175                1180                1185

Val Lys Lys Asp Leu Ile Ile Lys Leu Pro Lys Tyr Ser Leu Phe
            1190                1195                1200

Glu Leu Glu Asn Gly Arg Lys Arg Met Leu Ala Ser Ala Gly Glu
            1205                1210                1215

Leu Gln Lys Gly Asn Glu Leu Ala Leu Pro Ser Lys Tyr Val Asn
            1220                1225                1230
```

```
Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365
```

<210> SEQ ID NO 9
<211> LENGTH: 1368
<212> TYPE: PRT
<213> ORGANISM: Artificial Sequence
<220> FEATURE:
<223> OTHER INFORMATION: synthetic

<400> SEQUENCE: 9

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

-continued

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

-continued

His Leu Phe Asp Asp Lys Val Met Lys Gln Leu Lys Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

```
Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Gly Gly Gly Gly Ser
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: synthetic

<400> SEQUENCE: 11

Glu Ala Ala Ala Lys
1               5

<210> SEQ ID NO 12
<211> LENGTH: 16
<212> TYPE: PRT
<213> ORGANISM: Artificial Sequence
<220> FEATURE:
<223> OTHER INFORMATION: synthetic

<400> SEQUENCE: 12

Ser Gly Ser Glu Thr Pro Gly Thr Ser Glu Ser Ala Thr Pro Glu Ser
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: synthetic

<400> SEQUENCE: 13

Gly Pro Leu Gly Ser Pro Glu Phe
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic

<400> SEQUENCE: 14

Gly Ile Gly Arg His Lys
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic

<400> SEQUENCE: 15

Asp Pro Leu Val Leu Arg Arg Arg Gln
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Leu Glu His His His His His His
1               5
```

```
<210> SEQ ID NO 17
<211> LENGTH: 15
<212> TYPE: DNA
<213> ORGANISM: Artificial Sequence
<220> FEATURE:
<223> OTHER INFORMATION: synthetic

<400> SEQUENCE: 17
aaaaaaatcg ggaaa                                                        15

<210> SEQ ID NO 18
<211> LENGTH: 43
<212> TYPE: DNA
<213> ORGANISM: Artificial Sequence
<220> FEATURE:
<223> OTHER INFORMATION: synthetic

<400> SEQUENCE: 18
attattatta ttcaaatgga tttatttatt tatttattta ttt                         43

<210> SEQ ID NO 19
<211> LENGTH: 1444
<212> TYPE: DNA
<213> ORGANISM: Homo sapiens

<400> SEQUENCE: 19
ggagaagggg tggggcaggg tatcgctgac tcagcagctt ccaggttgct ctgatgatat        60
attaaggctc ctgaatccta agagaatgtt ggtgaagatc ttaacaccac gccttgagca      120
agtcgcaaga gcgggaggac acagaccagg aaccgagaag ggacaagcac atggaagcca      180
gcccagcatc cgggcccaga cacttgatgg atccacacat attcacttcc aactttaaca      240
atggcattgg aaggcataag acctacctgt gctacgaagt ggagcgcctg acaatggca       300 cctcggtcaa gatggaccag cacaggggct ttctacacaa ccaggctaag aatcttctct      360
gtggctttta cggccgccat gcggagctgc gcttcttgga cctggttcct tctttgcagt      420
tggacccggc ccagatctac agggtcactt ggttcatctc ctggagcccc tgcttctcct      480
ggggctgtgc cggggaagtg cgtgcgttcc ttcaggagaa cacacacgtg agactgcgta      540
tcttcgctgc ccgcatctat gattacgacc ccctatataa ggaggcactg caaatgctgc      600
gggatgctgg ggcccaagtc tccatcatga cctacgatga atttaagcac tgctgggaca      660
cctttgtgga ccaccaggga tgtcccttcc agccctggga tggactagat gagcacagcc      720
aagccctgag tgggaggctg cgggccattc tccagaatca gggaaactga aggatgggcc      780
tcagtctcta aggaaggcag agacctgggt tgagcagcag aataaaagat cttcttccaa      840
gaaatgcaaa cagaccgttc accaccatct ccagctgctc acagacgcca gcaaagcagt      900
atgctcccga tcaagtagat ttttaaaaaa tcagagtggg ccgggcgcgg tggctcacgc      960
ctgtaatccc agcactttgg aggccaaggc gggtggatca cgaggtcagg atcgcgagac     1020
catcctggct aacacggtga aaccctgtct ctactaaaaa tacaaaaaat tagccaggcg     1080
tggtggcggg cgcctgtagt cccagctact ctggaggctg aggcaggaga gtagcgtgaa     1140
cccgggaggc agagcttgcg gtgagccgag attgcgctac tgcactccag cctgggcgac     1200
agtaccagac tccatctcaa aaaaaaaaaa accagactga attaatttta actgaaaatt     1260
tctcttatgt tccaagtaca caatagtaag attatgctca atattctcag aataattttc     1320
aatgtattaa tgaaatgaaa tgataatttg gcttcatatc tagactaaca caaaattaag     1380
```

```
aatcttccat aattgctttt gctcagtaac tgtgtcatga attgcaagag tttccacaaa      1440
cact                                                                   1444

<210> SEQ ID NO 20
<211> LENGTH: 199
<212> TYPE: PRT
<213> ORGANISM: Homo sapiens

<400> SEQUENCE: 20

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 21
<211> LENGTH: 1560
<212> TYPE: DNA
<213> ORGANISM: Homo sapiens

<400> SEQUENCE: 21
cacagagctt caaaaaaaga gcgggacagg gacaagcgta tctaagaggc tgaacatgaa        60
tccacagatc agaaatccga tggagcggat gtatcgagac acattctacg acaactttga      120
aaacgaaccc atcctctatg gtcggagcta cacttggctg tgctatgaag tgaaaataaa      180
gaggggccgc tcaaatctcc tttgggacac agggggtctt tcgaggccag gtgtatttcaa    240 gcctcagtac cacgcagaaa tgtgcttcct ctcttggttc tgtggcaacc agctgcctgc      300
ttacaagtgt ttccagatca cctggtttgt atcctggacc cctgcccgg actgtgtggc      360 gaagctggcc gaattcctgt ctgagcaccc caatgtcacc ctgaccatct ctgccgcccg      420
cctctactac tactgggaaa gagattaccg aagggcgctc tgcaggctga gtcaggcagg      480
agcccgcgtg aagatcatgg actatgaaga atttgcatac tgctgggaaa ctttgtgta      540 caatgaaggt cagcaattca tgccttggta caaattcgat gaaaattatg cattcctgca      600
```

-continued

```
ccgcacgcta aaggagattc tcagatacct gatggatcca gacacattca ctttcaactt      660
taataatgac cctttggtcc ttcgacggcg ccagacctac ttgtgctatg aggtggagcg      720
cctggacaat ggcacctggg tcctgatgga ccagcacatg ggctttctat gcaacgaggc      780
taagaatctt ctctgtggct tttacggccg ccatgcggag ctgcgcttct tggacctggt      840
tccttctttg cagttggacc cggcccagat ctacagggtc acttggttca ctctcctggag    900
ccctgcttc tcctgggct gtgccgggga agtgcgtgcg ttccttcagg agaacacaca       960
cgtgagactg cgcatcttcg ctgcccgcat ctatgattac gaccccctat ataaggaggc     1020
gctgcaaatg ctgcgggatg ctggggccca agtctccatc atgacctacg atgagtttga     1080
gtactgctgg gacacctttg tgtaccgcca gggatgtccc ttccagccct gggatggact     1140
agaggagcac agccaagccc tgagtgggag gctgcgggcc attctccaga atcagggaaa     1200
ctgaaggatg ggcctcagtc tctaaggaag gcagagacct gggttgagca gcagaataaa     1260
agatcttctt ccaagaaatg caaacagacc gttcaccacc atctccagct gctcacagac     1320
accagcaaag caatgtgctc ctgatcaagt agatttttta aaaatcagag tcaattaatt     1380
ttaattgaaa atttctctta tgttccaagt gtacaagagt aagattatgc tcaatattcc     1440
cagaatagtt ttcaatgtat taatgaagtg attaattggc tccatattta gactaataaa     1500
acattaagaa tcttccataa ttgtttccac aaacactaaa aaaaaaaaa aaaaaaaaa      1560

<210> SEQ ID NO 22
<211> LENGTH: 382
<212> TYPE: PRT
<213> ORGANISM: Homo sapiens

<400> SEQUENCE: 22

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Lys Pro Gln
        50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205
```

```
Leu Arg Arg Arg Gln Thr Tyr Leu Cys Tyr Glu Val Glu Arg Leu Asp
210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
            245                 250                 255

Arg Phe Leu Asp Leu Val Pro Ser Leu Gln Leu Asp Pro Ala Gln Ile
        260                 265                 270

Tyr Arg Val Thr Trp Phe Ile Ser Trp Ser Pro Cys Phe Ser Trp Gly
    275                 280                 285

Cys Ala Gly Glu Val Arg Ala Phe Leu Gln Glu Asn Thr His Val Arg
290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
            325                 330                 335

Thr Tyr Asp Glu Phe Glu Tyr Cys Trp Asp Thr Phe Val Tyr Arg Gln
        340                 345                 350

Gly Cys Pro Phe Gln Pro Trp Asp Gly Leu Glu Glu His Ser Gln Ala
    355                 360                 365

Leu Ser Gly Arg Leu Arg Ala Ile Leu Gln Asn Gln Gly Asn
370                 375                 380
```

<210> SEQ ID NO 23
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 23
attattatta tacaaatgga tttatttatt tatttattta ttt          43

<210> SEQ ID NO 24
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 24
attattatta tccaaatgga tttatttatt tatttattta ttt          43

<210> SEQ ID NO 25
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 25
attattatta tgcaaatgga tttatttatt tatttattta ttt          43

<210> SEQ ID NO 26
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 26
attattatta ttcaaatgga tttatttatt tatttattta ttt                43

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (12)..(14)
<223> OTHER INFORMATION: 5-nitroindole

<400> SEQUENCE: 27
aaaaaaaaat cnnnaaaaaa a                                        21

<210> SEQ ID NO 28
<211> LENGTH: 51
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 28
gtagttagta ggattgattg agnnnncnnn tgattgatgg attgagtagt g        51

<210> SEQ ID NO 29
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 29
aatgatacgg cgaccaccga gatctacact ctttccctac acgacgctct tccgatctta    60
gttagtagga ttgattgag                                                79

<210> SEQ ID NO 30
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 30
caagcagaag acggcatacg agatattggc gtgactggag ttcagacgtg tgctcttccg    60
atctcactac tcaatccatc aatca                                         85

<210> SEQ ID NO 31
<211> LENGTH: 85
<212> TYPE: DNA
<213> ORGANISM: Artificial Sequence
<220> FEATURE:
<223> OTHER INFORMATION: synthetic oligonucleotide

```
<400> SEQUENCE: 31
caagcagaag acggcatacg agatttgact gtgactggag ttcagacgtg tgctcttccg    60
atctcactac tcaatccatc aatca                                          85

<210> SEQ ID NO 32
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 32
caagcagaag acggcatacg agattacaag gtgactggag ttcagacgtg tgctcttccg    60
atctcactac tcaatccatc aatca                                          85

<210> SEQ ID NO 33
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 33
caagcagaag acggcatacg agatggaact gtgactggag ttcagacgtg tgctcttccg    60
atctcactac tcaatccatc aatca                                          85

<210> SEQ ID NO 34
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 34
caagcagaag acggcatacg agatcactgt gtgactggag ttcagacgtg tgctcttccg    60
atctcactac tcaatccatc aatca                                          85

<210> SEQ ID NO 35
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 35
caagcagaag acggcatacg agattgacat gtgactggag ttcagacgtg tgctcttccg    60
atctcactac tcaatccatc aatca                                          85

<210> SEQ ID NO 36
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 36
caagcagaag acggcatacg agattttcac gtgactggag ttcagacgtg tgctcttccg    60
atctcactac tcaatccatc aatca                                          85
```

```
<210> SEQ ID NO 37
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 37
caagcagaag acggcatacg agatcgaaac gtgactggag ttcagacgtg tgctcttccg    60
atctcactac tcaatccatc aatca                                         85

<210> SEQ ID NO 38
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 38
caagcagaag acggcatacg agatcgtgat gtgactggag ttcagacgtg tgctcttccg    60
atctcactac tcaatccatc aatca                                         85

<210> SEQ ID NO 39
<211> LENGTH: 85
<212> TYPE: DNA
<213> ORGANISM: Artificial Sequence
<220> FEATURE:
<223> OTHER INFORMATION: synthetic oligonucleotide

<400> SEQUENCE: 39
caagcagaag acggcatacg agataagcta gtgactggag ttcagacgtg tgctcttccg    60
atctcactac tcaatccatc aatca                                         85

<210> SEQ ID NO 40
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 40
cactactcaa tccatcaatc a                                             21

<210> SEQ ID NO 41
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 41
cattggaagg cataaggcct acctgtgcta cg                                 32

<210> SEQ ID NO 42
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 42
cgtagcacag gtaggcctta tgccttccaa tg                                 32
```

<210> SEQ ID NO 43
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 43
ggcattggaa ggcataagga ctacctgtgc tacgaagtg                          39

<210> SEQ ID NO 44
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 44
cacttcgtag cacaggtagt ccttatgcct tccaatgcc                          39

<210> SEQ ID NO 45
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 45
ttacggccgc catggggagc tgcgcttc                                      28

<210> SEQ ID NO 46
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 46
gaagcgcagc tccccatggc ggccgtaa                                      28

<210> SEQ ID NO 47
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 47
ttacggccgc catccggagc tgcgcttc                                      28

<210> SEQ ID NO 48
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 48
aagcgcagct ccggatggcg gccgtaa                                       27

<210> SEQ ID NO 49
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 49
tggttcatct ccgcgagccc ctgcttc 27

<210> SEQ ID NO 50
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 50
gaagcagggg ctcgcggaga tgaacca 27

<210> SEQ ID NO 51
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 51
tggttcatct ccttcagccc ctgcttc 27

<210> SEQ ID NO 52
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 52
gaagcagggg ctgaaggaga tgaacca 27

<210> SEQ ID NO 53
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 53
tggttcatct cctacagccc ctgcttc 27

<210> SEQ ID NO 54
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 54
gaagcagggg ctgtaggaga tgaacca 27

<210> SEQ ID NO 55
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 55
gttcatctcc tggggcccct gcttctcc 28

```
<210> SEQ ID NO 56
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 56
ggagaagcag gggccccagg agatgaac                                              28

<210> SEQ ID NO 57
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 57
gttcatctcc tggccaccct gcttctcc                                              28

<210> SEQ ID NO 58
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 58
ggagaagcag ggtggccagg agatgaac                                              28

<210> SEQ ID NO 59
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 59
gctgcccgca tctttgatta cgacccc                                               27

<210> SEQ ID NO 60
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 60
ggggtcgtaa tcaaagatgc gggcagc                                               27

<210> SEQ ID NO 61
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 61
gctgcccgca tcgctgatta cgacccc                                               27

<210> SEQ ID NO 62
<211> LENGTH: 27
<212> TYPE: DNA
<213> ORGANISM: Artificial Sequence
<220> FEATURE:
<223> OTHER INFORMATION: synthetic oligonucleotide
```

```
<400> SEQUENCE: 62
ggggtcgtaa tcagcgatgc gggcagc                                              27

<210> SEQ ID NO 63
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 63
gcccgcatct atgagtacga cccccta                                              27

<210> SEQ ID NO 64
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 64 taggggtcg tactcataga tgcgggc                                               27

<210> SEQ ID NO 65
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 65
gcccgcatct atgcttacga cccccta                                              27

<210> SEQ ID NO 66
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 66 taggggtcg taagcataga tgcgggc                                               27

<210> SEQ ID NO 67
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 67
gcccgcatct atacttacga cccccta                                              27

<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68 taggggtcg taagtataga tgcgggc                                               27
```

<210> SEQ ID NO 69
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 69
cgcatctatg atttcgaccc cctatat                                            27

<210> SEQ ID NO 70
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 70
atataggggg tcgaaatcat agatgcg                                            27

<210> SEQ ID NO 71
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 71
cgcatctatg atgccgaccc cctatat                                            27

<210> SEQ ID NO 72
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 72
atataggggg tcggcatcat agatgcg                                            27

<210> SEQ ID NO 73
<211> LENGTH: 1368
<212> TYPE: PRT
<213> ORGANISM: Artificial Sequence
<220> FEATURE:
<223> OTHER INFORMATION: synthetic polypeptide

<400> SEQUENCE: 73

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

-continued

```
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Gly Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
```

-continued

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335
```

-continued

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 74
<211> LENGTH: 1368
<212> TYPE: PRT
<213> ORGANISM: Artificial Sequence
<220> FEATURE:
<223> OTHER INFORMATION: synthetic polypeptide

<400> SEQUENCE: 74

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

-continued

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Gly Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

```
Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

<210> SEQ ID NO 75
<211> LENGTH: 9
<212> TYPE: PRT
<213> ORGANISM: Artificial Sequence
<220> FEATURE:
<223> OTHER INFORMATION: consensus

<400> SEQUENCE: 75

Leu Ala Gly Leu Ile Asp Ala Asp Gly
1               5
```

SITE-SPECIFIC DNA BASE EDITING USING MODIFIED APOBEC ENZYMES

CROSS-REFERENCE TO RELATED APPLICATIONS

This application claims benefit of priority from U.S. Provisional Application Ser. No. 62/431,703, filed on Dec. 8, 2016.

STATEMENT AS TO FEDERALLY SPONSORED RESEARCH

This invention was made with government support under GM118000, GM110129, CA206309, GM118047, OD007237, GM103426 awarded by the National Institutes of Health, and CHE060073N awarded by the National Science Foundation. The government has certain rights in the invention.

SEQUENCE LISTING

This document includes a sequence listing that was submitted to the United States Patent and Trademark Office via the electronic filing system as an ASCII text file. The sequence listing, which is incorporated-by-reference herein, is titled "seq.txt," was created on Dec. 29, 2017, and has a size of 79,543 bytes.

TECHNICAL FIELD

This document relates to materials and methods for targeted modification of specific DNA sequences, and more specifically to materials and methods for using fusion polypeptides, such as modified Cas9-APOBEC fusion polypeptides, for modification of DNA nucleobases in a targeted, site-specific manner.

BACKGROUND

Vertebrates encode variable numbers of active polynucleotide cytosine deaminase enzymes that collectively are called apolipoprotein B mRNA-editing complex (APOBEC) proteins (Conticello, *Genome Biol* 9:229, 2008; and Harris and Dudley, *Virology* 479-480C: 131-145, 2015). These enzymes catalyze hydrolytic deamination of cytidine or deoxycytidine in polynucleotides to uridine or deoxyuridine, respectively. All vertebrate species have activation-induced deaminase (AID), which is essential for antibody gene diversification through somatic hypermutation and class switch recombination (Di Noia and Neuberger, *Annu Rev Biochem* 76:1-22, 2007; and Robbiani and Nussenzweig, *Annu Rev Pathol* 8:79-103, 2013). Most vertebrates also have APOBEC1, which edits cytosine nucleobases in RNA and single-stranded DNA (ssDNA), and functions in regulating the transcriptome and likely also in blocking the spread of endogenous and exogenous mobile elements such as viruses (Fossat and Tam, *RNA Biol* 11:1233-1237, 2014; and Koito and Ikeda, *Front Microbiol* 4:28, 2013). The APOBEC3 subfamily of enzymes is specific to mammals, subject to extreme copy number variation, elicits strong preferences for ssDNA, and provides innate immune protection against a wide variety of DNA-based parasites, including common retrotransposons L1 and Alu, and retroviruses such as HIV-1 (Harris and Dudley, supra; Malim and Bieniasz, *Cold Spring Harb Perspect Med* 2:a006940, 2012; and Simon et al., *Nat Immunol* 16:546-553, 2015). Human cells have the potential to produce up to seven distinct APOBEC3 enzymes, APOBEC3A through APOBEC3H (A3A-A3H, excluding A3E), although most cells express subsets due to differential gene regulation (Refsland et al., *Nucleic Acids Res* 38:4274-4284, 2010; Koning et al., *J Virol* 83:9474-9485, 2009; Stenglein et al., *Nat Struct Mol Biol* 17:222-229, 2010; and Burns et al., *Nature* 494:366-370, 2013a).

SUMMARY

This document is based, at least in part, on the elucidation of a molecular mechanism underlying ssDNA binding activity and local target selectivity of APOBEC enzymes. The experimental results described herein, including the crystal structures of human A3A and a variant of the human A3B catalytic domain in complex with ssDNA substrates, together with supporting biochemical data and comparisons with apo-structures described elsewhere, provide robust molecular explanations as to why the APOBEC enzymes selectively bind ssDNA and elicit strong preferences for cytosine nucleobases in specific 5'-TC contexts in viral and cancer genomes. This discovery allows for the design of variant APOBEC molecules that, together with a targeting system such as a Clustered Regularly Interspersed Short Palindromic Repeats/CRISPR-associated (CRISPR/Cas) system, can be used to modify DNA in a specific, targeted fashion.

In one aspect, this document features a polypeptide comprising (a) a first portion containing an APOBEC polypeptide that has deaminase activity, wherein the APOBEC polypeptide includes an amino acid sequence that is at least 90% identical to the amino acid sequence set forth in SEQ ID NO:20, with the proviso that the polypeptide lacks amino acids 1-12 of SEQ ID NO:20, amino acids 196-199 of SEQ ID NO:20, or amino acids 1-12 and 196-199 of SEQ ID NO:20; and (b) a second portion containing a Cas9 polypeptide having the ability to complex with a CRISPR RNA (crRNA), but lacking nuclease activity. The APOBEC polypeptide can be fused to the N-terminus of the Cas9 polypeptide, or to the C-terminus of the Cas9 polypeptide. The APOBEC polypeptide can be inserted into an inner loop of the Cas9 polypeptide. The APOBEC polypeptide can be coupled to the Cas9 polypeptide via a linker. The fusion polypeptide can include a third portion that contains an additional functional domain (e.g., a functional domain from an inhibitor of uracil DNA glycosylase). In some embodiments, the APOBEC polypeptide amino acid residue at the position corresponding to position 131 of SEQ ID NO:20 is not aspartate. The APOBEC polypeptide amino acid residue at the position corresponding to position 131 of SEQ ID NO:20 can be glutamate or threonine. The APOBEC polypeptide can have an amino acid sequence that is at least 95% identical to the amino acid sequence set forth in SEQ ID NO:20, or at least 98% identical to the amino acid sequence set forth in SEQ ID NO:20. The Cas9 polypeptide can contain an inactive Cas9 nuclease domain and a Cas9 gRNA binding domain. The inactive Cas9 nuclease domain can include a mutation at the position corresponding to position 10 of a *Streptococcus pyogenes* Cas9 protein having the sequence set forth in SEQ ID NO:8, a mutation at the position corresponding to position 840 of a *S. pyogenes* Cas9 protein having the sequence set forth in SEQ ID NO:8, or mutations at the positions corresponding to positions 10 and 840 of a *S. pyogenes* Cas9 protein having the sequence set forth in SEQ ID NO:8. The Cas9 nuclease domain can have nickase activity. The Cas9 polypeptide can include a Cas9 gRNA binding domain, without a Cas9 nuclease domain.

In another aspect, this document features a polypeptide containing (a) a first portion that contains an APOBEC polypeptide that has deaminase activity, wherein the APOBEC polypeptide includes an amino acid sequence that is at least 90% identical to the amino acid sequence set forth in SEQ ID NO:22, with the proviso that the polypeptide lacks amino acids 1-192 of SEQ ID NO:20, or amino acids 1-192 and 379-382 of SEQ ID NO:22; and (b) a second portion containing a Cas9 polypeptide having the ability to complex with a crRNA, but lacking nuclease activity. The APOBEC polypeptide can be fused to the N-terminus of the Cas9 polypeptide, or to the C-terminus of the Cas9 polypeptide. The APOBEC polypeptide can be inserted into an inner loop of the Cas9 polypeptide. The APOBEC polypeptide can be coupled to the Cas9 polypeptide via a linker. The fusion polypeptide can include a third portion that contains an additional functional domain (e.g., a functional domain from an inhibitor of uracil DNA glycosylase). In some embodiments, the APOBEC polypeptide amino acid residue at the position corresponding to position 314 of SEQ ID NO:22 is not aspartate. The APOBEC polypeptide amino acid residue at the position corresponding to position 314 of SEQ ID NO:22 can be glutamate or threonine. The APOBEC polypeptide can have an amino acid sequence that is at least 95% identical to the amino acid sequence set forth in SEQ ID NO:22, or at least 98% identical to the amino acid sequence set forth in SEQ ID NO:22. The Cas9 polypeptide can contain an inactive Cas9 nuclease domain and a Cas9 gRNA binding domain. The inactive Cas9 nuclease domain can include a mutation at the position corresponding to position 10 of a *Streptococcus pyogenes* Cas9 protein having the sequence set forth in SEQ ID NO:8, a mutation at the position corresponding to position 840 of a *S. pyogenes* Cas9 protein having the sequence set forth in SEQ ID NO:8, or mutations at the positions corresponding to positions 10 and 840 of a *S. pyogenes* Cas9 protein having the sequence set forth in SEQ ID NO:8. The Cas9 nuclease domain can have nickase activity. The Cas9 polypeptide can include a Cas9 gRNA binding domain, without a Cas9 nuclease domain.

In another aspect, this document features a nucleic acid molecule encoding a polypeptide as disclosed herein. The nucleic acid molecule can further contain (i) a sequence encoding a crRNA and a sequence encoding a trans-activating crRNA (tracrRNA), or (ii) a sequence encoding a crRNA/tracrRNA hybrid (gRNA).

In another aspect, this document features a method for targeted modification of a selected DNA sequence, where the method includes contacting the DNA sequence with (a) a fusion polypeptide that contains (i) a first portion containing an APOBEC polypeptide that has deaminase activity, wherein the APOBEC polypeptide includes an amino acid sequence that is at least 90% identical to the amino acid sequence set forth in SEQ ID NO:20, with the proviso that the polypeptide lacks amino acids 1-12 of SEQ ID NO:20, amino acids 196-199 of SEQ ID NO:20, or amino acids 1-12 and 196-199 of SEQ ID NO:20, and (ii) a second portion containing a Cas9 polypeptide having the ability to complex with a crRNA, but lacking nuclease activity, and (b) a nucleic acid comprising a crRNA sequence and a tracrRNA sequence targeted to the selected sequence, such that the nucleic acid complexes with the fusion polypeptide and directs the fusion polypeptide to the selected sequence, wherein the method includes contacting the DNA sequence with the fusion polypeptide and the nucleic acid in an amount effective for deamination of a deoxycytidine within the selected DNA sequence. The APOBEC polypeptide can be fused to the N-terminus of the Cas9 polypeptide, or to the C-terminus of the Cas9 polypeptide. The APOBEC polypeptide can be inserted into an inner loop of the Cas9 polypeptide. The APOBEC polypeptide can be coupled to the Cas9 polypeptide via a linker. The fusion polypeptide can contain a third portion that includes an additional functional domain (e.g., a functional domain is from an inhibitor of uracil DNA glycosylase). In some embodiments, the APOBEC polypeptide amino acid residue at the position corresponding to position 131 of SEQ ID NO:20 is not aspartate. The APOBEC polypeptide amino acid residue at the position corresponding to position 131 of SEQ ID NO:20 can be glutamate or threonine. The APOBEC polypeptide can have an amino acid sequence that is at least 95% identical to the amino acid sequence set forth in SEQ ID NO:20, or at least 98% identical to the amino acid sequence set forth in SEQ ID NO:20. The Cas9 polypeptide can include an inactive Cas9 nuclease domain and a Cas9 gRNA binding domain. The inactive Cas9 nuclease domain can have a mutation at the position corresponding to position 10 of a *Streptococcus pyogenes* Cas9 protein having the sequence set forth in SEQ ID NO:8, a mutation at the position corresponding to position 840 of a *S. pyogenes* Cas9 protein having the sequence set forth in SEQ ID NO:8, or mutations at the positions corresponding to positions 10 and 840 of a *S. pyogenes* Cas9 protein having the sequence set forth in SEQ ID NO:8. The Cas9 nuclease domain can have nickase activity. The Cas9 polypeptide can include a Cas9 gRNA binding domain, without including a Cas9 nuclease domain. The introducing can include introducing into the cell a nucleic acid encoding the fusion polypeptide, and the method can further include maintaining the cell under conditions in which the nucleic acid encoding the fusion polypeptide is expressed. The nucleic acid encoding the fusion polypeptide can be operably linked to a constitutive promoter or an inducible promoter. The nucleic acid encoding the fusion polypeptide and the nucleic acid containing the crRNA sequence and the tracrRNA sequence can be present in a single vector or in separate vectors. The crRNA sequence and the tracrRNA sequence can be contained within a gRNA sequence. The tracrRNA sequence and the crRNA sequence can be operably linked to a constitutive promoter or an inducible promoter. The contacting can be in vitro. The selected DNA sequence can be associated with a clinical condition, and deamination of the cytidine can result in a sequence that is not associated with the clinical condition. The contacting can be in vivo in a subject identified as having the clinical condition. The method can further include detecting deamination of the cytidine. The detecting can include polymerase chain reaction and DNA sequencing.

In still another aspect, this document features a method for targeted modification of a selected DNA sequence, where the method includes contacting the DNA sequence with (a) a fusion polypeptide that contains (i) a first portion containing an APOBEC polypeptide that has deaminase activity, wherein the APOBEC polypeptide includes an amino acid sequence that is at least 90% identical to the amino acid sequence set forth in SEQ ID NO:22, with the proviso that the polypeptide lacks amino acids 1-192 of SEQ ID NO:22, or amino acids 1-192 and 379-382 of SEQ ID NO:22, and (ii) a second portion containing a Cas9 polypeptide having the ability to complex with a crRNA, but lacking nuclease activity, and (b) a nucleic acid containing a crRNA sequence and a tracrRNA sequence targeted to the selected sequence, such that the nucleic acid complexes with the fusion polypeptide and directs the fusion polypeptide to the selected sequence, where the method includes contacting the DNA sequence with the fusion polypeptide and the nucleic acid in an amount effective for deamination of a deoxycytidine within the selected DNA sequence. The APOBEC polypeptide can be fused to the N-terminus of the Cas9 polypeptide, or to the C-terminus of the Cas9 polypeptide. The APOBEC polypeptide can be inserted into an inner loop of the Cas9 polypeptide. The APOBEC polypeptide can be coupled to the Cas9 polypeptide via a linker. The fusion polypeptide can contain a third portion that includes an additional functional domain (e.g., a functional domain is from an inhibitor of uracil DNA glycosylase). In some embodiments, the APOBEC polypeptide amino acid residue at the position corresponding to position 314 of SEQ ID NO:22 is not aspartate. The APOBEC polypeptide amino acid residue at the position corresponding to position 314 of SEQ ID NO:22 can be glutamate or threonine. The APOBEC polypeptide can have an amino acid sequence that is at least 95% identical to the amino acid sequence set forth in SEQ ID NO:22, or at least 98% identical to the amino acid sequence set forth in SEQ ID NO:22. The Cas9 polypeptide can include an inactive Cas9 nuclease domain and a Cas9 gRNA binding domain. The inactive Cas9 nuclease domain can have a mutation at the position corresponding to position 10 of a *Streptococcus pyogenes* Cas9 protein having the sequence set forth in SEQ ID NO:8, a mutation at the position corresponding to position 840 of a *S. pyogenes* Cas9 protein having the sequence set forth in SEQ ID NO:8, or mutations at the positions corresponding to positions 10 and 840 of a *S. pyogenes* Cas9 protein having the sequence set forth in SEQ ID NO:8. The Cas9 nuclease domain can have nickase activity. The Cas9 polypeptide can include a Cas9 gRNA binding domain, without including a Cas9 nuclease domain. The introducing can include introducing into the cell a nucleic acid encoding the fusion polypeptide, and the method can further include maintaining the cell under conditions in which the nucleic acid encoding the fusion polypeptide is expressed. The nucleic acid encoding the fusion polypeptide can be operably linked to a constitutive promoter or an inducible promoter. The nucleic acid encoding the fusion polypeptide and the nucleic acid containing the crRNA sequence and the tracrRNA sequence can be present in a single vector or in separate vectors. The crRNA sequence and the tracrRNA sequence can be contained within a gRNA sequence. The tracrRNA sequence and the crRNA sequence can be operably linked to a constitutive promoter or an inducible promoter. The contacting can be in vitro. The selected DNA sequence can be associated with a clinical condition, and deamination of the cytidine can result in a sequence that is not associated with the clinical condition. The contacting can be in vivo in a subject identified as having the clinical condition. The method can further include detecting deamination of the cytidine. The detecting can include polymerase chain reaction and DNA sequencing.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a Clustal Omega alignment of amino acids 13-199 of human A3A (SEQ ID NO:1) and amino acids 193-382 of human APOBEC3B (A3B) (SEQ ID NO:2, the C-terminal catalytic domain) showing secondary structures (α-helices in white boxes, β-strands in gray boxes) and loop regions. Bold font indicates amino acids that were altered to obtain soluble proteins for structural studies and, in the case of the catalytic glutamate, to prevent genotoxicity to *E. coli* during protein expression and substrate turnover during crystallization. The aspartic acid residue at position 131 of the full length A3A protein (position 119 within SEQ ID NO:1) and position 314 of the full length A3B protein (position 122 within SEQ ID NO:2), which is thought to be a determinant of APOBEC target specificity based on the experiments described herein, is circled.

FIGS. 3A-3C are additional representations of A3A-ssDNA complexes. FIG. 3A is an overlay of the four distinct A3A-ssDNA complexes in the asymmetric unit of the crystal. FIG. 3B is a composite omit 2Fo-Fc map contoured at 1.0σ for the four complexes in the asymmetric unit (protein electron density is shown in green, and ssDNA in blue). FIG. 3C is an enlarged view of the composite omit 2Fo-Fc map contoured at 1.0σ (blue mesh) for the ssDNA oligonucleotides bound in the four distinct A3A molecules (differently colored) captured in the asymmetric unit of the crystal. The orange mesh (composite omit 2Fo-Fc map contoured at 8.0σ) represents the position of the single zinc atom (gray sphere shown at 0.6× scale of the van der Waals radius).

FIG. 4A is a ribbon schematic of an A3A-ssDNA complex showing flipped-out target C and −1 T nucleotides, as well as the overall U-shaped binding conformation. FIG. 4B shows the molecular surface of the A3A active site with the surrounding loops color-coded, and a superposition of stick-models of ssDNA bound to four different molecules in the crystal's asymmetric unit. FIG. 4C is a view similar to that shown in FIG. 4B, with a representative ssDNA molecule shown and nucleobases and key amino side chains from the active site loops labeled. FIG. 4D is a wall-eye stereo view of the A3A active site and the bound ssDNA molecule shown in sticks. Hydrogen bonds are indicated by yellow dashed lines.

FIGS. 5A-5F show the crystal structure of a variant of the human A3B catalytic domain bound to ssDNA with a 5'-TCA deamination target motif. FIG. 5A is a ribbon schematic of a ssDNA-A3Bctd-QMΔloop3-A3Aloop1-E255A (hereinafter called A3Bctd*) complex, showing the flipped-out target C(0) and −1 T, as well as the overall U-shaped binding conformation. FIG. 5B is a superposition of the active site region of A3A (cyan) and A3Bctd* (magenta) with relevant ssDNA substrates (opaque from a representative A3A structure and yellow from the A3Bctd* structure) showing the near-identical positioning of the flipped-out target C and −1 T. FIGS. 5C and 5D are composite omit 2Fo-Fc maps contoured at 1.0σ, shown for the region surrounding the target cytosine (FIG. 5C) or the −1 thymine (FIG. 5D). FIG. 5E is a picture of a gel indicating deaminase activity of wild-type A3A on ssDNA substrates containing normal T or the indicated analogs at the −1 position (SEQ ID NOS: 3, 4, 5, and 6), demonstrating that the 5-methyl group is unconstrained structurally. Uracil DNA glycosylase (UDG) readily excised dU and 5FdU from ssDNA and accounted for the 11-nucleotide product in the absence of deamination. However, due to A3A activity on the target C and the 3'-end label, only the shorter 10-nucleotide product was apparent upon deamination and gel fractionation. The results are representative of two independent experiments. FIG. 5F is a wall-eye stereo view of the A3Bctd* active site and the bound ssDNA molecule shown in sticks. Hydrogen bonds are indicated by yellow dashed lines. Water molecules are represented by small red crosshairs.

FIG. 6A shows the composite omit 2Fo-Fc map for the single A3Bctd*-ssDNA complex contoured at 1.0σ in the asymmetric unit (electron density for protein and ssDNA is shown in green and blue, respectively). FIG. 6B is an enlarged view of the composite omit 2Fo-Fc map contoured at 1.0σ (blue mesh) for the ssDNA oligonucleotide (yellow sticks) bound to the active site of A3B (magenta). The orange mesh (composite omit 2Fo-Fc map contoured at 8.0σ) represents the position of the single zinc atom (gray sphere, shown at 0.6× scale of the van der Waals radius).

FIGS. 7A-7E demonstrate that human A3A deaminates ssDNA containing −1 Super T. FIG. 7A shows the letter format of the single-stranded DNA sequence modeled in FIGS. 7B and 7C with 5-hydroxybutynl-2'-deoxyuridine (Super T; Integrated DNA Technologies, Coralville, Iowa) at the −1 position relative to the target cytidine. FIG. 7B shows chemical structures of normal deoxy-thymidine and Super T differing only at the 5 position of the cytosine ring. FIG. 7C shows the predicted conformation of ssDNA containing −1 Super T bound to human A3A. A semi-transparent molecular surface is shown for the protein. FIG. 7D is the raw dose response data for human A3A and ssDNA substrates with a normal T or Super T at the −1 position relative to the target cytosine (0.1-100 nM A3A with 100 nM A3A-E72A and no enzyme reactions shown as negative controls). The wild-type A3A data are identical to those in FIG. 8 to facilitate cross-comparisons. FIG. 7E is a plot quantifying product accumulation for the experiment shown in FIG. 7D. These data indicated that the methyl group at the 5-position of the thymine ring is solvent exposed and unlikely to be involved in an interaction with the enzyme.

FIG. 8A is schematic showing a ssDNA substrate containing an optimal A3A target site (5'-ATCGGG) within a longer sequence (SEQ ID NO:3) and a derivative substrate with 5-nitroindole bases substituted at the +1 to +3 positions. FIG. 8B shows representative endpoint data for human A3A, showing catalytic activity with normal or 5-nitroindole substituted ssDNA substrates (S, substrate; P, product). FIG. 8C is a raw dose response data for human A3A and ssDNA substrates with normal GGG or XXX at the +1 to +3 positions relative to the target cytosine (0.1-100 nM A3A with 100 nM A3A-E72A and no enzyme reactions shown as a negative controls). The wild-type A3A data are identical to those in FIG. 7 to facilitate cross-comparisons. FIG. 8D is a Bplot quantifying product accumulation for the experiment shown in FIG. 8C. A3A showed a modest 2-fold preference for normal ssDNA substrate in comparison to the 5-nitroindole substituted ssDNA substrate. The data in FIGS. 8B-8D combine to suggest that base stacking of the +1 to +3 nucleotides may be more relevant for the ssDNA deamination mechanism than nucleobase hydrogen-bonding with enzyme.

FIGS. 9A and 9B show the molecular surface of A3A around the active site in the DNA-free (FIG. 9A, RCSB Protein Data Bank (pdb) ref. 4XXO) and ssDNA-bound (FIG. 9B, pdb ref. 5SWW) states, showing re-orientation of the side chains of His29 and Tyr132. FIG. 9C is a superposition of the two conformations in FIGS. 9A and 9B, highlighting the repositioning of His29 and Tyr132 as well as shifting of loop 3 toward the bound ssDNA. FIGS. 9D and 9E show the molecular surface of A3Bctd* around the active site in the DNA-free (FIG. 9D, pdb ref 5CQH) and ssDNA-bound (FIG. 9E, pdb ref. 5TD5) states showing the large transition that is likely to occur between the closed (unbound) and open (ssDNA-bound) conformations.

FIGS. 10A and 10B show DNA cytosine deamination by human A3A (WT, wild-type) and the indicated mutant derivatives (S, substrate; P, product). The corresponding anti-MYC (A3A) and anti-TUBULIN immunoblots indicated similar levels of A3A and soluble extract in each experiment relative to controls (A3A has two bands due to alternative translation initiation from Met1 or Met13). Reactions in FIG. 10A interrogated active site mutants using a 43-nucleotide 5'-TC-containing ssDNA substrate, and reactions in FIG. 10B additionally interrogated the identity of the −1 position (A, C, G, or T) relative to the target cytosine. The results are representative of two independent experiments. FIG. 10C is a series of graphs quantifying product accumulation in dose response experiments for A3A and the indicated D131 derivatives using the same ssDNA substrates as FIG. 10B. WT enzyme and D131T showed similar activities and local −1 nucleobase preferences, D131A had low activity and relaxed preferences, and D131E had slightly lower activity and a clear preference for −1 C instead of −1 T. These data are representative of two independent experiments. Source data are provided in TABLE 2.

FIG. 11 is a diagram indicating hydrogen bond interactions between amino acids at positions 131 and 132 of A3A and thymine (left) or cytosine (right). The substitution of the longer glutamate for aspartate (D131E) may convert the preference at the −1 position from T to C by creating an opportunity for direct hydrogen-bonding with the amino group of the cytosine ring and simultaneously disrupting the hydrogen-bonding between carboxyl group of the shorter aspartate side chain and the N3 hydrogen of thymine.

FIGS. 12A and 12B show that human A3A and *S. aureus* TadA have similar U-shaped polynucleotide binding conformations. FIG. 12A is a ribbon schematic of A3A-ssDNA (pdb ref 5SWW) and TadA-tRNA (pdb ref. 2B3J; Losey et al., *Nat Struct Mol Biol* 13:153-159, 2006), with the single zinc-coordinating active site regions positioned at similar angles for comparison. FIG. 12B is a superposition of A3A-ssDNA and TadA-tRNA structures, showing similar U-shaped binding conformations. A3A-bound ssDNA is shown in yellow and TadA-bound RNA is shown with an orange backbone and magenta nucleobases.

FIG. 13A shows ribbon schematics of A3A-ssDNA (pdb ref 5SWW) and A3Gntd-poly dT (pdb ref. 5K83) with active site regions positioned at similar angles to facilitate comparisons. FIG. 13B shows a superposition of A3A-ssDNA and A3Gntd-poly dT structures, showing a lack of congruency in the binding conformations. A3A-bound ssDNA is shown in yellow.

FIGS. 14A and 14B are APOBEC3 subfamily superpositions. FIG. 14A is a superposition of ribbon schematics of crystal structures for A3A in cyan (pdb ref. 4XXO), A3Bctd in magenta (pdb ref. 5CQH), A3C in yellow (pdb ref. 3VOW), A3Fctd in gray and green (pdb refs. 5HX5 and 3WUS), and A3Gctd in salmon (pdb ref. 3V4K). FIG. 14B is a superposition of key active site amino acid residues. The zinc-coordinating residues and those that line the active site, including the Trp-Ser-Pro-Cys-$X_{2-4}$-Cys motif and A3A Thr31 (A3B Thr214) that directly interact with the target cytosine, show high structural conservation. In contrast, A3A Tyr130 (A3B Tyr313) from loop 7 and A3A Asn57 (A3B Asn240) preceding loop 3, which both make critical ssDNA backbone contacts, can adopt more variable conformations.

FIGS. 15A-15E show a structural comparison of the active sites of A3B and distantly related deaminase family members. Active sites of A3Bctd bound to ssDNA (FIG. 15A), T4 bacteriophage 2'-deoxycytidylate deaminase bound to a dCMP analog (pdb ref. 1VQ2 (Almog et al., *Biochemistry* 43:13715-13723, 2004); FIG. 15B), murine cytidine deaminase bound to cytidine (pdb ref. 2FR6 (Teh et al., *Biochemistry* 45:7825-7833, 2006); FIG. 15C), and yeast cytosine deaminase bound to an analog of the free nucleobase cytosine (pdb ref 1P6O (Ireton et al., *Structure* 11:961-972, 2003); FIG. 15D) are shown. The catalytic glutamate (Glu255) was modeled into the A3Bctd*-ssDNA structure based on its positioning in the apo structure (pdb ref 5CQH), closely mimicking conformations of the corresponding residues in the T4, mouse, and yeast enzymes (Glu106, Glu67, and Glu64, respectively). Gray spheres represent zinc ions. Smaller red spheres show the zinc-bound reactive water molecule. Sticks depict key residues contacting bound substrates, and ribbons represent protein backbones. The magenta loop in FIG. 15C is from an adjacent subunit in the tetramer. A comparison of the structures shows similar zinc-coordination mechanisms and target cytosine positioning including conservation of surrounding aromatic residues, as well as substrate-specific interactions conferred by unique residues for each class of enzyme. FIG. 15E depicts a potential deamination mechanism (adapted from Ko et al., *J Biol Chem* 278:19111-19117, 2003): (i) Glu255 deprotonates the Zn2+-coordinated $H_2O$ for nucleophilic attack at cytosine with the residual, protonated Glu255 H-bonding to N3 to withdraw electron density from C4 of cytosine, thereby accelerating nucleophilic attack by hydroxide. (ii) Deprotonation of the alcohol on the tetrahedral intermediate by Glu255 ensues, followed by (iii) collapse of the tetrahedral intermediates due to elimination of ammonia, to which protonated Glu255 contributes a hydrogen. (iv) The resulting uracil base is likely stabilized by Zn2+ coordination in the enzyme active site.

FIG. 16A is a histogram graph plotting the deaminase activity in soluble extracts from 293T cells expressing empty vector (EV), wild-type human A3A (A3A), human A3A-E72A (A3Am), or human A3A with loop 7 replaced with the analogous A3G residues (A3AL7). The ssDNA substrates included a 5'-CC target or a 5'-TC target. Activity assays were conducted according to procedures described elsewhere (Rathore et al., *J Mol Biol* 425:4442-4454, 2013; Carpenter et al., *J Biol Chem* 287:34801-34808, 2012; and Li et al., *ACS Chem Biol* 7(3):506-517, 2012). FIGS. 16B-16D contain data from a foreign DNA mutation experiment in which the indicated constructs, empty vector (EV), wild-type human A3A (A3A), human A3A-E72A (A3Am), or human A3A with loop 7 replaced with the analogous A3G residues (A3AL7), were transfected into 293T cells with a GFP reporter plasmid. Following a two-day incubation period, flow cytometry was used to quantify fluorescence (FIG. 16B) and DNA sequencing was used to quantify mutations (FIGS. 16C and 16D). See, Carpenter et al. 2012, supra; and Stenglein et al., supra). The histogram in FIG. 16B shows that A3A and A3AL7 have similar foreign DNA restriction activities. The histogram in FIG. 16C shows the actual dinucleotide frequency in the sequenced plasmid DNA and the context of the mutated cytosines caused by A3A or A3AL7. Dinucleotide context: 5'-CC, black; 5'-TC, hatched; 5'-GC, dotted; 5'-AC, white. The mutation plots in FIG. 16D show the relative positions and dinucleotide contexts of C/G to T/A mutations in the sequenced plasmid DNA.

DETAILED DESCRIPTION

Figure 1:
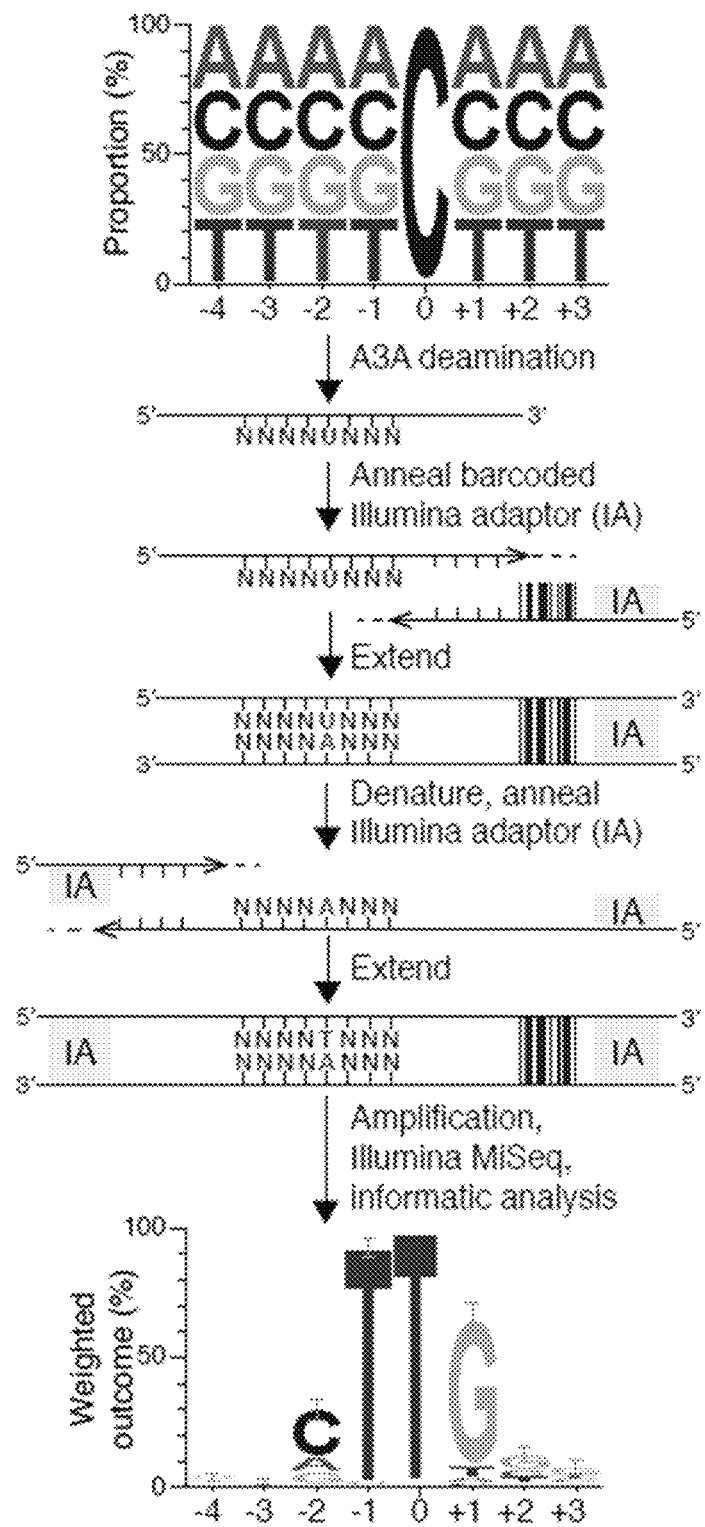
FIG. 1 is a diagram depicting a deep-deamination approach for determining an optimal human APOBEC3A (A3A) substrate. A ssDNA library with a single target C and N's on the 5' and 3' sides was reacted with human A3A (near-single hit kinetics). The resulting pool containing C-to-U deamination products was annealed to a bar-coded Illumina adaptor (IA), and T4 DNA polymerase was used to produce a complementary DNA strand. This intermediate was denatured, annealed to a 5'-IA, and converted to duplex by Phusion thermostable high fidelity DNA polymerase. Illumina Mi-Seq was used to generate reads for subsequent informatics analysis. A weblogo representation of deamination products unique to A3A shows enrichment for −1 T and +1 G, which informed the ssDNA sequence for co-crystallization experiments (n=641; error bars are twice the sample correction value). Source data are provided in TABLE 1.

Isolated fusion polypeptides containing an APOBEC portion and a DNA-targeting (e.g., Cas9) portion are provided herein. The term "polypeptide" as used herein refers to a compound of two or more subunit amino acids regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

Nucleic acids encoding the DNA-targeted APOBEC fusion polypeptides also are provided herein. The terms "nucleic acid" and "polynucleotide" are used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The polypeptides provided herein can be introduced in a cell by using a vector encoding said polypeptides for example or as polypeptides per se by using delivery vectors associated or combined with any cellular permeabilization techniques, such as sonoporation, electroporation, lipofection, or derivatives of these or other related techniques.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

Recombinant nucleic acid constructs (e.g., vectors) also are provided herein. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, Nuclear Localization Sequences (NLS) and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 1000 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q −1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, an amino acid sequence that has 175 matches when aligned with the sequence set forth in SEQ ID NO:1 is 93.6 percent identical to the sequence set forth in SEQ ID NO:1 (i.e., 175/187×100=93.6). It is noted that the percent sequence identity value is rounded to the nearest tenth. For example, 75.11, 75.12, 75.13, and 75.14 is rounded down to 75.1, while 75.15, 75.16, 7.17, 75.18, and 7.19 is rounded up to 7.2. It also is noted that the length value will always be an integer.

An "effective amount" of an agent (e.g., a Cas9-APOBEC fusion polypeptide, a nucleic acid encoding such a polypeptide, or a composition containing a Cas9-APOBEC fusion polypeptide and a gRNA directing the fusion to a specific DNA sequence) is an amount of the agent that is sufficient to elicit a desired response. For example, an effective amount of a Cas9-APOBEC fusion polypeptide can be an amount of the polypeptide that is sufficient to induce deamination at a specific, selected target site. It is to be noted that the effective amount of an agent as provided herein can vary depending on various factors, such as, for example, the specific allele, genome, or target site to be edited, the cell or tissue being targeted, and the agent being used.

Human cells can produce up to seven distinct APOBEC3 enzymes, (A3A, A3B, A3C, A3D, A3F, A3G, and A3H), although most cells express subsets due to differential gene regulation (Refsland et al., supra; Koning et al., supra; Stenglein et al., supra; and Burns et al., supra). The local substrate preference of each APOBEC enzyme for RNA or ssDNA is an intrinsic property, and has helped to elucidate biological and pathological functions for several family members. See, e.g., Di Noia and Neuberger, supra; Robbiani and Nussenzweig, supra; Harris and Dudley, supra; Malim and Bieniasz, supra; Simon et al., supra; Helleday et al., *Nat Rev Genet* 15:585-598, 2014; Roberts and Gordenin, *Nat Rev Cancer* 14:786-800, 2014; and Swanton et al., *Cancer Discov* 5:704-712, 2015.

The nucleobase immediately 5' of the target cytosine (−1 relative to the target cytosine at position 0) appears to be the most important determinant of each enzyme's intrinsic substrate preference (Carpenter et al., *DNA Repair (Amst)* 9:579-587, 2010; Rathore et al., supra; Kohli et al., *J Biol Chem* 285:40956-40964, 2010; and Wang et al., *J Exp Med* 207:141-153, 2010). For example, AID preferentially deaminates single-stranded DNA cytosine bases preceded by an adenine or guanine (5'-RC). A3G uniquely targets cytosine bases preceded by another cytosine (5'-CC). APOBEC1 and the remaining APOBEC3 enzymes elicit preferences for cytosine bases preceded by a thymine (5'-TC). The −1 nucleobase preference is governed largely by a loop adjacent to the active site (loop 7), such that loop exchanges can convert one enzyme's intrinsic preference into that of another. For example, A3G with loop 7 from A3A becomes a 5'-TC preferring enzyme (Rathore et al., supra), while A3A with loop 7 from A3G becomes a 5'-CC preferring enzyme (FIGS. 16A-16D; "A3A" vs. "A3A L7"). The −2 and +1 nucleobases relative to the target cytosine also are likely to be involved in local target selection but are thought to be less influential.

The APOBEC mutation signature in cancer has been defined as C-to-T and C-to-G base substitution mutations within 5'-TC dinucleotide motifs, and most commonly within 5'-TCA and 5'-TCT trinucleotide contexts (also 5'-TCG if accounting for the genomic under-representation of this motif; Burns et al., supra; and Starrett et al., *Nat Commun* 7:12918, 2016). The leading candidates to explain APOBEC mutagenesis in cancer are A3A (Caval et al., *Nat Commun* 5:5129, 2014; Chan et al., *Nat Genet* 47:1067-1072, 2015; and Nik-Zainal et al., *Nat Genet* 46:487-491, 2014), A3B (Burns et al., supra; Starrett et al., supra; and Burns et al., *Nat Genet* 45:977-983, 2013b), and A3H (Starrett et al., supra).

An alignment of exemplary representative A3A and AB3 amino acid sequences (SEQ ID NOS: 1 and 2, respectively)

is shown in FIG. 2. The sequence set forth in SEQ ID NO:1 includes amino acids 13-199 of human A3A, and the sequence set forth in SEQ ID NO:2 includes amino acids 193-382 of human A3B; both contain the C-terminal catalytic domain). An additional representative A3A sequence is set forth in SEQ ID NO:19 (GENBANK® accession no. NM_145699), which encodes a full length human A3A polypeptide having SEQ ID NO:20 (UniProt ID P31941). An additional representative A3B sequence is set forth in SEQ ID NO:21 (GENBANK® accession no. NM_004900), which encodes a full length human A3B polypeptide having SEQ ID NO:22 (UniProt ID Q9UH17). SEQ ID NOS: 19-22 are set forth below. Other human and non-human APOBEC sequences are known in the art (e.g., human APOBEC1, AID, APOBEC3C, APOBEC3D, APOBEC3F, APOBEC3G, and APOBEC3H; GENBANK® accession nos. NM_001644, NM_020661, NM_014508, NM_152426, NM_145298, NM_021822, and NM_181773, respectively), and may be used in the fusion polypeptides and methods provided herein.

```
Human APOBEC3A (NM_145699):
                                         (SEQ ID NO: 19)
GGAGAAGGGGTGGGGCAGGGTATCGCTGACTCAGCAGCTTCCAGGTTGCT

CTGATGATATATTAAGGCTCCTGAATCCTAAGAGAATGTTGGTGAAGATC

TTAACACCACGCCTTGAGCAAGTCGCAAGAGCGGGAGGACACAGACCAGG

AACCGAGAAGGGACAAGCACATGGAAGCCAGCCCAGCATCCGGGCCCAGA

CACTTGATGGATCCACACATATTCACTTCCAACTTTAACAATGGCATTGG

AAGGCATAAGACCTACCTGTGCTACGAAGTGGAGCGCCTGGACAATGGCA

CCTCGGTCAAGATGGACCAGCACAGGGGCTTTCTACACAACCAGGCTAAG

AATCTTCTCTGTGGCTTTTACGGCCGCCATGCGGAGCTGCGCTTCTTGGA

CCTGGTTCCTTCTTTGCAGTTGGACCCGGCCCAGATCTACAGGGTCACTT

GGTTCATCTCCTGGAGCCCTGCTTCTCCTGGGGCTGTGCCGGGGAAGTG

CGTGCGTTCCTTCAGGAGAACACACACGTGAGACTGCGTATCTTCGCTGC

CCGCATCTATGATTACGACCCCCTATATAAGGAGGCACTGCAAATGCTGC

GGGATGCTGGGGCCCAAGTCTCCATCATGACCTACGATGAATTTAAGCAC

TGCTGGGACACCTTTGTGGACCACCAGGGATGTCCCTTCCAGCCCTGGGA

TGGACTAGATGAGCACAGCCAAGCCCTGAGTGGGAGGCTGCGGGCCATTC

TCCAGAATCAGGGAAACTGAAGGATGGGCCTCAGTCTCTAAGGAAGGCAG

AGACCTGGGTTGAGCAGCAGAATAAAAGATCTTCTTCCAAGAAATGCAAA

CAGACCGTTCACCACCATCTCCAGCTGCTCACAGACGCCAGCAAAGCAGT

ATGCTCCCGATCAAGTAGATTTTTAAAAAATCAGAGTGGGCCGGGCGCGG

TGGCTCACGCCTGTAATCCCAGCACTTTGGAGGCCAAGGCGGGTGGATCA

CGAGGTCAGGAGATCGAGACCATCCTGGCTAACACGGTGAAACCCTGTCT

CTACTAAAAATACAAAAAATTAGCCAGGCGTGGTGGCGGGCGCCTGTAGT

CCCAGCTACTCTGGAGGCTGAGGCAGGAGAGTAGCGTGAACCCGGGAGGC

AGAGCTTGCGGTGAGCCGAGATTGCGCTACTGCACTCCAGCCTGGGCGAC

AGTACCAGACTCCATCTCAAAAAAAAAAAAACCAGACTGAATTAATTTTA

ACTGAAAATTTCTCTTATGTTCCAAGTACACAATAGTAAGATTATGCTCA

ATATTCTCAGAATAATTTTCAATGTATTAATGAAATGAAATGATAATTTG

GCTTCATATCTAGACTAACACAAAATTAAGAATCTTCCATAATTGCTTTT

GCTCAGTAACTGTGTCATGAATTGCAAGAGTTTCCACAAACACT

Human APOBEC3A (UniProt ID P31941):
                                         (SEQ ID NO: 20)
MEASPASGPRHLMDPHIFTSNFNNGIGRHKTYLCYEVERLDNGTSVKMDQ

HRGFLHNQAKNLLCGFYGRHAELRFLDLVPSLQLDPAQIYRVTWFISWSP

CFSWGCAGEVRAFLQENTHVRLRIFAARIYDYDPLYKEALQMLRDAGAQV

SIMTYDEFKHCWDTFVDHQGCPFQPWDGLDEHSQALSGRLRAILQNQGN

Human APOBEC3B (NM_004900):
                                         (SEQ ID NO: 21)
CACAGAGCTTCAAAAAAGAGCGGGACAGGGACAAGCGTATCTAAGAGGC

TGAACATGAATCCACAGATCAGAAATCCGATGGAGCGGATGTATCGAGAC

ACATTCTACGACAACTTTGAAAACGAACCCATCCTCTATGGTCGGAGCTA

CACTTGGCTGTGCTATGAAGTGAAAATAAAGAGGGGCCGCTCAAATCTCC

TTTGGGACACAGGGGTCTTTCGAGGCCAGGTGTATTTCAAGCCTCAGTAC

CACGCAGAAATGTGCTTCCTCTCTTGGTTCTGTGGCAACCAGCTGCCTGC

TTACAAGTGTTTCCAGATCACCTGGTTTGTATCCTGGACCCCCTGCCCGG

ACTGTGTGGCGAAGCTGGCCGAATTCCTGTCTGAGCACCCCAATGTCACC

CTGACCATCTCTGCCGCCCGCCTCTACTACTACTGGGAAAGAGATTACCG

AAGGGCGCTCTGCAGGCTGAGTCAGGCAGGAGCCCGCGTGAAGATCATGG

ACTATGAAGAATTTGCATACTGCTGGGAAAACTTTGTGTACAATGAAGGT

CAGCAATTCATGCCTTGGTACAAATTCGATGAAAATTATGCATTCCTGCA

CCGCACGCTAAAGGAGATTCTCAGATACCTGATGGATCCAGACACATTCA

CTTTCAACTTTAATAATGACCCTTTGGTCCTTCGACGGCGCCAGACCTAC

TTGTGCTATGAGGTGGAGCGCCTGGACAATGGCACCTGGGTCCTGATGGA

CCAGCACATGGGCTTTCTATGCAACGAGGCTAAGAATCTTCTCTGTGGCT

TTTACGGCCGCCATGCGGAGCTGCGCTTCTTGGACCTGGTTCCTTCTTTG

CAGTTGGACCCGGCCCAGATCTACAGGGTCACTTGGTTCATCTCCTGGAG

CCCCTGCTTCTCCTGGGGCTGTGCCGGGGAAGTGCGTGCGTTCCTTCAGG

AGAACACACACGTGAGACTGCGCATCTTCGCTGCCCGCATCTATGATTAC

GACCCCCTATATAAGGAGGCGCTGCAAATGCTGCGGGATGCTGGGGCCCA

AGTCTCCATCATGACCTACGATGAGTTTGAGTACTGCTGGGACACCTTTG

TGTACCGCCAGGGATGTCCCTTCCAGCCCTGGGATGGACTAGAGGAGCAC

AGCCAAGCCCTGAGTGGGAGGCTGCGGGCCATTCTCCAGAATCAGGGAAA

CTGAAGGATGGGCCTCAGTCTCTAAGGAAGGCAGAGACCTGGGTTGAGCA

GCAGAATAAAAGATCTTCTTCCAAGAAATGCAAACAGACCGTTCACCACC

ATCTCCAGCTGCTCACAGACACCAGCAAAGCAATGTGCTCCTGATCAAGT

AGATTTTTAAAAATCAGAGTCAATTAATTTTAATTGAAAATTTCTCTTA

TGTTCCAAGTGTACAAGAGTAAGATTATGCTCAATATTCCCAGAATAGTT

TTCAATGTATTAATGAAGTGATTAATTGGCTCCATATTTAGACTAATAAA

ACATTAAGAATCTTCCATAATTGTTTCCACAAACACTAAAAAAAAAAAAA

AAAAAAAAA
```

-continued

Human APOBEC3B (UniProt ID Q9UH17):

(SEQ ID NO: 22)
MNPQIRNPMERMYRDTFYDNFENEPILYGRSYTWLCYEVKIKRGRSNLLW

DTGVFRGQVYFKPQYHAEMCFLSWFCGNQLPAYKCFQITWFVSWTPCPDC

VAKLAEFLSEHPNVTLTISAARLYYYWERDYRRALCRLSQAGARVKIMDY

EEFAYCWENFVYNEGQQFMPWYKFDENYAFLHRTLKEILRYLMDPDTFTF

NFNNDPLVLRRRQTYLCYEVERLDNGTWVLMDQHMGFLCNEAKNLLCGFY

GRHAELRFLDLVPSLQLDPAQIYRVTWFISWSPCFSWGCAGEVRAFLQEN

THVRLRIFAARIYDYDPLYKEALQMLRDAGAQVSIMTYDEFEYCWDTFVY

RQGCPFQPWDGLEEHSQALSGRLRAILQNQGN

A Cas9-APOBEC fusion polypeptide as provided herein can include the full-length amino acid sequence of an APOBEC protein, or a catalytic fragment of an APOBEC protein (e.g., a fragment that includes the C-terminal catalytic domain). The APOBEC portion of a Cas9-APOBEC fusion also may contain a variant APOBEC polypeptide having an amino acid sequence that is at least about 90% identical to a reference APOBEC sequence or a fragment thereof (e.g., at least about 91%, 92%, 93%, 94%, 95%, 96%, 97%, 98%, 99%, 99.5%, or 99.8% identical to SEQ ID NO:1, SEQ ID NO:2, SEQ ID NO:20, or SEQ ID NO:22, or a fragment thereof). In some embodiments, for example, a fusion polypeptide as provided herein can include an APOBEC portion that consists essentially of amino acids 13 to 199 of SEQ ID NO:20, amino acids 1 to 195 of SEQ ID NO:20, amino acids 13 to 195 of SEQ ID NO:20, or a sequence that is at least about 90% identical to such a fragment of SEQ ID NO:20. In some embodiments, the APOBEC portion can lack at least amino acids 1-12 of SEQ ID NO:20, at least amino acids 196-199 of SEQ ID NO:20, or at least amino acids 1-12 and 196-199 of SEQ ID NO:20. In some embodiments, the APOBEC portion of a fusion polypeptide as provided herein can consist essentially of amino acids 193 to 382 of SEQ ID NO:22, amino acids 193 to 378 of SEQ ID NO:22, or a sequence that is at least about 90% identical to such a fragment of SEQ ID NO:22. In some embodiments, the APOBEC portion can lack at least amino acids 1-192 of SEQ ID NO:22, or at least amino acids 1-192 and 379-382 of SEQ ID NO:22.

As described herein, the amino acid positions within the A3A and A3B enzymes that determine the −1 nucleobase preference have now been identified. In particular, evidence disclosed herein indicates that the aspartic acid residue at position 131 of SEQ ID NO:20 (position 314 of SEQ ID NO:22) is a determinant of APOBEC target specificity. This position is within loop 7 of the A3A and A3B proteins. Variant APOBEC polypeptides that have altered preference for the nucleobase at the −1 position therefore are provided herein, together with nucleic acids encoding the variant APOBEC polypeptides, host cells containing the nucleic acids, and methods for using the polypeptides and nucleic acids for targeted DNA modification. These variant APOBEC polypeptides can include mutations within loop 7, for example. In some cases, a variant APOBEC polypeptide be a loop-exchanged chimera, with amino acids from loop 7 of a different APOBEC polypeptide substituted for the loop 7 amino acids normally found within the polypeptide. For example, in some embodiments, amino acids present within loop 7 of A3A can be replaced by amino acids from the corresponding portion of A3G or AID. By coupling a variant APOBEC polypeptide sequence to a targeting molecule, it is possible to modify selected DNA sequences in a highly specific manner. Thus, fusion polypeptides containing a variant APOBEC portion and a targeting (e.g., Cas9) portion also are provided herein, as are nucleic acids encoding the variant APOBEC and Cas9-APOBEC fusion polypeptides, host cells containing the nucleic acids, and methods for using the polypeptides and nucleic acids for targeted DNA modification.

The CRISPR/Cas system includes components of a prokaryotic adaptive immune system that is functionally analogous to eukaryotic RNA interference, using RNA base pairing to direct DNA or RNA cleavage. The Cas9 protein functions as an endonuclease, and CRISPR RNA (crRNA) and tracer RNA (tracrRNA) sequences complex with the Cas9 enzyme and direct it to a target DNA sequence (Makarova et al., Nat Rev Microbiol 9(6):467-477, 2011). The modification of a single targeting RNA can be sufficient to alter the nucleotide target of a Cas protein. In some cases, crRNA and tracrRNA can be engineered as a single cr/tracrRNA hybrid (also referred to as a "guide RNA" or "gRNA") to direct Cas9 cleavage activity (Jinek et al., Science, 337(6096):816-821, 2012). The CRISPR/Cas system can be used in a variety of prokaryotic and eukaryotic organisms (see, e.g., Jiang et al., Nat Biotechnol, 31(3):233-239, 2013; Dicarlo et al., Nucleic Acids Res, doi:10.1093/nar/gkt135, 2013; Cong et al., Science, 339(6121):819-823, 2013; Mali et al., Science, 339(6121):823-826, 2013; Cho et al., Nat Biotechnol, 31(3):230-232, 2013; and Hwang et al., Nat Biotechnol, 31(3):227-229, 2013).

CRISPR clusters are transcribed and processed into crRNA; the correct processing into crRNA requires a trans-encoded small tracrRNA. The combination of Cas9, crRNA, and tracrRNA can then cleave linear or circular dsDNA targets that are complementary to a spacer within the CRISPR cluster. Cas9 recognizes a short protospacer adjacent motif (PAM) in the CRISPR repeat sequences, which aids in distinguishing self from non-self. Cas9 nuclease sequences and structures are well known to those of skill in the art (see, e.g., Ferretti et al., Proc Natl Acad Sci USA 98:4658-4663, 2001; Deltcheva et al., Nature 471:602-607, 2011; and Jinek Science 337:816-821, 2012). Cas9 orthologs also have been described in species such as S. pyogenes and S. thermophilus.

The homology region within the crRNA sequence (the sequence that targets the crRNA to the desired DNA sequence) can be between about 10 and about 40 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40) nucleotides in length. The tracrRNA hybridizing region within each crRNA sequence can be between about 8 and about 20 (e.g., 8, 9, 10, 11, 12, 13, 14, 15, 16, 17, 18, 19, or 20) nucleotides in length. The overall length of a crRNA sequence can be, for example, between about 20 and about 80 (e.g., 20, 25, 30, 35, 40, 45, 50, 55, 60, 65, 70, 75, or 80) nucleotides, while the overall length of a tracrRNA can be, for example, between about 10 and about 30 (e.g., 10, 12, 14, 16, 18, 20, 22, 24, 26, 28, or 30) nucleotides. The overall length of a gRNA sequence, which includes a homology region and a stem loop region that contains a crRNA/tracrRNA hybridizing region and a linker-loop sequence, can be between about 30 and about 110 (e.g., 30, 35, 40, 45, 50, 55, 60, 65, 70, 75, 80, 85, 90, 95, 100, 105, 110, 115, 120, 125, or 130) nucleotides.

In some embodiments, the Cas9 portion of the fusion polypeptides provided herein can include the non-catalytic portion of a wild type Cas9 polypeptide, or a Cas9 polypeptide containing one or more mutations (e.g., substitutions, deletions, or additions) within its amino acid sequence as compared to the amino acid sequence of a corresponding wild type Cas9 protein, where the mutant Cas9 does not have nuclease activity. In some embodiments, additional amino acids may be added to the N- and/or C-terminus. For example, Cas9 protein can be modified by the addition of a VP64 activation domain or a green fluorescent protein to the C-terminus, or by the addition of nuclear-localization signals to both the N- and C-termini (see, e.g., Mali et al. *Nature Biotechnol* 31:833-838, 2013; and Cong et al. *Science* 339:819-823). A representative Cas9 nucleic acid sequence is set forth in SEQ ID NO:7, and a representative Cas9 amino acid sequence is set forth in SEQ ID NO:8. *Streptococcus pyogenes* (NCBI Ref. NC_017053.1) Cas9:

(SEQ ID NO: 7)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGCGCCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACAGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCCAAGTGAAGAAGTAGTCAAAAAGATGAAAAACTATTGGAGAC

AACTTCTAAACGCCAAGTTAATCACTCAACGTAAGTTTGATAATTTAACG

AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC

ATGATGCGTATCTAAATGCCGTCGTTGGAACTGCTTTGATTAAGAAATAT

CCAAAACTTGAATCGGAGTTTGTCTATGGTGATTATAAAGTTTATGATGT

TCGTAAAATGATTGCTAAGTCTGAGCAAGAAATAGGCAAAGCAACCGCAA

AATATTTCTTTTACTCTAATATCATGAACTTCTTCAAAACAGAAATTACA

CTTGCAAATGGAGAGATTCGCAAACGCCCTCTAATCGAAACTAATGGGGA

AACTGGAGAAATTGTCTGGGATAAAGGGCGAGATTTTGCCACAGTGCGCA

AAGTATTGTCCATGCCCCAAGTCAATATTGTCAAGAAAACAGAAGTACAG

ACAGGCGGATTCTCCAAGGAGTCAATTTTACCAAAAAGAAATTCGGACAA

GCTTATTGCTCGTAAAAAAGACTGGGATCCAAAAAAATATGGTGGTTTTG

ATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTA

AAGGATATAAGGAAGTTAAAAAAGACTTAATCATTAAACTACCTAAATAT

```
                                                      -continued
AGTCTTTTTGAGTTAGAAAACGGTCGTAAACGGATGCTGGCTAGTGCCGG

AGAATTACAAAAAGGAAATGAGCTGGCTCTGCCAAGCAAATATGTGAATT

TTTTATATTTAGCTAGTCATTATGAAAAGTTGAAGGGTAGTCCAGAAGAT

AACGAACAAAAACAATTGTTTGTGGAGCAGCATAAGCATTATTTAGATGA

GATTATTGAGCAAATCAGTGAATTTTCTAAGCGTGTTATTTTAGCAGATG

CCAATTTAGATAAAGTTCTTAGTGCATATAACAAACATAGAGACAAACCA

ATACGTGAACAAGCAGAAAATATTATTCATTTATTTACGTTGACGAATCT

TGGAGCTCCCGCTGCTTTTAAATATTTTGATACAACAATTGATCGTAAAC

GATATACGTCTACAAAAGAAGTTTTAGATGCCACTCTTATCCATCAATCC

ATCACTGGTCTTTATGAAACACGCATTGATTTGAGTCAGCTAGGAGGTGA

CTGA
```

*S. pyogenes* Cas9 protein:

```
                                         (SEQ ID NO: 8)
MDKKYSIGLDIGTNSVGWAVITDDYKVPSKKFKVLGNTDRHSIKKNLIG

ALLFGSGETAEATRLKRTARRRYTRRKNRICYLQEIFSNEMAKVDDSFFH

RLEESFLVEEDKKHERHPIFGNIVDEVAYHEKYPTIYHLRKKLADSTDKA

DLRLIYLALAHMIKFRGHFLIEGDLNPDNSDVDKLFIQLVQIYNQLFEEN

PINASRVDAKAILSARLSKSRRLENLIAQLPGEKRNGLFGNLIALSLGLT

PNFKSNFDLAEDAKLQLSKDTYDDDLDNLLAQIGDQYADLFLAAKNLSDA

ILLSDILRVNSEITKAPLSASMIKRYDEHHQDLTLLKALVRQQLPEKYKE

IFFDQSKNGYAGYIDGGASQEEFYKFIKPILEKMDGTEELLVKLNREDLL

RKQRTFDNGSIPHQIHLGELHAILRRQEDFYPFLKDNREKIEKILTFRIP

YYVGPLARGNSRFAWMTRKSEETITPWNFEEVVDKGASAQSFIERMTNFD

KNLPNEKVLPKHSLLYEYFTVYNELTKVKYVTEGMRKPAFLSGEQKKAIV

DLLFKTNRKVTVKQLKEDYFKKIECFDSVEISGVEDRFNASLGAYHDLLK

IIKDKDFLDNEENEDILEDIVLTLTLFEDRGMIEERLKTYAHLFDDKVMK

QLKRRRYTGWGRLSRKLINGIRDKQSGKTILDFLKSDGFANRNFMQLIHD

DSLTFKEDIQKAQVSGQGHSLHEQIANLAGSPAIKKGILQTVKIVDELVK

VIVIGHKPENIVIEMARENQTTQKGQKNSRERMKRIEEGIKELGSQILKE

HPVENTQLQNEKLYLYYLQNGRDMYVDQELDINRLSDYDVDHIVPQSFIK

DDSIDNKVLTRSDKNRGKSDNVPSEEVVKKMKNYWRQLLNAKLITQRKFD

NLTKAERGGLSELDKAGFIKRQLVETRQITKHVAQILDSRMNTKYDENDK

LIREVKVITLKSKLVSDFRKDFQFYKVREINNYHHAHDAYLNAVVGTALI

KKYPKLESEFVYGDYKVYDVRKMIAKSEQEIGKATAKYFFYSNIMNFFKT

EITLANGEIRKRPLIETNGETGEIVWDKGRDFATVRKVLSMPQVNIVKKT

EVQTGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKL

PKYSLFELENGRKRMLASAGELQKGNELALPSKYVNFLYLASHYEKLKGS

PEDNEQKQLFVEQHKHYLDEIIEQISEFSKRVILADANLDKVLSAYNKHR
```

```
                                       -continued
DKPIREQAENIIHLFTLTNLGAPAAFKYFDTTIDRKRYTSTKEVLDATLI

HQSITGLYETRIDLSQLGGD.
```

A Cas9-APOBEC fusion polypeptide as provided herein can include the full-length amino acid sequence of a Cas9 protein, or a fragment of a Cas9 protein. Typically, the Cas9-APOBEC fusion polypeptides provided herein include a Cas9 fragment that can bind to a crRNA and tracrRNA (or a gRNA), but does not include a functional nuclease domain. For example, the fusion may contain a non-functional nuclease domain, or a portion of a nuclease domain that is not sufficient to confer nuclease activity, or may lack a nuclease domain altogether. Thus, in some cases, a Cas9-APOBEC fusion polypeptide can contain a fragment of Cas9, such as a fragment including the Cas9 gRNA binding domain, or a fragment that includes both the gRNA binding domain and an inactivated version of the DNA cleavage domain. The Cas portion of a Cas9-APOBEC fusion also may contain a variant Cas polypeptide having an amino acid sequence that is at least about 90% identical to a wild type Cas9 sequence (e.g., at least about 91%, 92%, 93%, 94%, 95%, 96%, 97%, 98%, 99%, 99.5%, or 99.8% identical to a wild type Cas9 amino acid sequence).

In some embodiments, the fusion polypeptides provided herein can include a "nuclease-dead" Cas9 polypeptide that lacks nuclease activity and may or may not have nickase activity (such that it cuts one strand of a double-stranded DNA), but can bind to a preselected target sequence when complexed with crRNA and tracrRNA (or gRNA). Without being bound by a particular mechanism, the use of a DNA targeting polypeptide with nickase activity, where the nickase generates a strand-specific cut on the strand opposing the uracil to be modified, can have the subsequent effect of directing repair machinery to non-modified strand, resulting in repair of the nick so both strands are modified. For example, with respect to the Cas9 sequence of SEQ ID NO:8, a Cas9 polypeptide can be a D10A Cas9 polypeptide (or a portion thereof) that has nickase activity but not nuclease activity, or a H840A Cas9 polypeptide (or a portion thereof) that has nickase activity but not nuclease activity.

In some embodiments, a "nuclease-dead" polypeptide can be a D10A H840A Cas9 polypeptide (or a portion thereof) that has neither nickase nor nuclease activity. A Cas9 polypeptide also can be a D10A D839A H840A N863A Cas9 polypeptide in which alanine residues are substituted for the aspartic acid residues at positions 10 and 839, the histidine residue at position 840, and the asparagine residue at position 863 (with respect to SEQ ID NO:8). See, e.g., Mali et al., *Nature Biotechnol*, supra; Jinek et al., supra; and Qi et al., *Cell* 152(5):1173-83, 2013.

An exemplary reference Cas9 amino acid sequence having an inactivated nuclease domain with D10A and H840A mutations (underlined) is:

```
                                         (SEQ ID NO: 9)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI
```

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

An exemplary reference Cas9 amino acid sequence having an inactivated nuclease domain with a D10A mutation (underlined) is:

(SEQ ID NO: 73)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVKLFIQLVQTYNQLFEENP

INASGVDAKAILSARLSKSRRLENLIAQLPGEKKNGLFGNLIALSLGLTP

NEKSNEDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECEDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

An exemplary reference Cas9 amino acid sequence having an inactivated nuclease domain with a H840A mutation (underlined) is:

(SEQ ID NO: 74)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIIVINFFKT

EITLANGEIRKRPLIETNGETGEIVWDKGRDFATVRKVLSMPQVNIVKKT

EVQTGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKL

-continued
PKYSLFELENGRKRMLASAGELQKGNELALPSKYVNFLYLASHYEKLKGS

PEDNEQKQLFVEQHKHYLDEIIEQISEFSKRVILADANLDKVLSAYNKHR

DKPIREQAENIIHLFTLTNLGAPAAFKYFDTTIDRKRYTSTKEVLDATLI

HQSITGLYETRIDLSQLGGD.

In some embodiments, Cas9 variants containing mutations other than D10A and H840A and lacking nuclease activity are provided herein. Such variants include, without limitation, include other amino acid substitutions at D10 and H840, or other substitutions within the Cas9 nuclease domains. In some embodiments, a Cas9 variant can have one or more amino acid additions or deletions (e.g., one, two, three, four, five, six, seven, eight, nine, 10, 10 to 20, 20 to 40, 40 to 50, or 50 to 100 additions or deletions) as compared to a reference Cas9 sequence (e.g., the sequence set forth in SEQ ID NO:8. It is noted, for example, that Cas9 has two separate nuclease domains that allow it to cut both strands of a double-stranded DNA. These are referred to as the "RuvC" and "HNH" domains. Each includes several active site metal-chelating residues. In the RuvC domain, the metal-chelating residues are D10, E762, H983, and D986, while in the HNH domain, the metal-chelating residues are D839, H840, and N863. Mutation of one or more of these residues (e.g., by substituting an alanine for the natural amino acid) may convert Cas9 into a nickase, while mutating one residue from each domain can result in a nuclease-dead and nickase-dead Cas9.

The Cas9 sequences used in the fusion polypeptides provided herein also can be based on natural or engineered Cas9 molecules from organisms such as *Corynebacterium ulcerans* (NCBI Refs: NC_015683.1 and NC_017317.1), *C. diphtheria* (NCBI Refs: NC_016782.1 and NC_016786.1), *Spiroplasma syrphidicola* (NCBI Ref: NC_021284.1), *Prevotella intermedia* (NCBI Ref: NC_017861.1), *Spiroplasma taiwanense* (NCBI Ref: NC_021846.1), *Streptococcus iniae* (NCBI Ref: NC_021314.1), *Belliella baltica* (NCBI Ref: NC_018010.1), *Psychroflexus torquisI* (NCBI Ref: NC_018721.1), *Streptococcus thermophilus* (NCBI Ref: YP_820832.1), *Listeria innocua* (NCBI Ref: NP_472073.1), *Campylobacter jejuni* (NCBI Ref: YP_002344900.1), *Neisseria meningitidis* (NCBI Ref: YP_002342100.1), and *Francisella novicida*. RNA-guided nucleases that have similar activity to Cas9 but are from other types of CRISPR/Cas systems, such as *Acidaminococcus* sp. or Lachnospiraceae bacterium ND2006 Cpf1 (see, e.g., Yamano et al., *Cell* 165(4):949-962, 2016; and Dong et al., *Nature* 532(7600): 522-526, 2016) also can be used in fusion polypeptides with APOBEC deaminases.

The domains within Cas9-APOBEC fusion polypeptides provided herein can be positioned in any suitable configuration. In some embodiments, for example, the APOBEC portion can be coupled to the N-terminus of the Cas9 portion, either directly or via a linker. Alternatively, the APOBEC portion can be fused to the C-terminus of the Cas9 portion, either directly or via a linker. In some cases, the APOBEC portion can be fused within an internal loop of Cas9. Suitable linkers include, without limitation, an amino acid or a plurality of amino acids (e.g., five to 50 amino acids, 10 to 20 amino acids, 15 to 25 amino acids, or 25 to 50 amino acids, such as (GGGGS)$_n$ (SEQ ID NO:10), (G)n, (EAAAK)$_n$ (SEQ ID NO:11), (GGS)$_n$, a SGSETPGTS-ESATPES (SEQ ID NO:12) motif (see, e.g., Guilinger et al., *Nat Biotechnol* 32(6):577-582, 2014), an (XP)$_n$ motif, or a combination thereof, where n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30). Suitable linkers also include organic groups, polymers, and chemical moieties. Useful linker motifs also are described elsewhere (see, e.g., Chen et al., *Adv Drug Deliv Rev* 65(10):1357-1369, 2013). When included, a linker can be connected to each domain via a covalent bond, for example.

Additional components that may be present in the fusion polypeptides provided herein include, such as one or more nuclear localization sequences (NLS), cytoplasmic localization sequences, export sequences (e.g., a nuclear export sequence), or sequence tags that are useful for solubilization, purification, or detection of the fusion protein. Suitable localization signal sequences and sequences of protein tags include, without limitation, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Fusion polypeptides also can include other functional domains, such as, without limitation, a domain from the bacteriophage UGI protein that is a universal inhibitor of uracil DNA glycosylase enzymes (UNG2 in human cells; see, e.g., Di Noia and Neuberger, *Nature* 419(6902):43-48, 2002) that can prevent the deaminated cytosine (DNA uracil) from being repaired by cellular base excision repair (see, e.g., Komor et al., *Nature* 533(7603):420-424, 2016; and Mol et al., *Cell* 82:701-708, 1995).

As described herein, Cas9-APOBEC-CRISPR systems can be used for targeted DNA editing, where the CRISPR RNA molecules (the crRNA and tracrRNA, or a cr/tracrRNA hybrid) targeted to a particular sequence (e.g., in a genome or in an extrachromosomal plasmid) act to direct the Cas9 portion of a Cas9-APOBEC fusion polypeptide to the target sequence, permitting the APOBEC portion of the fusion to modify a particular cytosine residue at the desired sequence.

Thus, this document provides methods for using Cas9-APOBEC-CRISPR systems to generate targeted modifications within cellular DNA sequences. The methods can include contacting a target nucleic acid with a Cas9-APOBEC fusion polypeptide in the presence of one or more CRISPR RNA molecules. In some embodiments, the methods can include transforming or transfecting a cell (e.g., a bacterial, plant, or animal cell) with (i) a first nucleic acid encoding a Cas9-APOBEC fusion polypeptide, and (ii) a second nucleic acid containing a crRNA sequence and a tracrRNA sequence (or a gRNA sequence) targeted to a DNA sequence of interest. Such methods also can include maintaining the cell under conditions in which nucleic acids (i) and (ii) are expressed.

After a nucleic acid is contacted with a Cas9-APOBEC fusion polypeptide and CRISPR RNA, or after a cell is transfected or transformed with a Cas9-APOBEC fusion and a CRISPR RNA, or with one or more nucleic acids encoding the fusion and the CRISPR RNA, any suitable method can be used to determine whether mutagenesis has occurred at the target site. In some embodiments, a phenotypic change can indicate that a change has occurred the target site. PCR-based methods also can be used to ascertain whether a target site contains a desired mutation.

When a first nucleic acid encoding a Cas9-APOBEC fusion polypeptide and a second nucleic acid containing a crRNA and a trRNA (or a gRNA) are used, the first and second nucleic acids can be included within a single construct, or in separate constructs. Thus, while in some cases it may be most efficient to include sequences encoding the Cas9-APOBEC polypeptide, the crRNA, and the tracrRNA in a single construct (e.g., a single vector), in other cases first nucleic acid and the second nucleic acid can be present in separate nucleic acid constructs (e.g., separate vectors). In some embodiments, the crRNA and the tracrRNA also can be in separate nucleic acid constructs (e.g., separate vectors). Again, a "vector" is a replicon, such as a plasmid, phage, or cosmid, into which another DNA segment may be inserted so as to bring about the replication of the inserted segment.

The fusion polypeptides described herein, nucleic acids encoding the polypeptides, and compositions containing the polypeptides or nucleic acids, can be administered to a cell or to a subject (e.g., a human, a non-human mammal such as a non-human primate, a rodent, a sheep, a goat, a cow, a cat, a dog, a pig, or a rabbit, an amphibian, a reptile, a fish, or an insect) in order to specifically modify a targeted DNA sequence. In some cases, the targeted sequence can be selected based on its association with a particular clinical condition or disease, and the administration can be aimed at treating the clinical condition or disease. The term "treating" refer to reversal, alleviation, delaying the onset, or inhibiting the progress of the condition or disease, or one or more symptoms of the condition or disease. In some cases, administration can occur after onset of the clinical condition or disease (after one or more symptoms of the condition have developed, for example, or after the disease has been diagnosed). In some cases, however, administration may occur in the absence of symptoms, such that onset or progression of the clinical condition or disease is prevented or delayed. This may be the case when the subject is identified as being susceptible to the condition, for example, or when the subject has been previously treated for the condition and symptoms have resolved, but recurrence is possible.

In some embodiments, the methods provided herein can be used to introduce a point mutation into a nucleic acid by deaminating a target cytosine. For example, the targeted deamination of a particular cytosine may correct a genetic defect (e.g., a genetic defect is associated with a clinical condition or disease). In some embodiments, the methods provided herein can be used to introduce a deactivating point mutation into a sequence encoding a gene product associated with a clinical condition or disease (e.g., an oncogene). In some cases, for example, a deactivating mutation can create a premature stop codon in a coding sequence, resulting in the expression of a truncated gene product that may not be functional, or may lack the normal function of the full-length protein.

In some embodiments, the methods provided can be used to restore the function of a dysfunctional gene. For example, the Cas9-APOBEC fusion polypeptides described herein can be used in vitro or in vivo to correct a disease-associated mutation (e.g., in cell culture or in a subject). Thus, this document provides methods for treating subjects identified as having a clinical condition or disease that is associated with a point mutation. Such methods can include administering to a subject a Cas9-APOBEC fusion polypeptide, or a nucleic acid encoding a Cas9-APOBEC fusion polypeptide, in an amount effective to correct the point mutation or to introduce a deactivating mutation into the sequence associated with the disease. The disease can be, without limitation, a proliferative disease, a genetic disease, or a metabolic disease.

To target a Cas9-APOBEC fusion polypeptide to a target site (e.g., a site having a point mutation to be edited), the Cas9-APOBEC fusion can be co-expressed with a crRNA and tracrRNA, or a gRNA, that allows for Cas9 binding and confers sequence specificity to the Cas9-APOBEC fusion polypeptide. Suitable gRNA sequences typically include guide sequences that are complementary to a nucleotide sequence within about 50 (e.g., 25 to 50, 40 to 50, 40 to 60, or 50 to 75) nucleotides upstream or downstream of the target nucleotide to be edited.

In some embodiments, a reporter system can be used to detect activity of the fusion proteins described herein. See, for example, the luciferase-based assay described in US 2016/0304846, in which deaminase activity leads to expression of luciferase. US 2016/0304846 also describes a reporter system utilizing a reporter gene that has a deactivated start codon. In this reporter system, successful deamination of the target permits translation of the reporter gene.

It is to be noted that, while the examples provided herein relate to Cas9-APOBEC fusions, the use of other DNA-targeting molecules is contemplated. Thus, for example, a modified APOBEC polypeptide can be coupled to a DNA-targeting domain from a polypeptide such as a meganuclease (e.g., a wild type or variant protein of the homing endonuclease family, such as those belonging to the dodecapeptide family (LAGLIDADG; SEQ ID NO:75), a transcription activator-like (TAL) effector protein, or a zinc-finger (ZF) protein. Such proteins and their characteristics, function, and use are described elsewhere. See, e.g., WO 2004/067736/ Porteus, *Nature* 459:337-338, 2009; Porteus and Baltimore, *Science* 300:763, 2003; Bogdanove et al., *Curr Opin Plant Biol* 13:394-401, 2010; and Boch et al., *Science* 326(5959): 1509-1512, 2009.

The invention will be further described in the following examples, which do not limit the scope of the invention described in the claims.

EXAMPLES

Example 1—Materials and Methods

Protein Purification.

Human A3A with a single amino acid substitution (E72A) was expressed in the *E. coli* strain BL21(DE3) as a GST-fusion protein using the pGEX6P-1 vector. Transformed bacteria were grown to mid-log phase in LB medium, then supplemented with 100 µM $ZnCl_2$, and induced by addition of IPTG at a final concentration of 0.5 mM. After overnight incubation at 18° C., bacteria were collected by centrifugation, resuspended in lysis buffer (20 mM Tris-HCl pH 8.0, 0.5 M NaCl, 10 mM β-mercaptoethanol) and lysed by the addition of lysozyme and sonication. After centrifugation, the cleared lysate was passed through a 0.22 µm filter, and the protein was captured with glutathione agarose resin (Pierce), eluted in the lysis buffer supplemented with 10 mM reduced glutathione, cleaved by the human rhinovirus 3C protease to remove GST, and purified over a Superdex75 (GE Healthcare) size-exclusion column. The purified protein contains A3A residues 1-195 (near full-length) and additional vector-derived residues (GPLGSPEF; SEQ ID NO:13) at the N-terminus. The A3B construct used in this study was the A3Bctd-QMΔloop3-A3Aloop1 disclosed elsewhere (Shi et al., *J Biol Chem* 290:28120-28130, 2015), which has a substitution of the A3A loop1 residues (GIGRHK; SEQ ID NO:14) for A3B loop 1 (DPLVLRRRQ; SEQ ID NO:15) and single serine for the A3B loop 3 residues (spanning Ala242 to Tyr250; Shi et al., supra). A3Bctd-QMΔloop3-A3Aloop1 with the additional E255A amino acid substitution (referred to as A3Bctd*) was expressed with a non-cleavable C-terminal His6-tag (LEHHHHHH; SEQ ID NO:16) in the *E. coli* strain C41 (DE3)pLysS (Lucigen) from a pET24a-based vector and purified as reported elsewhere (Shi et al., supra). For both proteins, the final size-exclusion chromatography buffer consisted of 20 mM Tris-HCl (pH 7.4), 0.2 M NaCl, and 0.5 mM TCEP. The proteins were >95% pure based on visual inspection of Coomassie Blue-stained polyacrylamide gels. The purified enzymes were concentrated by ultrafiltration for use in the crystallization experiments. The initial A3A and A3B protein sequences match UniProt ID P31941 and Q9UH17, respectively (aligned in FIG. 2).

Crystallization and Structure Determination.

Purified A3A and A3Bctd* were mixed with ~1.5 molar excess ssDNA (see below) at a final protein concentration of 25-30 mg ml$^{-1}$. The A3A-ssDNA complex crystal was obtained in a sitting drop formed by mixing the complex solution with an equal volume of 0.2 M NaF, 20% (w/v) PEG3350, 0.1 M Bis-Tris propane (pH 6.5), equilibrated via vapor diffusion against the same reservoir solution. The A3Bctd*-ssDNA crystal was obtained similarly, using a reservoir solution consisting of 0.45 M NaI and 20% (w/v) PEG3350. The crystals were mounted directly from the Intelli-Plate 96 (Art Robbins Instruments) and flash cooled in liquid nitrogen using glycerol or ethylene glycol as cryo-protectant. X-ray diffraction data were collected at the Advanced Photon Source Northeastern Collaborative Access Team beamline 24-ID-C using the selenium K-absorption edge wavelength, and the data were processed with XDS (Kabsch, *Acta Crystallogr D Biol Crystallogr* 66:125-132, 2010). The A3A-DNA complex crystal is in the space group of P2221. A Matthews coefficient calculation indicated that there would likely be four monomers of A3A in an asymmetric unit. Using monomeric A3A (pdb 4XXO; Bohn et al., *Structure* 23:903-911, 2015) as a search model, the molecular replacement calculations by PHASER (McCoy et al., *J Appl Crystallogr* 40:658-674, 2007) located four copies of A3A in the asymmetric unit. The resulting electron density map clearly showed the presence of ssDNA bound to each A3A molecule (FIG. 3). The A3Bctd*-DNA complex crystal is in the space group of P6$_4$22 with one monomer in the asymmetric unit and diffracted to ~1.7 Å resolution. As the crystallization condition contained a high concentration of iodide ions, the diffraction data showed strong anomalous signal, and a total of 6 iodine or zinc sites were located using SHELXD (Sheldrick, *Acta Crystallogr D Biol Crystallogr* 66:479-485, 2010). The resulting single wavelength anomalous dispersion (SAD)-phased electron density map, after density modification using SHELXE, showed A3B monomer and the presence of a bound ssDNA molecule. The A3Bctd monomer (pdb 5CQK; Shi et al., supra) was placed into the electron density by molecular replacement using MOLREP (Vagin and Teplyakov, *Acta Crystallogr D Biol Crystallogr* 66:22-25, 2010). Subsequent iterative refinement with PHENIX suite (Adams et al., *Acta Crystallogr D Biol Crystallogr* 66:213-221, 2010) and manual model inspection and rebuilding using COOT (Emsley and Cowtan, *Acta Crystallogr D Biol Crystallogr* 60:2126-2132, 2004) resulted in the final R$_{work}$/R$_{free}$ of 20.97/26.30% and 18.11/21.21% for A3A-DNA and A3Bctd*-DNA complexes, respectively. Each A3A or A3Bctd* monomer was bound to one molecule of ssDNA substrate. The summary of x-ray data collection and model refinement statistics is shown in TABLE 3. Ramachandran analysis shows that 99.5, 0.5, and 0% of the protein residues are in the most favored, allowed, and disallowed region for A3A-ssDNA complex structure and 98.3, 1.7, and 0% for A3Bctd*-ssDNA complex, respectively. The molecular graphics images were produced using PYMOL (online at pymol.org).

TABLE 1

| Deaminated products (8-mers) | | | | | | | | |
|---|---|---|---|---|---|---|---|---|
| TGATCGAT | ATCTCGGT | TACTCGTT | TACTCGGG | GCTTCGGG | ATCTCGGG | TACTCTGC | TACTCGTG | ATCTCGAG |
| TGCTCGGG | GGCTCGGG | GTCTCGGG | TACTCTGG | TGTTCGGG | TACTCGGC | TTCTCGTG | TTCTCGGG | GCCTCGGG |
| TTCTCGGC | TGCTCGTG | AGCTCGGG | GGTTCGGG | GCATCGGG | TACTCGTA | GAGTCGCG | GTGTCGGG | TTCTCGGT |
| TTATCGGT | TTGTCGGG | TACTCTGT | GTCTCGAG | TACTCGGT | GACTCTGG | GTCTCGTT | TGCTCGTT | ATCTCGGC |
| GTCTCGTG | ATCTCGCG | AGCTCGGT | CACTCGGG | ATCTCGGA | TACTCAGT | CAGTCGGG | TTATCGGG | AGATCGTT |
| ATGTCGGG | GAGTCGGT | TCATCGTT | AGGTCGCG | TGCTCTTG | TTGTCGGC | GAGTCGTG | GCGTCGGG | GTCTCGCG |
| CACTCGGT | TACTCGCG | AACTCGGG | GGCTCTGG | CGCTCGGG | TGCTCTGG | TACTCGAG | TACTCGAT | AGGTCGGG |
| CGCTCTGT | CACTCGTT | TTATCGGC | TACTCGCT | TTCTCGAC | TGATCGGC | CACTCTGG | GTCTCGGT | GGCTCGGT |
| GTGTCGGC | GTCTCGGC | GAGTCGGC | CGCTCTGG | TACTCGCA | TGCTCGCT | TTCTCGAG | TACTCAGG | TGATCGGG |
| TTATCGCG | TTCTCGCA | AGGTCGGT | GAGTCGGG | GTATCGCG | TTCTCGGA | AGCTCGTT | ATCTCGCC | TGGTCGGG |
| GTCTCGGA | GGCTCGTG | ACCTCGGG | ACCTCGGT | TACTCGGA | TGCTCGGT | TGATCGTT | GCGTCGTG | ACGTCGTG |
| TGATCGGT | CTGTCGGG | TGATCGGA | GTCTCGCT | TACTCGCC | AGGTCGCA | GCCTCGTG | TGCTCGTA | AGCTCGTG |
| GCCTCGGA | GTGTCGCG | GACTCTGT | GAGTCGCA | GTGTCGGT | GGCTCGGA | TGATCGTA | GGCTCGCG | ATATCGGG |
| GTATCGGG | GCCTCTGT | GACTCGTT | ACATCGTT | TTCTCGCG | GGCTCGTT | CCCTCGTG | ACGTCGGG | GACTCGCT |
| CGCTCGTG | TCATCTGG | GCATCGTG | GCCTCGCT | AACTCTGG | TCCTCGGG | GCATCTGG | CACTCGGA | GGCTCGGC |
| TCATCGGG | GCCTCTGG | TACTCGAC | AACTCGCT | GCATCGTT | GCCTCGTT | AGCTCTGG | GTCTCGTC | TGCTCGGC |
| TGCTCGCA | GTGTCGGA | CGCTCGGT | TTCTCGCC | TGCTCGGA | GACTCGCA | AGCTCGAT | CCCTCGGT | GCCTCGGT |

TABLE 1-continued

| Deaminated products (8-mers) | | | | | | | | | |
|---|---|---|---|---|---|---|---|---|---|
| AACTCGGC | CACTCGAT | TCCTCGTT | TCCTCGTG | AACTCGTG | GTATCGGA | TTGTCGGT | AGGTCGTG | AACTCGGT |
| GACTCAGT | GACTCGGG | ATGTCGGC | TCATCGTG | AAATCGGT | ACGTCGGA | AGGTCGGC | CAATCGGT | TTCTCGCT |
| TACTCGTC | GACTCGAT | AGCTCGTA | AGCTCCCG | GCATCGGC | GGCTCTGT | AGATCGCG | GTCTCGGG | ATCTCGGG |
| ATCTCGGT | GTCTCGTG | TTCTCGTG | GTCTCGGT | ATCTCGCG | GTCTCGCG | TTCTCGGG | GTCTCGTT | GCTTCGGG |
| TACTCGTT | ATCTCGGA | ATCTCGAG | GTGTCGGG | GTCTCGAG | GTCTCGGA | TACTCGGG | GAGTCGGG | TTGTCGGG |
| TTCTCGAG | ATCTCGGC | GGTTCGGG | TGTTCGGG | TACTCGTG | GTCTCGCT | TTCTCGCG | GGCTCGGG | TTCTCGGA |
| TACTCTGG | TTCTCGGT | TGCTCGGG | GACTCGGG | AGGTCGGG | TTCTCGCT | ATGTCGGG | GTCTCGCA | GAGTCGTG |
| TACTCTGT | ATCTCGCC | GTGTCGCG | GAGTCGCG | TTCTCGCA | GTCTCGGC | TTGTCGGT | GGCTCGTG | GTGTCGGT |
| TTATCGGG | CTCTCGGG | AGCTCGGG | TTGTCGGC | TTCTCGCC | TTCTCGTC | TTCTCGGC | TACTCGTA | GACTCGTG |
| AGGTCGTG | GTCTCGTC | GTATCGCG | GTATCGGT | GTATCGGG | TACTCTGC | AGCTCGGT | TACTCGCG | CTCTCGGT |
| TGATCGGG | GTCTCGAA | TACTCGCT | TACTCGGT | AGCTCGTG | GGCTCGGT | TGATCGGT | TGCTCTGG | GAGTCGGT |
| TGCTCGGT | TGCTCGTG | GTGTCGGA | TGATCGTG | GTCTCGCC | GAGTCGCA | ATGTCGGC | AGATCGGT | TGATCGGC |
| TTATCGGT | CTCTCGTG | GTGTCGGC | TACTCGGA | TTATCGCG | GAGTCGGC | GGCTCTGG | AGCTCGTT | TGCTCGTT |
| GACTCTGG | GCGTCGGG | GCCTCGTG | TGATCGTT | GCCTCGGG | TACTCCGG | GTCTCGAC | AGGTCGGT | TGCTCTTG |
| TTCTCGAC | AGATCGTG | TCCTCGGG | TACTCCGT | TTGTCGGA | TACTCGTC | TGGTCGGG | ACGTCGGG | AGGTCGTT |
| TGCTCGTA | AGGTCGCG | GCCTCGGT | TGCTCGCG | TACTCGCA | GAGTCGTT | CGCTCGGG | TGATCGGA | TACTCGGC |
| TCCTCTGG | ACGTCGTG | GACTCGTT | GAGTCGGA | GACTCGCG | GACTCGGT | TGATCGAT | GGCTCTTG | AGCTCTGT |
| CTGTCGGG | ATATCGGG | TCATCTGG | AGATCGTT | AGCTCTGG | AGGTCGGA | CACTCGGT | TGATCGTA | AGGTCGGC |
| GCGTCTGG | TGCTCGCT | GGCTCAGG | GGCTCTGT | TGCTCGGA | TTATCGGA | GGCTCGTT | GCGTCGTG | AAGTCGGG |
| TACTCAGG | TGCTCTGA | AACTCGGG | TCCTCGTG | GCCTCTGG | CACTCGTT | TGATCTGG | GTATCGGC | GAGTCGCT |
| TCATCGGT | GAGTCGTA | GAGTCGAG | AGATCGGG | AGCTCGAG | GCCTCGCG | GTCTCGCC | GTCTCGCG | GCATCGCG |
| GCCTCGCT | CTCTCGCG | ACCTCGTC | CCCTCGCG | GCCTCGCC | CTCTCGGC | TCCTCGCG | CTATCGGC | GCGTCGCG |
| ACCTCGTG | GCCTCGCA | TCCTCGAC | GCATCGCT | GCCTCGTC | ACATCGTC | CTGTCGGC | GTGTCGCC | CTCTCGCC |
| TCATCGAC | CGCTCGGC | GCCTCGTG | CCCTCGGC | GCATCGCC | CCCTCGGT | CACTCGCG | TTCTCGAC | CACTCGCT |
| ACCTCGTT | ACCTCGCG | GTATCGCG | TCCTCGCT | CCCTCGCT | CACTCTGC | GTCTCGCT | GGCTCGCG | GTCTCGGC |
| GCATCGCA | GCATCGGC | TCCTCGTG | CCCTCGTG | CTCTCGGG | ACATCGTG | CACTCGGC | GTATCGGC | TTCTCGCG |
| TCCTCGGC | ACGTCGTC | CCCTCGGG | CGCTCGCT | CGCTCTGC | CTCTCGTG | ACCTCGTA | CCCTCGGA | CCATCGCG |
| TCATCGCG | CCCTCGCA | GCGTCGCT | TCCTCGCC | GCCTCGAC | GGCTCGTG | GCCTCGGG | AGCTCGTG | CGATCGGC |
| AGCTCGTT | GCGTCGCC | TCCTCGGG | CTCTCGGT | CACTCGCC | GCCTCGGT | GTCTCGCA | GCTTCGGG | TCCTCGCA |
| GCTGCGCG | GCATCGTC | GCTTCGGC | ACCTCGGC | CTATCGGG | GTCTCGTG | GGCTCCCC | CCCTCGCC | ACATCGTT |
| TGCTCGCG | GCCTCAGC | CGCTCGGG | CGCTCAGC | GCGTCGCA | ATCTCGCG | CCGTCGCG | TCGTCGAC | GCCGCGCG |
| GCCTCCCG | GCTCCGCG | CCCTCGTC | CACTCGCA | GTCTCGGG | TCCTCGAG | CTGTCGGG | CCATCGGC | GCCTCGGA |
| CGGTCGGC | CCATCGGG | CCGTCGGG | CGCTCCGC | GTGTCGCG | TCCTCGGT | CGCTCGCC | TGCTCACG | CCGTCGGC |
| GCCTCGGC | TGATCGAT | CCCTCAGG | CACTCAGC | CGCTCGCG | CGCTCGCA | GCCTCGTT | GGCTCGGG | GGCTCCCG |
| GGCTCACC | ACGTCGTG | TCCTCGTC | AGCTCGTC | CGCTCGTG | GCCTCTGC | CAGTCGGC | ACCTCGCT | GCCTCGTA |
| TTATCGCG | TGATCGGT | GCCTCGAG | TTCTCGTG | TCATCGCT | AGCTCGGG | GCATCGGG | GGCTCGGT | GACTCGCC |
| AGCTCGGT | TCATCGGC | TGCTCGAC | GCATCGTG | GCCCCGCG | CCCTCTGC | GCATCGAC | ACCTCGGG | TGCTCGGG |
| GACTCGCG | TGTTCGGG | TTCTCGGC | GTGTCGGC | TGCTCGTG | CGCTCGGT | GGCTCGCT | TCATCGGG | CGCTCCGG |
| TACTCGCG | ACATCGCG | CCCTCGAG | ACCTCAGT | TGATCGGG | GCGTCGTC | TCCTCGGA | CCATCGGT | TCCTCGTT |

TABLE 1-continued

| | | | | Deaminated products (8-mers) | | | | |
|---|---|---|---|---|---|---|---|---|
| ACCTCGGT | CCCTCGTT | ACATCGGC | GGTTCGGG | CCATCGCT | TGCTCGCT | TTCTCGCT | TGCTCGTT | CGCTCACG |
| GACTCCCG | GCATCGTT | ACCTCGCA | GCCTCAGG | GTCTCGAG | AGATCGTT | GCGTCGGC | GGCTCGTT | CGATCAGC |
| GCGTCGTG | GCGTCGGG | TTCTCGGG | GGCTCGCA | TTCTCGAG | CGATCGCG | GGCTCGGC | TGCTCGGT | GTCTCGTC |
| CAATCGCG | GGCTCGCC | GTCTCGGA | GTCTCGGT | ACCTCGCC | TGATCGTG | CTCTCGGA | TCGTCGCG | CCCTCGTA |
| CGCTCAGG | GCCCCGCC | TCATCGCA | TGCTCGGC | TCCTCAGG | AGCTCGCG | TCCTCGAT | TGATCGTT | GCATCAGC |
| GCCTCACG | GGCTCACG | ACCTCGGA | CTCTCGAG | GACTCGTG | TCATCGAG | GCGTCGAC | TCCTCGTA | TGCTCGAG |
| TGATCGCG | GCATCGTA | GCCGCGCC | ATGTCGGG | CCGTCGCT | CACTCCGC | AACTCGCG | CGATCCGC | ACACCGTC |
| GCATCGGT | TGATCGGC | AGATCGGG | TACTCGTG | TGCTCGTC | TGCTCGAT | CACTCGTG | TCATCGTG | TCATCGCC |
| CACTCGGT | CCGTCGGT | GCAGCGCG | TACTCGCT | CGCTCCGT | CAATCGGC | GTCTCGAC | CCCTCTGG | CTCCCGGC |
| TGATCGAC | TAATCGAC | TTATCGGC | TACTCGGG | TGCTCGGA | ACCTCGAG | CGATCTGC | GACTCGGG | CGCTCGTT |
| GTATCGGG | CCATCGCC | GTGTCGGG | ACCTCGAC | TCGTCGGG | GACTCGGC | TCGTCGGC | TCATCGAT | ACGTCGTT |
| CCCTCCGC | ATCTCGGG | TGGTCGGG | TTGTCGGG | TACTCGAC | TCCTCAGC | ACCTCGAT | TGATCGCT | GGCTCCCT |
| GCCTCGAT | TGGTCGGC | TTCTCGGA | ACCCCGTC | CGAACGCG | AGCTCGGA | CCCCCGCG | CCATCGGA | TCATCGGT |
| AGCTCGGC | CGATCGCT | GTCTCGTT | AGCTCGCT | AGATCGGT | TTCTCGGT | AGCTCGAG | GGCTCGTC | CGCTCGAG |
| TTCTCGCA | TCGTCGTG | TCATCGTT | CCATCGCA | AGATCGTG | CGGTCGGG | CACTCGGG | GGCTCGAC | CCCTCAGC |
| TTCTCGTC | GCACCGCG | | | | | | | |

TABLE 2

| Corroborating biochemical data for human A3A | | | | | | | | | |
|---|---|---|---|---|---|---|---|---|---|
| Protein | A3A-wt | | | | Protein | A3A-D131T | | | |
| conc. (nM) | A* | C | G | T | conc. (nM) | A | C | G | T |
| 1.6 | 0.0** | 0.0 | 0.0 | 1.1 | 1.6 | 0.0 | 2.1 | 0.0 | 3.3 |
| 3.1 | 0.0 | 0.0 | 0.0 | 1.4 | 3.1 | 0.0 | 1.1 | 0.0 | 3.9 |
| 6.3 | 0.0 | 0.0 | 0.0 | 3.0 | 6.3 | 0.0 | 2.8 | 0.0 | 8.4 |
| 12.5 | 0.0 | 1.9 | 0.0 | 8.8 | 12.5 | 0.0 | 6.5 | 3.2 | 22.1 |
| 25.0 | 1.2 | 10.2 | 3.3 | 51.6 | 25.0 | 4.3 | 22.6 | 4.6 | 69.4 |
| 50.0 | 7.6 | 42.9 | 13.0 | 98.3 | 50.0 | 16.6 | 67.5 | 14.2 | 96.6 |
| 100.0 | 14.4 | 61.5 | 24.0 | 98.6 | 100.0 | 41.2 | 95.8 | 35.6 | 98.6 |
| 200.0 | 16.8 | 68.0 | 20.9 | 98.5 | 200.0 | 47.1 | 97.3 | 42.1 | 96.3 |
| Protein | A3A-D131A | | | | Protein | A3A-D131E | | | |
| conc. (nM) | A | C | G | T | conc. (nM) | A | C | G | T |
| 1.6 | 0.0 | 0.0 | 0.0 | 0.0 | 1.6 | 0.0 | 0.0 | 0.0 | 0.0 |
| 3.1 | 0.0 | 0.0 | 0.0 | 0.0 | 3.1 | 0.0 | 0.0 | 0.0 | 0.0 |
| 6.3 | 0.0 | 0.0 | 0.0 | 0.0 | 6.3 | 0.0 | 3.7 | 0.0 | 0.0 |
| 12.5 | 0.0 | 0.0 | 0.0 | 0.0 | 12.5 | 2.9 | 9.1 | 2.0 | 1.7 |
| 25.0 | 3.2 | 2.9 | 2.4 | 1.8 | 25.0 | 8.6 | 34.4 | 7.4 | 6.7 |
| 50.0 | 8.7 | 10.1 | 4.0 | 3.7 | 50.0 | 36.6 | 90.8 | 30.8 | 27.3 |
| 100.0 | 17.3 | 25.1 | 8.3 | 8.3 | 100.0 | 54.5 | 97.1 | 47.6 | 46.7 |
| 200.0 | 24.5 | 33.0 | 11.2 | 10.6 | 200.0 | 58.0 | 97.0 | 35.1 | 51.3 |

*Minus 1 position nucleotide
**Values are percent product.

TABLE 3

X-ray data collection and refinement statistics

| | A3A-ssDNA (pdb 5SWW) | A3Bctd*-ssDNA (pdb 5TD5) |
|---|---|---|
| Data collection | | |
| Space group | P222$_1$ | P6$_4$22 |
| Cell dimensions | | |
| a, b, c (Å) | 90.15, 90.20, 167.26 | 96.41, 96.41, 84.88 |
| α, β, γ (°) | 90, 90, 90 | 90, 90, 120 |
| Resolution (Å) | 47.42-3.15 (3.26-3.15)$^a$ | 59.52-1.72 (1.78-1.72) |
| R$_{merge}$ (%) | 19.1 (112.1) | 5.4 (127.5) |
| R$_{meas}$ (%) | 21.1 (123.8) | 5.6 (133.2) |
| R$_{pim}$ (%) | 8.9 (51.9) | 1.5 (37.8) |
| I/σ(I) | 8.4 (1.4) | 35.3 (2.1) |
| CC$_{1/2}$ | 0.991 (0.693) | 0.999 (0.783) |
| Completeness (%) | 99.6 (99.0) | 99.7 (97.2) |
| Redundancy | 5.5 (5.6) | 12.7 (11.8) |
| Refinement$^b$ | | |
| Resolution (Å) | 47.42-3.15 (3.26-3.15) | 59.52-1.72 (1.78-1.72) |
| No. reflections | 24189 (2339) | 25281 (2417) |
| R$_{work}$/R$_{free}$ (%) | 21.0(30.3)/26.3(35.1) | 18.1(31.9)/21.2(29.4) |
| No. atoms | 6597 | 1712 |
| Protein/DNA | 6553 | 1578 |
| Ligand/ion | 24/4 (GOL/Zn$^{2+}$) | 24/1/9/2 (EG/Zn$^{2+}$/I$^-$/Cl$^-$) |
| Water | 16 | 98 |
| B factors (Å$^2$) | 73.54 | 45.97 |
| Protein/DNA | 73.58 | 45.24 |
| Ligand/ion | 82.77 | 76.46 |
| Water | 37.41 | 46.58 |
| R.m.s. deviations | | |
| Bond lengths (Å) | 0.002 | 0.015 |
| Bond angles (°) | 0.45 | 1.20 |

$^a$Values in parentheses are for highest-resolution shell.
$^b$Each structure is from one crystal.

Single-Stranded DNA (ssDNA) Oligonucleotides.

Figure 10A:
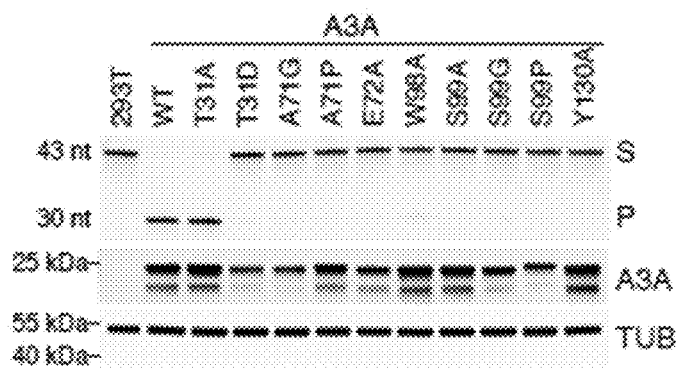
FIGS. 10A-10C provide corroborating biochemical data for human A3A.

The ssDNA oligonucleotides for co-crystallization with A3A and A3Bctd* were 5'-AAAAAAATCGGGAAA (SEQ ID NO:17) and 5'-TTTTCAT, respectively (Integrated DNA Technologies). The unbiased experimental approach for identifying the former sequence is described below, and the latter is based on the fact that 5'-TCA is the most commonly mutated APOBEC signature motif in cancer (Helleday et al., supra; Roberts and Gordenin, supra; and Swanton et al., supra). 3'-fluorescently labeled ssDNA oligonucleotides for in vitro DNA deamination experiments were obtained from Integrated DNA Technologies or Midland Certified Reagent Company. The ssDNA oligonucleotide substrates used in FIG. 5E were 5'-AAAAAAAATCGGGAAAAAAA-3'-FAM (SEQ ID NO:3), 5'-AAAAAAAA[dU]CGGGAAAAAAA-3'-FAM (SEQ ID NO:4), 5'-AAAAAAAA[iSuper-dT]CGGGAAAAAAA-3'-FAM (SEQ ID NO:5), and 5'-AAAAAAAA[5-F-dU]CGGGAAAAAAA-3'-FAM (SEQ ID NO:6) (labeled dT, dU, Super T, and 5FdU, respectively). The ssDNA oligonucleotide substrate used in FIG. 10A was 5'-ATTATTATTATTCAAATGGATTTATTTATTTATTTATTTATTT-3'-FAM (SEQ ID NO:18), the same except (A, C, G, or T)CA as trinucleotide targets in FIG. 10B. 5-Nitroindole containing ssDNA substrates were purchased from Integrated DNA Technologies (Coralville, Iowa) as desalted oligonucleotides and characterized by LC-MS on an Agilent 1100 series HPLC instrument equipped an Agilent MSD SL ion trap mass spectrometer. A full list of ssDNA oligonucleotides used for site-directed mutation is provided in TABLE 4.

TABLE 4

Oligonucleotides used in the described studies

Crystallization ligands

| | |
|---|---|
| APOBEC3A ligand | AAAAAAATCGGGAAA (SEQ ID NO: 17) |
| APOBEC3B ligand | TTTTCAT |

Deaminase assay substrates (all labeled with fluorescein at the 3' end)

| | |
|---|---|
| -1 ACA | ATTATTATTATACAAATGGATTTATTTATTTATTTATTT (SEQ ID NO: 23) |
| -1 CCA | ATTATTATTATCCAAATGGATTTATTTATTTATTTATTT (SEQ ID NO: 24) |
| -1 GCA | ATTATTATTATGCAAATGGATTTATTTATTTATTTATTT (SEQ ID NO: 25) |
| -1 TCA | ATTATTATTATTCAAATGGATTTATTTATTTATTTATTT (SEQ ID NO: 26) |
| -1 Thymine | AAAAAAAATCGGGAAAAAAA (SEQ ID NO: 3) |
| -1 Uracil | AAAAAAAAUCGGGAAAAAAA (SEQ ID NO: 4) |
| -1 Super T | AAAAAAAA(sT)CGGGAAAAAAA (SEQ ID NO: 5) |
| -1 5-fluoruracil | AAAAAAAA(5FU)CGGGAAAAAAA (SEQ ID NO: 6) |
| +1 to +3 5-nitroindole | AAAAAAAATCXXXAAAAAAA (SEQ ID NO: 27) |

Deep Deamination Oligos

| | |
|---|---|
| Deep Deamination | GTAGTTAGTAGGATTGATTGAGNNNNCNNNTGATTGATGGATTGAGTAGTG (SEQ ID NO: 28) |
| 5' Illumina Adaptor | aatgatacggcgaccaccgagatctacactattccctacacgacgctcttccgatctTAGTTAGTAGGATTGATTGAG (SEQ ID NO: 29) |
| Barcode Adaptor 1 | caagcagaagacggcatacgagatATTGGCgtgactggagttcagacgtgtgctatccgatctCACTACTCAATCCATCAATCA (SEQ ID NO: 30) |
| Barcode Adaptor 2 | caagcagaagacggcatacgagatTTGACTgtgactggagttcagacgtgtgctcttccgatctCACTACTCAATCCATCAATCA (SEQ ID NO: 31) |

TABLE 4-continued

Oligonucleotides used in the described studies

| | |
|---|---|
| Barcode Adaptor 3 | caagcagaagacggcatacgagatTACAAGgtgactggagttcagacgtgtgctcttccgatctCACTACTCAATCCATCAATCA (SEQ ID NO: 32) |
| Barcode Adaptor 4 | caagcagaagacggcatacgagatGGAACTgtgactggagttcagacgtgtgctcttccgatctCACTACTCAATCCATCAATCA (SEQ ID NO: 33) |
| Barcode Adaptor 5 | caagcagaagacggcatacgagatCACTGTgtgactggagttcagacgtgtgctcttccgatctCACTACTCAATCCATCAATCA (SEQ ID NO: 34) |
| Barcode Adaptor 6 | caagcagaagacggc atacgagatTGACATgtgactggagttcagacgtgtgctcttccgatctCACTACTCAATCCATCAATCA (SEQ ID NO: 35) |
| Barcode Adaptor 7 | caagcagaagacggc atacgagatTTTCACgtgactggagttcagacgtgtgctcttccgatctCACTACTCAATCCATCAATCA (SEQ ID NO: 36) |
| Barcode Adaptor 8 | caagcagaagacggcatacgagatCGAAACgtgactggagttcagacgtgtgctatccgatctCACTACTCAATCCATCAATCA (SEQ ID NO: 37) |
| Barcode Adaptor 9 | caagcagaagacggcatacgagatCGTGATgtgactggagttcagacgtgtgctatccgatctCACTACTCAATCCATCAATCA (SEQ ID NO: 38) |
| Barcode Adaptor 10 | caagcagaagacggcatacgagatAAGCTAgtgactggagttcagacgtgtgctcttccgatctCACTACTCAATCCATCAATCA (SEQ ID NO: 39) |
| Universal reverse | CACTACTCAATCCATCAATCA (SEQ ID NO: 40) |

| SDM oligos | Forward | Reverse |
|---|---|---|
| T31A | CATTGGAAGGCATAAGgccTACCTGTGCTACG (SEQ ID NO: 41) | CGTAGCACAGGTAggcCTTATGCCTTCCAATG (SEQ ID NO: 42) |
| T31D | GGCATTGGAAGGCATAAGgacTACCTGTGCTACGAAGTG (SEQ ID NO: 43) | CACTTCGTAGCACAGGTAgtcCTTATGCCTTCCAATGCC (SEQ ID NO: 44) |
| A71G | TTACGGCCGCCATGgGGAGCTGCGCTTC (SEQ ID NO: 45) | GAAGCGCAGCTCCcCATGGCGGCCGTAA (SEQ ID NO: 46) |
| A71P | TTACGGCCGCCATCcGGAGCTGCGCTTC (SEQ ID NO: 47) | GAAGCGCAGCTCCggATGGCGGCCGTAA (SEQ ID NO: 48) |
| W98A | TGGTTCATCTCCgcGAGCCCCTGCTTC (SEQ ID NO: 49) | GAAGCAGGGGCTCgcGGAGATGAACCA (SEQ ID NO: 50) |
| W98F | TGGTTCATCTCCttcAGCCCCTGCTTC (SEQ ID NO: 51) | GAAGCAGGGGCTgaaGGAGATGAACCA (SEQ ID NO: 52) |
| W98Y | TGGTTCATCTCCtacAGCCCCTGCTTC (SEQ ID NO: 53) | GAAGCAGGGGCTgtaGGAGATGAACCA (SEQ ID NO: 54) |
| S99G | GTTCATCTCCTGGgGCCCCTGCTTCTCC (SEQ ID NO: 55) | GGAGAAGCAGGGGCcCCAGGAGATGAAC (SEQ ID NO: 56) |
| S99P | GTTCATCTCCTGGccACCCTGCTTCTCC (SEQ ID NO: 57) | GGAGAAGCAGGGTggCCAGGAGATGAAC (SEQ ID NO: 58) |
| Y130F | GCTGCCCGCATCTtTGATTACGACCCC (SEQ ID NO: 59) | GGGGTCGTAATCAaAGATGCGGGCAGC (SEQ ID NO: 60) |
| Y130A | GCTGCCCGCATCgcTGATTACGACCCC (SEQ ID NO: 61) | GGGGTCGTAATCAgcGATGCGGGCAGC (SEQ ID NO: 62) |
| D131E | GCCCGCATCTATGAgTACGACCCCCTA (SEQ ID NO: 63) | TAGGGGGTCGTAcTCATAGATGCGGGC (SEQ ID NO: 64) |
| D131A | GCCCGCATCTATGcTTACGACCCCCTA (SEQ ID NO: 65) | TAGGGGGTCGTAAgCATAGATGCGGGC (SEQ ID NO: 66) |
| D131T | GCCCGCATCTATAcTTACGACCCCCTA (SEQ ID NO: 67) | TAGGGGGTCGTAAgtATAGATGCGGGC (SEQ ID NO: 68) |
| Y132F | CGCATCTATGATTtCGACCCCCTATAT (SEQ ID NO: 69) | ATATAGGGGGTCGaAATCATAGATGCG (SEQ ID NO: 70) |
| Y132A | CGCATCTATGATgcCGACCCCCTATAT (SEQ ID NO: 71) | ATATAGGGGGTCGgcATCATAGATGCG (SEQ ID NO: 72) |

Deep Deamination Experiments to Determine an Optimal A3A Target Site.

Studies were conducted to determine whether deep sequencing of a target ssDNA oligonucleotide with a single cytosine flanked by degenerate Watson-Crick nucleobases could be used to determine an optimal A3A target site. First, a ssDNA substrate oligonucleotide containing the sequence 5'-NNNNCNNN flanked by cytosine-free 22 and 21 nucleotide regions was synthesized (Integrated DNA Technologies). This yielded a pool with 16,384 unique substrate sequences. Second, wild-type human A3A was purified from semi-confluent 293T cells transfected with a pcDNA4/TO-A3Ai-2xStrep3xFlag (SF) expression vector (Starrett et al., supra). Cells were harvested 48 hours post-transfection and lysed in 50 mM Tris-HCl pH 8.0, 1% (v/v) NP-40, 150 mM NaCl, 0.5% (w/v) deoxycholate, 0.1% (w/v) SDS, 5 mM EDTA, RNase A, 1× EDTA-free Protease Inhibitor Cocktail (Roche), and then further disrupted by sonication. A3A-SF was purified using Strep-tactin resin (IBA). Samples were washed in high salt buffer (20 mM Tris-HCl pH 7.5, 1.5 mM $MgCl_2$, 1 M NaCl, 0.5 mM DTT and 5% glycerol) followed by low salt buffer (same as the high salt buffer except with 150 mM NaCl) and final wash buffer (100 mM Tris-HCl pH 7.5, 150 mM NaCl) and eluted using 2.5 mM desthiobiotin. Purified protein was fractionated using 4-20% SDS-PAGE and quantified by staining with Coomassie brilliant blue (Sigma).

Third, titration experiments were conducted with recombinant A3A-SF to determine single-hit reaction conditions. This amount of enzyme was then incubated with 8 pmol of the substrate oligonucleotide pool for 1 hour at 37° C. in 50 mM Tris pH 7.5, 75 mM NaCl. Two (2) pmol of the treated pool was annealed to appropriate 3'-barcoded adaptor using T4 DNA Polymerase at 12° C. for 20 minutes. A universal 3'-adapter was then added to the duplex using Phusion DNA polymerase (New England Biolabs, Ipswich, Mass.). Products were purified using a GeneJET PCR purification kit (ThermoFisher Scientific), analyzed by 20% native PAGE, and diluted to appropriate concentrations for deep sequencing.

The reaction products were analyzed using 2×50 nt paired-end reads (Illumina HiSeq 2500, University of Minnesota Genomics Center). Reads were paired using FLASh (online at ccb.jhu.edu/software/FLASH/). Data processing was performed using a locally installed FASTX-Toolkit (online at hannonlab.cshl.edu/fastx_toolkit/). FASTX trimmer was used to trim the 5' and 3' constant regions from sequences. Trimmed sequences were then filtered for high-quality reads using FASTQ quality filter. Sequences with a Phred quality score less than 30 (99.9% base calling accuracy) at any position were eliminated. Pre-processed sequences were then further analyzed using the FASTAptamer toolkit (online at burkelab.missouri.edu/fastaptamer.html). FASTAptamer-Count was used to count the number of times each sequence was sampled from the population. Each sequence was then ranked and sorted based on overall abundance, normalized to the total number of reads in each population, and directed into FASTAptamer-Enrich. FASTAptamer-Enrich calculates the fold-enrichment ratios from a starting population (no enzyme control) to a selected population (incubation with A3A or other enzymes). After generating the enrichment file, mutated sequences specific to the A3A reaction versus control reactions were analyzed using WebLogo design software (Crooks et al., *Genome Res* 14:1188-1190, 2004). Logo error bars are twice the sample correction value (Gaborek, *Biophys J* 103:2513-2520, 2012).

A3A Expression Constructs and DNA Deamination Activity Assays.

The pcDNA3.1-A3Ai-myc-His expression construct is described elsewhere (Stenglein et al., supra; Li et al., *ACS Chem Biol* 7:506-517, 2012; and Carpenter et al. 2012, supra). Derivatives were constructed by site-directed mutagenesis and verified by DNA sequencing. The activities of a subset of the A3A mutant constructs reported here have been described elsewhere (Byeon et al., *Nat Commun* 4:1890, 2013; Byeon et al., *Biochemistry* 55:2944-2959, 2016; Caval et al., *Nucleic Acids Res* 43:9340-9349, 2015; Chen et al., *Curr Biol* 16:480-485, 2006; Logue et al., *PLoS One* 9:e97062, 2014; Mitra et al., *Nucleic Acids Res* 42:1095-1110, 2014; Fu et al., *Biochem J* 471:25-35, 2015; Narvaiza et al., *PLoS Pathog* 5:e1000439, 2009; and Bulliard et al., *J Virol* 85:1765-1776, 2011). Semi-confluent 293T cells in 6 well plates were transfected with 1 μg plasmid and harvested after 48 hours to allow time for enzyme expression. Soluble whole cell extracts (WCE) were prepared by pelleting the cells and resuspending them in HED buffer (20 mM HEPES pH 7.4, 5 mM EDTA, 100 μg $ml^{-1}$ RNase A, 1 mM DTT, 10% glycerol, and Roche Complete protease inhibitors). Resuspended cell pellets were freeze-thawed then rotated for 1 hour at room temperature followed by water bath sonication for 20 minutes. Cell debris was pelleted and the clarified lysate was used for DNA deaminase activity assays. 5 μl WCE with desired A3A construct (or control) were mixed with 5 μl HED buffer containing 1.6 μM fluorescently labeled ssDNA (sequences above). Reactions were then allowed to progress for 1 hour at 37° C., followed by treatment with 120 nM recombinant human UNG2 (uracil DNA glycosylase) for 10 minutes at 37° C., and treatment with 100 mM NaOH for 10 minutes at 95° C. (Li et al., supra; and Carpenter et al. 2012, supra). Reaction products were separated by 15% denaturing PAGE and scanned on a Typhoon FLA 7000 imager (GE Healthcare). A3A-myc-His expression was verified by immunoblotting using primary rabbit anti-cMYC antibody at 1:3000 (Sigma, C3956) and secondary goat anti-rabbit IgG-Alexa Fluor 680 at 1:10,000 (Life Technologies, A21076). Tubulin expression was used as a loading control, and staining was done with primary mouse anti alpha-Tubulin at 1:80,000 (Sigma, B512) followed by secondary goat anti-mouse IR-Dye 800CW at 1:10,000 (LI-COR, 926-32210). Washed immunoblots were imaged using a LI-COR Odyssey imaging system.

Recombinant A3A-myc-His and mutant derivatives were expressed in 293T cells and purified as described by nickel affinity chromatography (Stenglein et al., supra; Li et al., supra; and Carpenter et al. 2012, supra). Activity assays were conducted as outlined above, except reactions were initiated by adding 5 μl of enzyme (2-fold dilutions starting at 200 nM) to 5 μl of 50 mM NaCl, 10 mM HEPES buffer (pH 7.4) containing 1.6 μM fluorescently labeled ssDNA (sequences above). Reactions progressed 1 hour at 37° C. and processed and quantified as described above.

Data Availability.

The coordinates and structure factors for the A3A-ssDNA and A3Bctd*-ssDNA complexes have been deposited in the Protein Data Bank (online at rcsb.org/pdb/home/home.do) under accession codes 5SWW and 5TD5, respectively. Source data for FIG. 1 are provided in TABLE 1, and source data for FIG. 10C are provided in TABLE 2.

Example 2—Optimal Target for A3A-Catalyzed C-to-U Deamination in ssDNA

A3A is a globular enzyme with a single zinc-coordinating active site, and it has proven to be the most potent human DNA cytosine deaminase (Carpenter et al. 2012, supra; and Caval et al. 2015, supra). The extended substrate requirements for the enzyme have not previously been determined in an unbiased manner. Thus, to elucidate the mechanism for binding ssDNA and preferring 5'-TC dinucleotide targets, the crystal structure of human A3A bound to ssDNA was solved. The optimal substrate for wild-type A3A catalysis was first determined by performing deep deamination experiments with ssDNA containing a fixed target cytosine flanked on the 5' and 3' sides by 4 and 3 randomized bases, respectively (FIG. 1). Enzymatic reactions were allowed to proceed to ~10% completion (single hit kinetics) and, following conversion to double-stranded DNA with adaptors, deep-sequencing was used to determine the preferred bases flanking C-to-U deamination events (detected as C-to-T events). An analysis of >10,000 reads and 641 mutagenic events revealed a near-complete enrichment for T at the 5'-1 position relative to the target C(0), a strong preference for a cytosine or purine nucleobase at the −2 position, and an unexpected preference for G at all 3' positions (+1 to +3) (FIG. 1). This analysis informed the design of an optimal ssDNA substrate for co-crystallization studies, 5'-AAAAAAATCGGGAAA (SEQ ID NO:17).

Example 3—A3A-ssDNA Structure Reveals a Novel U-Shaped Binding Conformation

The optimal ssDNA substrate for A3A was co-crystallized with human A3A purified from E. coli. This protein represents the wild-type enzyme apart from a 4 residue C-terminal truncation to improve solubility and a single amino acid substitution of the catalytic glutamate (E72A) to prevent substrate turnover and bacterial genotoxicity (FIG. 2). The 3.1 Å resolution A3A-ssDNA structure has 4 monomeric complexes in the asymmetric unit and each shows clear electron density for either 5 (5'-ATCGG) or 6 (5'-ATCGGG) nucleotides centered on the target cytosine (TABLE 3, FIG. 3). A superposition shows near-identical conformations of all four proteins as well as the positioning of the −1 T and the target C(0) nucleotides, as well as some variation in the locations of bases outside the 5'-TC dinucleotide core (FIG. 3).

Figure 4A:
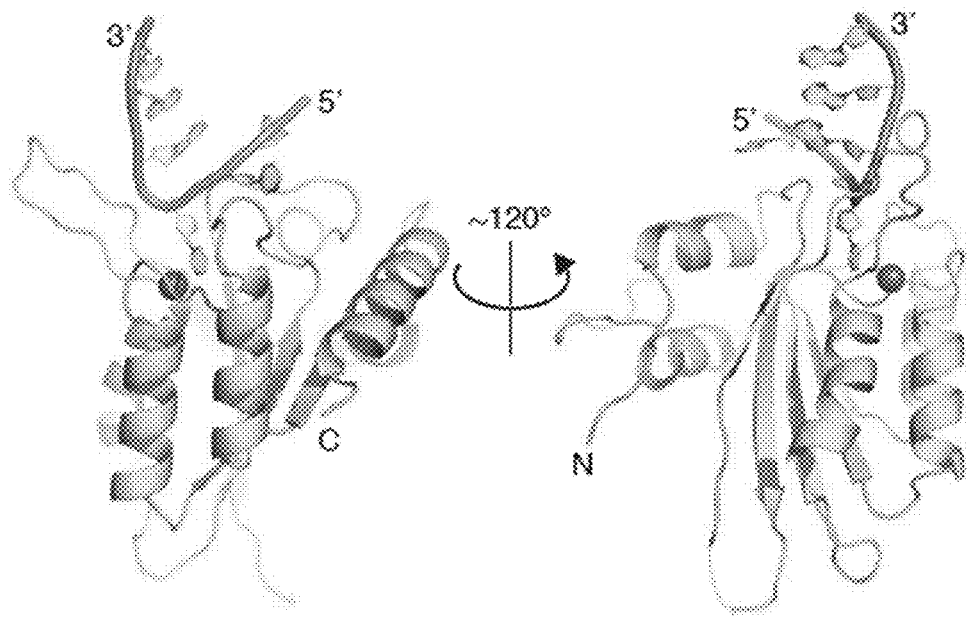
FIGS. 4A-4D show the crystal structure of human A3A bound to ssDNA with a preferred 5'-TCG deamination target motif.
Figure 4B:
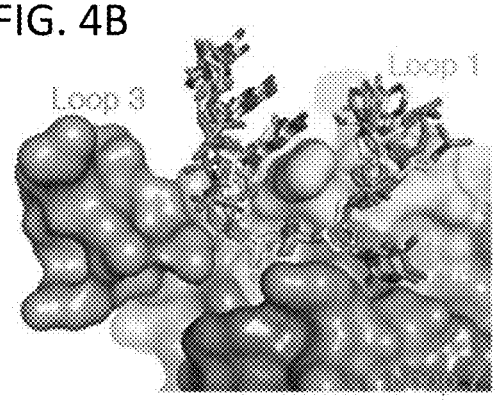
Figure 4C:
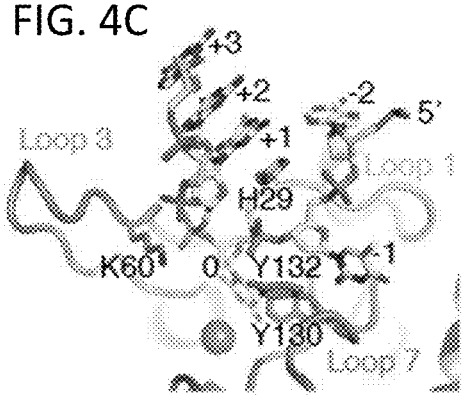
Figure 4D:
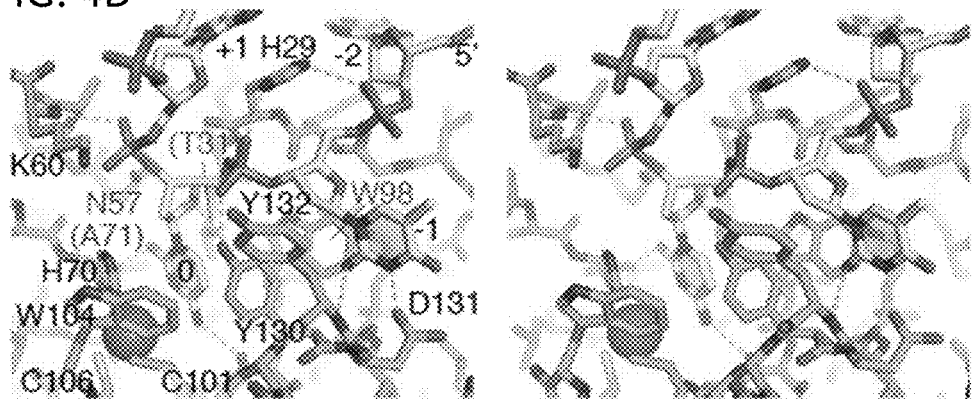

The A3A-bound ssDNA adopts a U-shaped conformation anchored by the target cytosine and the −1 thymine, with up- and down-stream ssDNA bent away from the active site (FIG. 4A). At the bottom of the 'U', the target cytosine and the 5' thymine bases are flipped out toward the protein with the sugar-phosphate backbone rotated with respect to those of the flanking nucleotides (FIGS. 4A-4D and FIG. 3). The two flipped-out nucleotides fit between loops 1 and 7 and are stabilized by extensive van der Waals contacts with Trp98 at the base of the groove and hydrogen bonds to backbone phosphates on the 5' and 3' sides of the target cytosine, respectively, by the side chain of Tyr130 in loop 7 and Asn57 preceding loop 3 (FIGS. 4B-4D). Across the ssDNA-binding groove and opposite Tyr130, His29 from loop 1 fits inside the 'U' and donates hydrogen bonds to the backbone phosphates of both the target cytosine and 5' thymine. The simultaneous hydrogen-bonding of His29 suggests that this side chain interacts with DNA optimally when doubly protonated, consistent with the reported pH-dependence of A3A and A3G ssDNA deamination activity (Harjes et al., J Virol 87:7008-7014, 2013; and Pham et al., J Biol Chem 288:29294-29304, 2013). The His29 side chain also stacks with the +1 base and makes van der Waals contacts with the nucleotide at −2 position, where the +1 and −2 bases may be close enough to interact. Thus, His29 appears to serve as a scaffold to stabilize ssDNA substrates in the 'U-shaped' conformation. The +2 and +3 bases linearly stack on the +1 base analogous to a B-form double-stranded DNA (FIGS. 4B and 4C).

Example 4—A3B-ssDNA Structure and the Mechanism of Local Target Recognition

To improve crystallographic resolution and increase relevance to cancer, a crystal structure of the human A3B catalytic domain bound to ssDNA was solved. A3B is a nuclear-localizing enzyme strongly implicated in cancer mutagenesis, including associations with poor clinical outcomes for estrogen receptor-positive breast cancer, multiple myeloma, and lung cancer (Sieuwerts et al., Horm Cancer 5:405-413, 2014; Law et al., Sci Adv 2:e1601737, 2016; Cescon et al., Proc Natl Acad Sci USA 112:2841-2846, 2015; Yan et al., J Cancer 7:618-625, 2016; and Walker et al., J Clin Oncol 33:3911-3920, 2015). A3B is double-domain enzyme with an N-terminal pseudo-catalytic domain and a C-terminal catalytic domain (Harris and Dudley, Virology 479-480C: 131-145, 2015; Malim and Bieniasz, supra; and Simon et al., supra). The catalytic domain has 92% amino acid sequence identity with A3A, with the majority of differences occurring in solvent-exposed surfaces including loop regions (FIG. 2). Crystals were obtained using a catalytic mutant derivative (E255A) of the A3B variant with loop 1 from A3A and near wild-type activity (A3Bctd-QMΔloop3-A3Aloop1, referred to hereafter as A3Bctd*; Shi et al., supra) and a 7-mer ssDNA (5'-TTTTCAT) containing the most frequently mutated APOBEC motif in cancer (5'-TCA; Helleday et al., supra; Roberts and Gordenin, supra; and Swanton et al., supra).

Figure 6B:
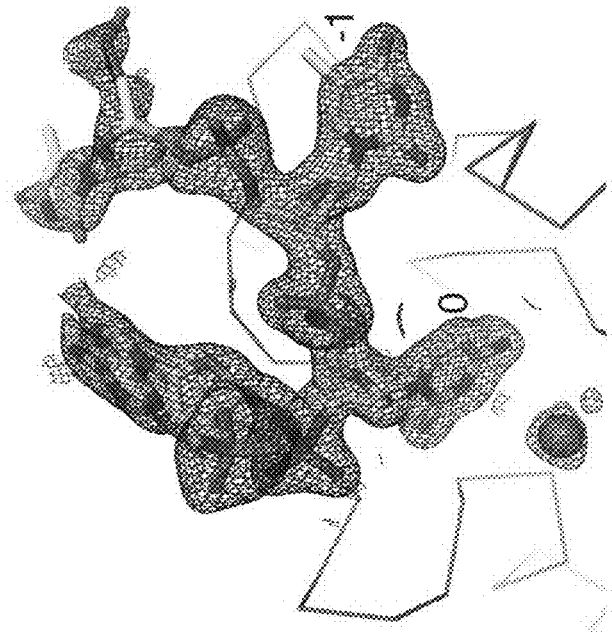
FIGS. 6A and 6B are additional representations of A3Bctd*-ssDNA complexes.
Figure 6A:
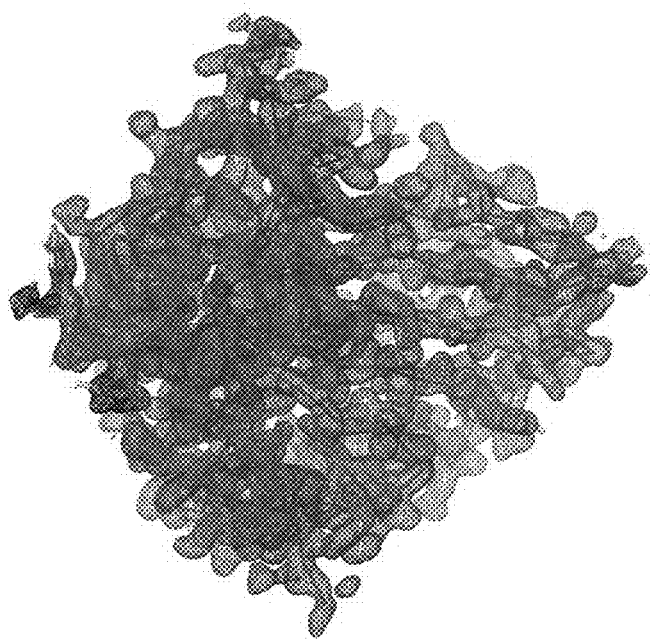
Figure 8A:
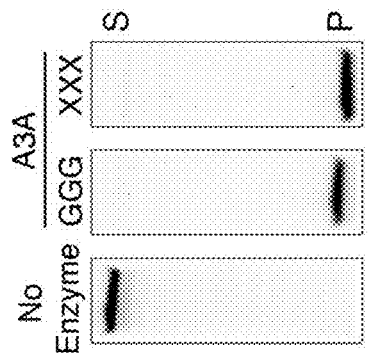
FIGS. 8A-8D show the importance of hydrogen-bonding potential of ssDNA nucleobases +1 to +3.
Figure 8C:
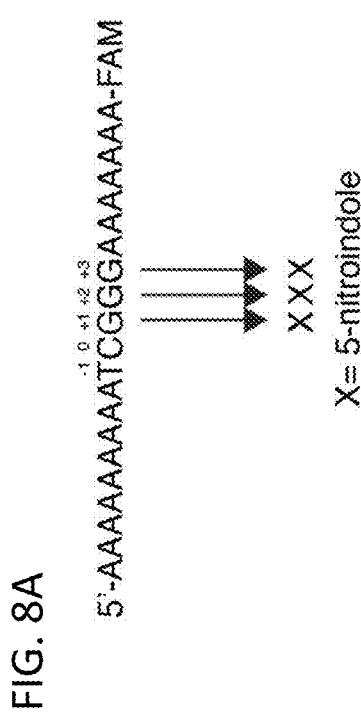
Figure 8B:
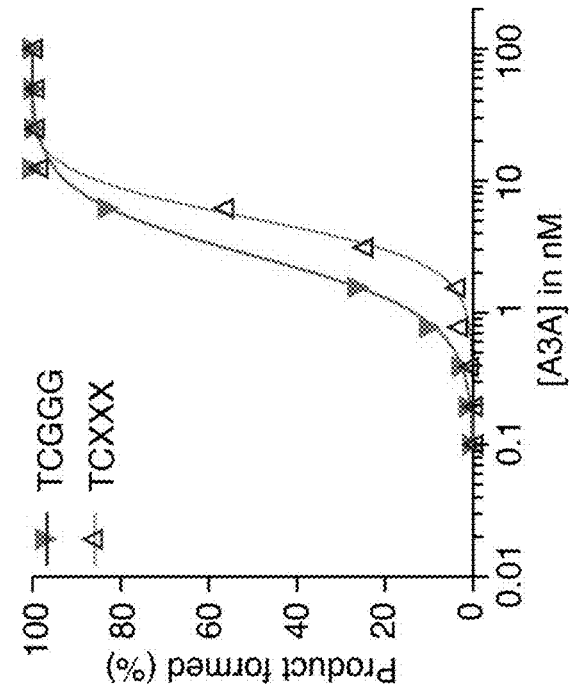
Figure 8D:
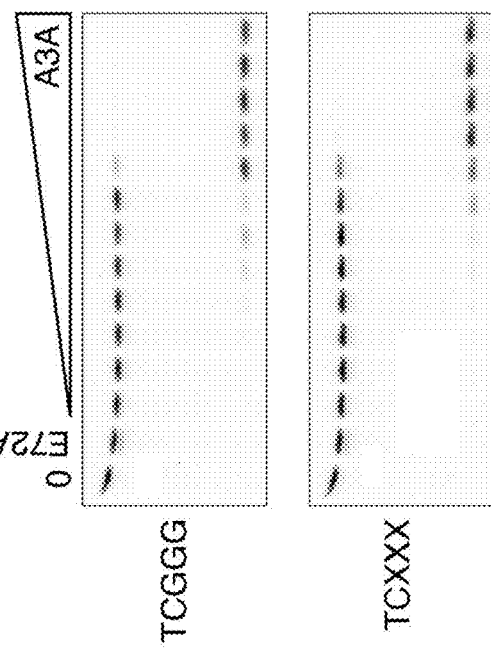

The 1.7 Å resolution structure of the A3Bctd*-ssDNA complex has a single nucleoprotein complex in the asymmetric unit and clear electron density for 4 nucleotides (5'-TTCA) (FIGS. 5A and 6, and TABLE 3). Despite the different enzyme-ssDNA combination, the overall DNA conformation is also 'U-shaped' and highly similar to that in the DNA-bound A3A structure (FIG. 5B). The target cytosine is inserted deep into the active site pocket, which contains a zinc ion coordinated by His253, Cys284, and Cys289 (equivalent to A3A residues His70, Cys101, and Cys106; A3Bctd*-ssDNA vs. A3A-ssDNA superposition in FIG. 5B and A3Bctd* active site electron density in FIG. 5C). The amino group at the C4 position of the pyrimidine ring donates a hydrogen bond to the backbone carbonyl of Ser282 (Ser99) and is positioned to form the zinc-stabilized tetrahedral intermediate characteristic of the hydrolytic deamination reaction (FIG. 5C). The carbonyl oxygen of the cytosine base accepts a hydrogen bond from the backbone amide group of Ala254 (Ala71). The non-polar edge (C5 and C6) of the cytosine base makes a T-shaped π-stacking interaction with Tyr313 (Tyr130). Cytosine ring positioning is further stabilized by a hydrogen bond between the O4' of the deoxyribose ring and Thr214 (Thr31) as well as nucleobase sandwiching between Thr214 (Thr31) and His253 (His70).

The −1 thymine nucleotide fits in a hydrophobic pocket formed by Trp281, Tyr313, and Tyr315 (Trp98, Tyr130, and Tyr132), where the N3 and O2 atoms of the pyrimidine are hydrogen-bonded to the side chain of Asp314 (Asp131) and the backbone amide group of Tyr315 (Tyr132), respectively. These interactions explain the strong selectivity for the 5'-TC motif by A3B and A3A (FIG. 5B). Further, the higher resolution A3Bctd*-ssDNA structure revealed a water-mediated interaction between Asp314 and the O4 carbonyl group of the thymine ring, which may be an additional selectivity factor (FIG. 5D). Interestingly, the 5-methyl group of the −1 T is pointed away from the protein and does not interact with the enzyme or the ssDNA substrate. Consistent with this observation, ssDNA substrates with 5-methyl substituted deoxy-thymidine analogs at the −1 position were deaminated efficiently by A3A [2'-deoxyuridine (dU), 5-hydroxybutynl-2'-deoxyuridine (Super T), and 5-fluorodeoxyuridine (5FdU); FIG. 5E]. A3A has indistinguishable activities in dose response experiments with normal T versus Super T at the −1 position, which further validates the observed positioning of the −1 thymine in the bound ssDNA and shows that the methyl group does not contribute to the intrinsic 5'-TC target sequence preference (FIG. 7). The stereoview provides a comprehensive visualization of all of these structural features (FIG. 5F).

Example 5—Interactions with Nucleotides Flanking the 5'-TC Target Motif

Outside the central 5'-TC motif, A3A and A3Bctd* make limited direct interactions with nucleobases of the bound ssDNA, consistent with the degeneracy of these positions in deep deamination experiments (FIGS. 4 and 5). Arg28 in loop 1 of A3A interacts with an adenine at the −2 position, whereas the homologous Arg211 in A3Bctd* interacts with a thymine at the same position. This less specific base contact is consistent with A3A R28A and A3B R211A retaining robust ssDNA deaminase activity (Shi et al., supra) and the occurrence of multiple bases at the −2 position in the A3A deep deamination reaction (FIG. 1). In addition, Lys30 in A3A is positioned close to the major groove edge of the +1 guanine base, potentially contributing to the preference for a purine at this position. The corresponding residue Gln213 of A3B may similarly account for the reported +1 adenine preference (Burns et al. 2013a, supra), although the A3Bctd*-ssDNA complex could not show this potential contact due to a likely influence of crystal packing in the positioning of +1 adenine and the necessary engineering of loop 1 residues to facilitate crystallization of the A3Bctd*-ssDNA complex.

To probe whether interactions with any of the linearly stacked nucleobases at +1 to +3 positions are important in ssDNA engagement, A3A activity was assayed using normal versus 5-nitroindole substituted ssDNA substrates. 5-nitroindole is a universal base analog that stacks like a canonical nucleobase but lacks hydrogen-bonding capabilities. A3A had robust DNA cytosine deaminase activity with a ssDNA substrate containing 5-nitroindole substitutions for +1 to +3 positions, only about 2-fold lower than that with an optimal ssDNA substrate with deoxy-guanosines at the same positions (FIG. 8). These data indicated that base stacking or hydrophobic interactions between the +1 to +3 nucleotides may be more relevant for the ssDNA deamination mechanism than nucleobase hydrogen-bonding with the enzyme.

The loop 3 region in both the A3A and A3Bctd* complexes makes either direct or water-mediated hydrogen bonds via the peptide main chain atoms with the backbone phosphate of +1 nucleotide (FIGS. 4D, 5B, and 5F). In addition, A3A loop 3 Lys60 points toward a mid-point between the backbone phosphate groups of +1 and +2 guanine nucleotides suggesting a stabilizing interaction, although the ζ amino group is not within direct hydrogen bonding distance to either phosphate. The 5' and 3' nucleotides farther from the target cytosine, 5' of −1 and 3' of +1 positions, are beyond bonding potential with the enzyme, which is consistent with biochemical footprinting studies (Rausch et al., *J Biol Chem* 284:7047-7058, 2009), HIV-1 hypermutation experiments (Harris et al., *Cell* 113:803-809, 2003; Yu et al., *Nat Struct Mol Biol* 11:435-442, 2004; and Kim et al., *PLoS Pathog* 10:e1004281, 2014), and cancer mutation spectra analyses (Burns et al. 2013b, supra); Kim et al., *PLoS Pathog* 10:e1004281, 2014; and Roberts et al., *Nat Genet* 45:970-976, 2013) described elsewhere. However, ssDNA lengths greater than 3 nucleotides appear to be required for full deaminase activity, indicating that non-specific contacts also may be important (Mitra et al., supra).

Example 6—Comparisons of Apo and ssDNA-Bound Structures

A comparison of the ssDNA-bound structures with A3A and A3Bctd crystal structures described elsewhere (Bohn et al., *Structure* 21:1042-1050, 2013; and Shi et al., supra) yields additional mechanistic insights into how the activities of these enzymes are likely to be regulated (FIG. 9). The conserved active site and zinc-coordinating residues are virtually unchanged, consistent with the strong preferences of these enzymes (and other family members) for normal (unmodified) cytosine nucleobases in ssDNA and indicating that the surrounding loop regions govern ssDNA binding activity and local dinucleotide targeting. Indeed, comparisons of the native and ssDNA-bound structures reveal large side chain reorientations for His29 and Tyr132 of A3A, and loop 1 rearrangement and Tyr315 reorientation in A3B. As noted above, A3A His29 provides multiple contacts that enable the ssDNA to adopt the 'U-shaped' conformation. The analogous histidine in the A3Bctd*-ssDNA structure has a similar scaffolding conformation, although it should be noted that this residue and most of loop 1 are derived from A3A (necessary alteration for crystallization purposes). Further structural and biochemical studies may be needed to fully understand the mechanism of ssDNA engagement by wild-type A3B, where one of the three arginines (Arg210, Arg211, or Arg212) in wild-type A3B loop 1 may have a stabilizing function analogous to A3A His29.

Figures 9A, 9B, 9C, 9D, 9E:
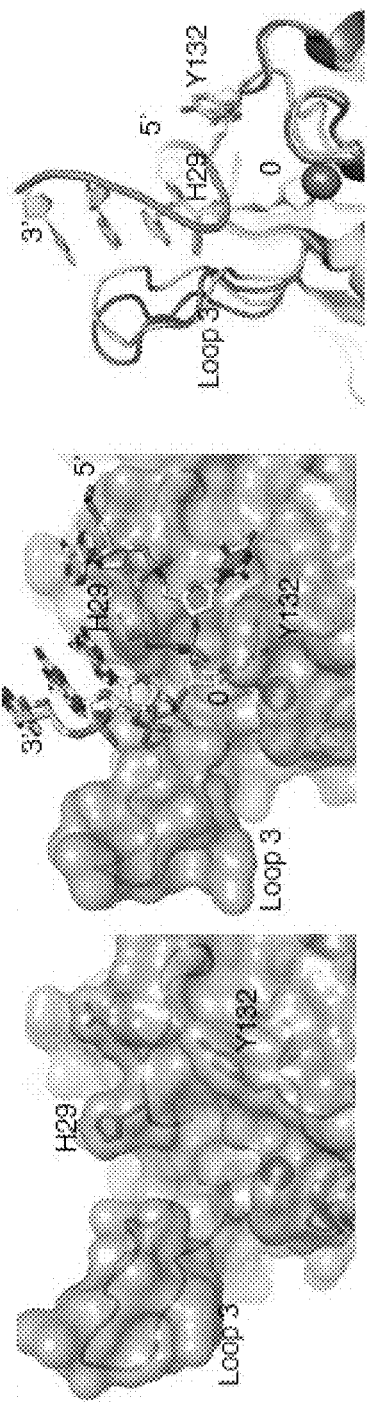
FIGS. 9A-9E are a comparison between apo and ssDNA-bound A3A and A3B structures.

Importantly, the positioning of a conserved tyrosine in loop 7, Tyr132 and Tyr315, changes upon binding ssDNA in both the A3A and A3Bctd* structures (FIGS. 9A-9C and 9D-9E for bound and unbound comparisons of A3A and A3B, respectively). For both enzymes, this reorientation is important to confer dinucleotide target specificity through extensive van der Waals contacts with the −1 thymine (above). Indeed, loop 7 swap experiments have shown that the residues including A3A Tyr132 are critical for determining the preference of the −1 nucleobase (Rathore et al., supra). For example, the 5'-CC dinucleotide specificity of A3G skewed toward 5'-TC upon swapping the entirety of loop 7 or by changing Asp317 to a tyrosine in order to mimic this residue in A3A and A3B. It also is notable that the Tyr315 reorientation converts a closed active site conformation of A3Bctd to the more open conformation required for binding ssDNA (FIGS. 9D and 9E). The comparison between the apo and ssDNA-bound A3A structures also shows that loop 3, which is variable among APOBEC3 family members, swings toward the ssDNA and makes a backbone contact (FIG. 9C). However, both the apo and bound A3A structures have relatively open conformations, possibly accounting for the higher catalytic activity of this enzyme in comparison to A3B (Caval et al. 2015, supra; and Fu et al., supra).

Example 7—Biochemical Analyses Corroborate the ssDNA-Bound A3A and A3Bctd* Structures The overall 'U-shaped' ssDNA conformation and the positioning of the 5'-TC target dinucleotide are nearly identical between the two independent crystal structures (FIG. 5B). This superposition strongly implies that the observed ssDNA binding and local targeting mechanisms are accurate reflections of the biological and pathological activities of these enzymes in virus and cancer mutagenesis. To further validate these structural results, wild-type A3A and structure-informed mutant derivatives were compared in a series of biochemical experiments with extracts from 293T cells. Active site alanine mutants were inactive in deaminating a 5'-TC-containing ssDNA substrate, as expected, including those with substitutions of the catalytic glutamate (E72A), the zinc-coordinating histidine and cysteines (H70A, C101A, and C106A), and the tryptophan lining a side of the active site pocket (W98A) (upper panel in FIG. 10A). The conserved cytosine-contacting residues, Ala71 (A71G, A71P), Ser99 (S99A, S99G, S99P), and Tyr130 (Y130A) also proved essential. The interaction between Thr31 and the 2'-deoxyribose of the target cytosine was only mildly compromised by an alanine substitution (T31A) and fully disrupted by the introduction of a negative charge (T31D), consistent with prior data indicating proximity of this residue to ssDNA (Demorest et al., *J Biol Chem* 286:26568-26575, 2011). All constructs expressed similarly in immunoblots, indicating that the activity data were not due to poor expression or misfolding (lower panels in FIG. 10A).

Figure 10B:
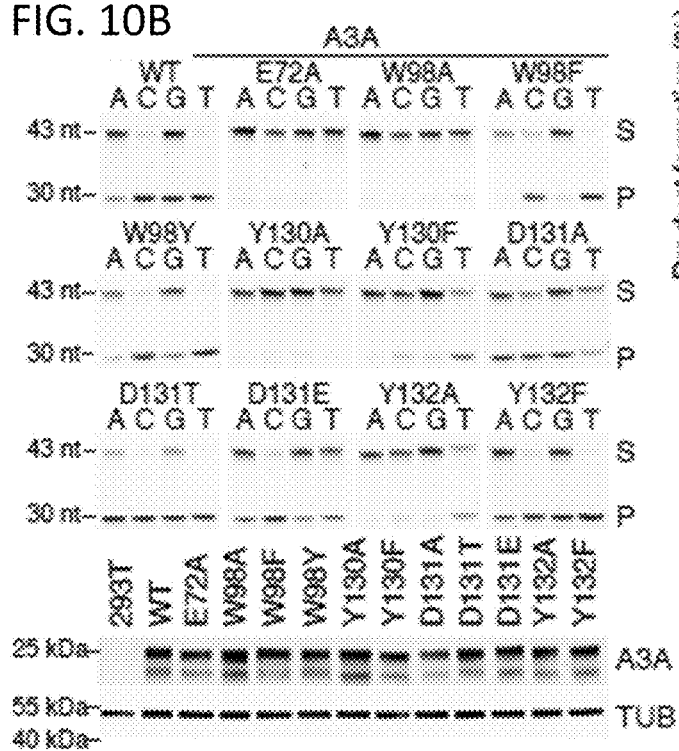
Figure 10C:
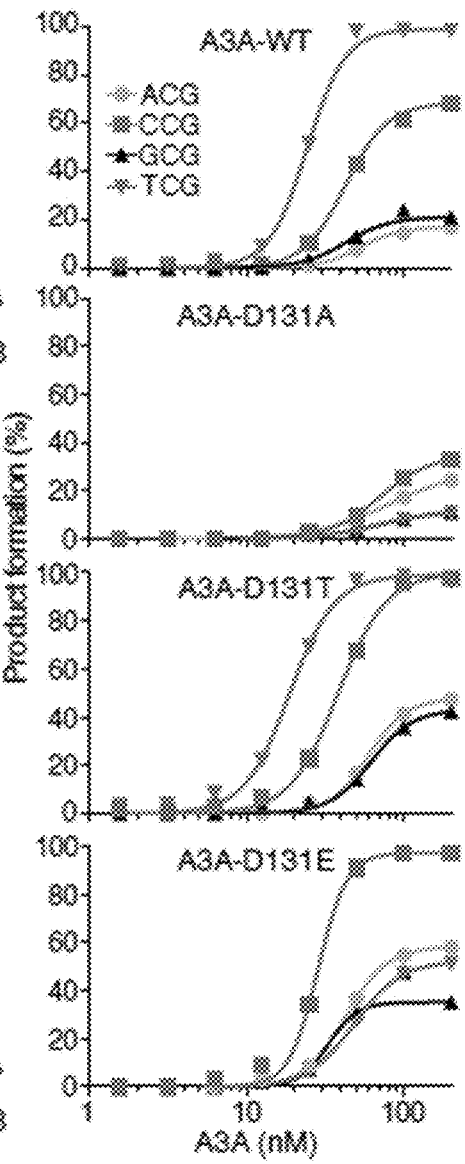

Additional ssDNA deamination experiments were conducted to interrogate A3A contacts with the specificity-conferring −1 thymine nucleobase (upper panel in FIG. 10B). These experiments were performed as described above, except both activity and selectivity were examined in parallel by systematically varying the −1 position of the ssDNA substrate. As controls, wild-type A3A has the most activity with ssDNA substrates with −1 T, intermediate activity with −1 C, and little activity with −1 A or G, whereas A3A-E72A has no activity. A comparison of Trp98 substitutions indicated that an aromatic residue is sufficient at this position in the structure to stabilize −1 T and the target C, as the W98A mutant was inactive but W98F and W98Y substitution mutants retained robust catalytic activity and near wild-type dinucleotide preferences. The aromatic character of Tyr132 is similarly important in forming the hydrophobic pocket for −1 T, based on near wild-type activity for Y132F but not Y132A constructs. Parallel, albeit more severe, effects of phenylalanine and alanine substitutions for Tyr130 were observed. The overall greater importance of an aromatic side chain at position 130 was further indicated by contacts with the target C and the ssDNA backbone as well as van der Waals interactions with Tyr132, which help to position the −1 T (FIGS. 4C and 4D). As alluded above, Asp131 strongly influences the −1 preference, with a small non-polar alanine substitution (D131A) loosening selectivity and showing near-equivalent activity with −1 T and −1 C substrates, a shorter hydroxylated residue (D131T) retaining selectivity for −1 T (likely by mimicking the hydrogen bond acceptor role of the aspartate), and a longer and acidic glutamate substitution (D131E) converting the preference at −1 position to C (most likely by creating an opportunity for direct hydrogen-bonding with the amino group of the cytosine ring and simultaneously disrupting the hydrogen-bonding between carboxyl group of the shorter aspartate side chain and the N3 hydrogen of thymine; FIG. 11). As above, the mutants expressed similarly in immunoblots with few exceptions, indicating that the activity data were not due to poor expression or misfolding (lower panels in FIG. 10B). The D131 results were confirmed in quantitative dose response experiments with purified A3A and single amino acid substitution derivatives (FIG. 10C). Overall, these biochemical data strongly support the observed conformation of 5'-TC-containing ssDNA bound to A3A in the crystal structure.

Figure 13A:
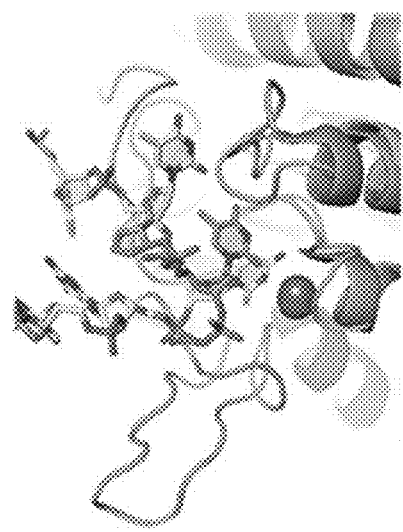
FIGS. 13A and 13B are a comparison of A3A-ssDNA and A3Gntd-poly dT structures.
Figure 13B:
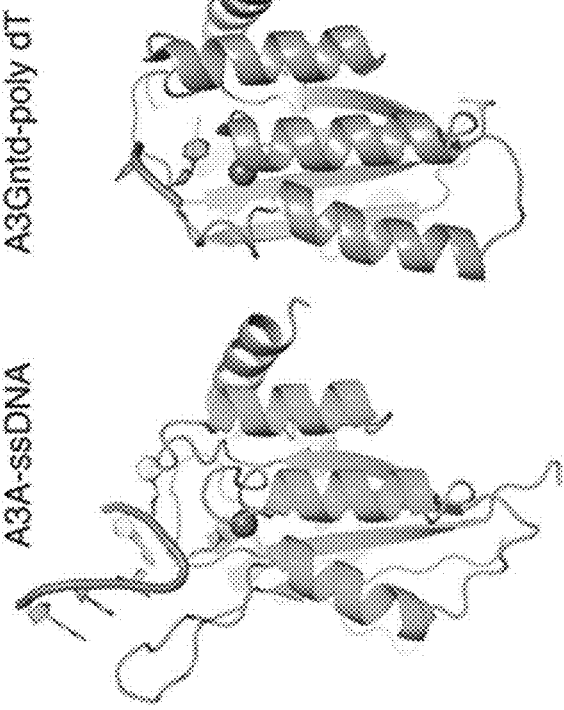
Figure 16A:
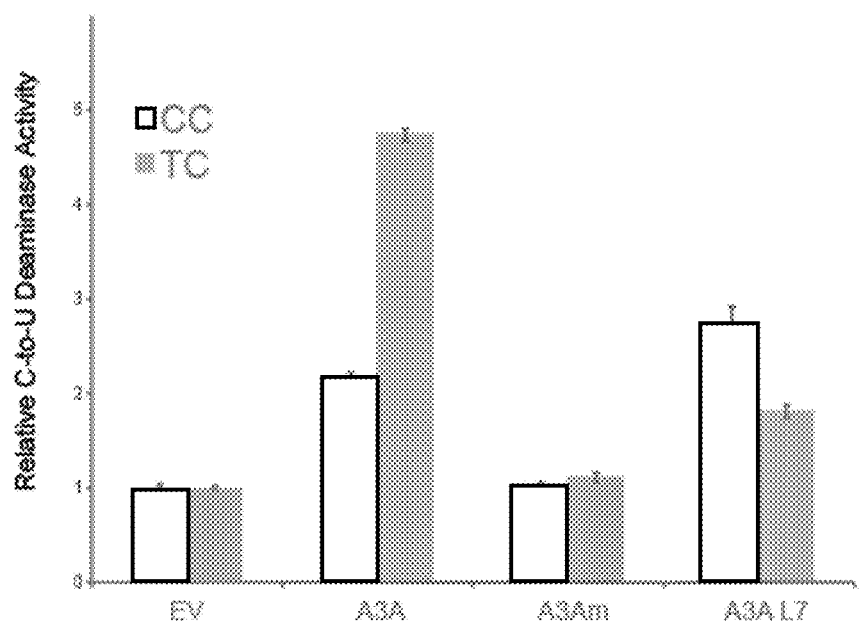
FIGS. 16A-16D show that the local 5'-TC preference of A3A can be changed to 5'-CC by replacing loop 7 amino acids with the corresponding loop 7 residues from A3G.
Figure 16B:
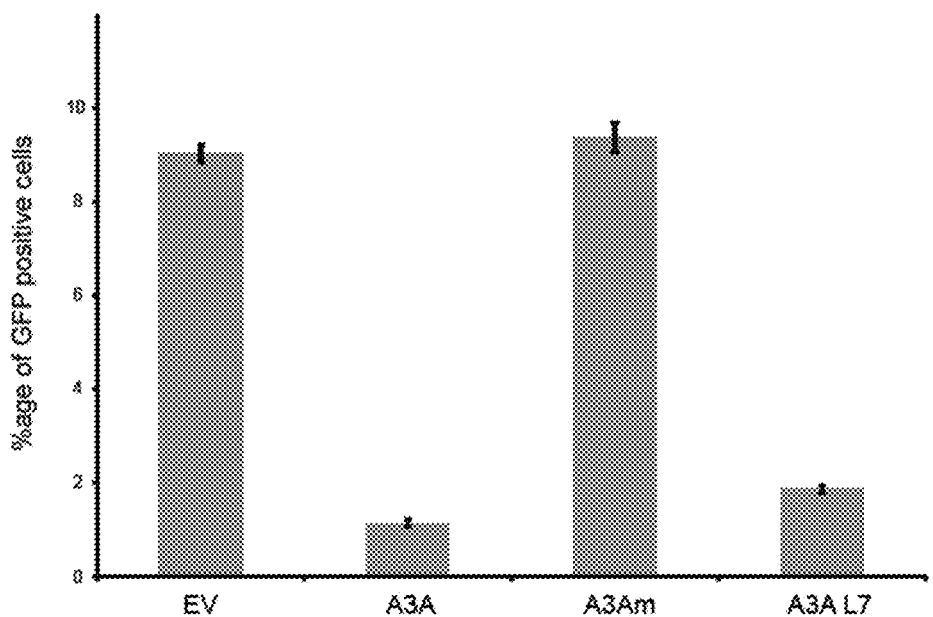
Figure 16C:
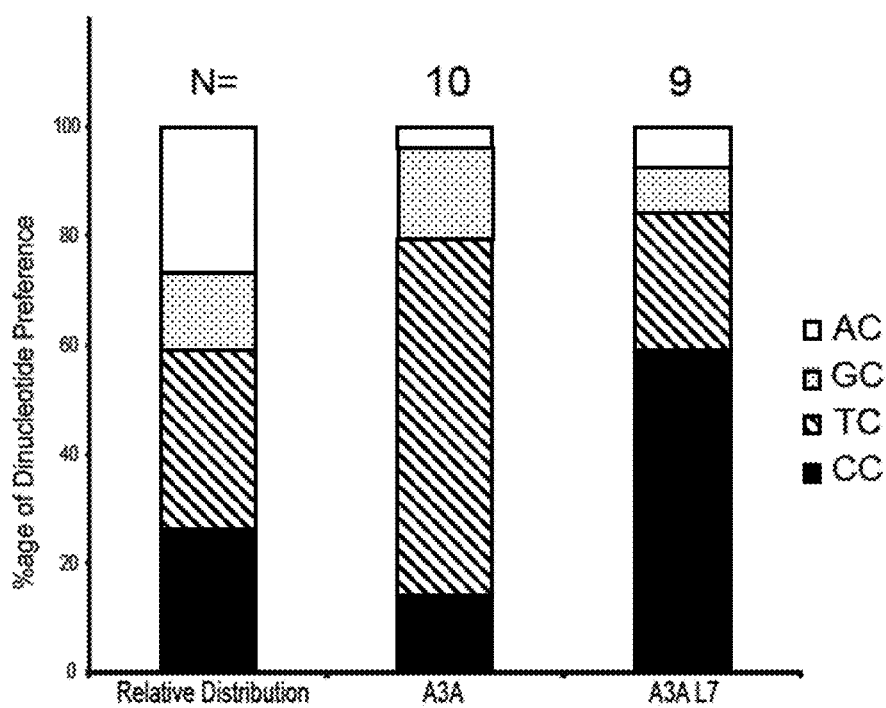
Figure 16D:
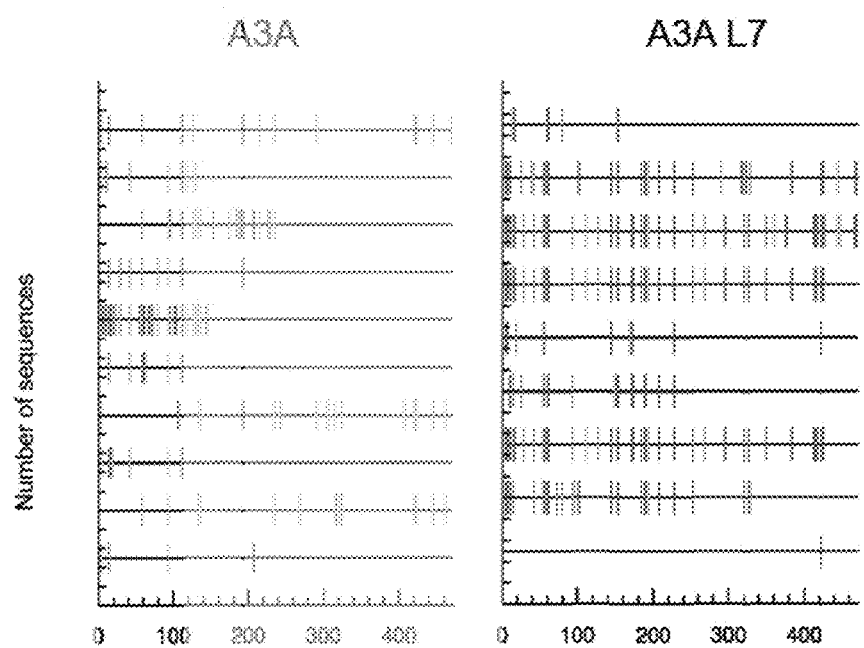

The 'U-shaped' ssDNA-binding mechanism, as revealed by co-crystal structures and validated through biochemical analyses, suggested that the loop regions of DNA stem-loop structures may be hotspots for APOBEC mutagenesis. Indeed, loop regions in HIV-1 cDNA have been shown to be preferred sites for A3G-mediated DNA deamination (Holtz et al., *Nucleic Acids Res* 41:6139-6148, 2013), and multiple hotspots for APOBEC signature mutations have been reported within loop regions of predicted stem-loop structures in breast cancer genomes (Nik-Zainal et al., *Nature* 534:47-54, 2016). The "U-shaped" ssDNA binding conformation of A3A and A3Bctd* resembles the conformation of RNA bound to the distantly related tRNA adenosine deaminase TadA (FIG. 12). Additional structural studies may determine whether the common ssDNA-binding mechanism observed here for A3A and A3Bctd* represents that of wild-type A3B with natural loop 1 residues or that of other APOBEC3 family members including A3G. Nonetheless, the similarity between these nucleic acid binding conformations suggested that hairpin or hairpin-like ssDNA or RNA structures may be preferred substrates for many different polynucleotide deaminase family members. However, the vast majority of viral and genomic ssDNA APOBEC mutations are not found in predicted secondary structures and, instead, correlate with properties of DNA replication (single-stranded cDNA in retroviral reverse transcription and lagging-strand DNA in tumor cells), indicating that the most critical feature may be simply single-strandedness (Helleday et al., supra; Roberts and Gordenin, supra; and Swanton et al., supra). The mechanism of binding ssDNA by human A3A and A3Bctd* contrasts with prior models (see, e.g., Chen et al., *Nature* 452:116-119, 2008; Holden et al., *Nature* 456:121-124, 2008; Byeon et al. 2013, supra; Shi et al., supra; and Byeon et al. 2016, supra), the conformation of a short oligo-dT co-crystalized with A3Gntd (Xiao et al., *Nat Commun* 7:12193, 2016; and FIG. 13), and the mechanism of double-stranded RNA binding and adenosine deamination by ADAR2 (Matthews et al., *Nat Struct Mol Biol* 23:426-433, 2016).

Residues within the A3A and A3B active site pockets are highly conserved within the APOBEC3 family, as evidenced by a close superpositioning of the active site region of crystal structures of several human APOBEC3 enzymes (A3A, A3B, A3C, A3F, and A3G) (FIG. 14). The only minor exception is Thr31 of A3A (Thr214 in A3B), which is a Ser216 in A3F. The T31A substitution of A3A is well tolerated but T31D abolishes deaminase activity, consistent with a potential for phospho-regulation at this position (FIG. 10A, Demorest et al., supra; and Shirakawa et al., *Nat Struct Mol Biol* 15:1184-1191, 2008). The corresponding residue in more distantly related metabolic cytosine deaminases, which likely catalyze the same hydrolytic chemistry of the cytosine deamination reaction as APOBEC3 enzymes, is either valine or isoleucine and makes van der Waals contact with the target cytosine (FIG. 15). These enzymes also show interesting variations of the residues surrounding the target cytosine base, reflecting substrate-specific interactions. For instance, the aromatic residue stacked over the target cytosine corresponding to Tyr130 of A3A (Tyr313 of A3B) is tyrosine in the 2'-deoxycytidine-5'-monophosphate deaminase of bacteriophage T4, whereas it is phenylalanine in the nucleoside cytidine deaminase and the free cytosine deaminase, consistent with the lack of a 5'-phosphate group.

In contrast to the strict conservation of the catalytic residues in the APOBEC3 active sites, comparisons of the amino acid sequences and conformations of the loops 1, 3, and 7 suggested that adjacent contacts with ssDNA substrates are either conserved or diverged among APOBEC3 family members (Conticello, supra; Harris and Dudley, supra; and FIG. 14). The conservation accounts for the strong preference of the APOBEC3 enzymes for ssDNA, and the divergence provides flexibility to evolve varying catalytic efficiencies and local sequence preferences in order to achieve overlapping but distinct functions in innate immunity. For instance, the closed active site conformation of A3Bctd in the ground state (Shi et al., supra), in spite of the similar modes of ssDNA interaction between A3A and A3Bctd*, likely reflects a need for a tight regulation of this enzyme's activity in the nucleus. Given the roles of the APOBEC3 enzymes in virus and tumor evolution, the A3A-ssDNA and A3Bctd*-ssDNA crystal structures provide a foundation for rational design of small molecule inhibitors to impede virus and tumor evolvability.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising:
   (a) a first portion comprising an apolipoprotein B mRNA-editing complex (APOBEC) polypeptide that has deaminase activity, wherein the APOBEC polypeptide comprises an amino acid sequence that lacks amino acids 1-12 of SEQ ID NO:20 and is at least 95% identical to amino acids 13 to 199 of SEQ ID NO:20, an amino acid sequence that lacks amino acids 196-199 of SEQ ID NO:20 and is at least 95% identical to amino acids 1 to 195 of SEQ ID NO:20, or an amino acid sequence that lacks amino acids 1-12 and 196-199 of SEQ ID NO:20 and is at least 95% identical to amino acids 13 to 195 of SEQ ID NO:20; and
   (b) a second portion comprising a Cas9 polypeptide having the ability to complex with a Clustered Regularly Interspersed Short Palindromic Repeats (CRISPR) RNA (crRNA), but lacking nuclease activity.

2. The polypeptide of claim 1, wherein the APOBEC polypeptide is fused to the N-terminus of the Cas9 polypeptide or to the C-terminus of the Cas9 polypeptide.

3. The polypeptide of claim 1, wherein the APOBEC polypeptide is coupled to the Cas9 polypeptide via a linker.

4. The polypeptide of claim 1, wherein the fusion polypeptide comprises a third portion that comprises a functional domain from an inhibitor of uracil DNA glycosylase.

5. A polypeptide comprising:
   (a) a first portion comprising an APOBEC polypeptide that has deaminase activity, wherein the APOBEC polypeptide comprises an amino acid sequence that lacks amino acids 1-12 of SEQ ID NO:20 and is at least 95% identical to amino acids 13 to 199 of SEQ ID NO:20, an amino acid sequence that lacks amino acids 196-199 of SEQ ID NO:20 and is at least 95% identical to amino acids 1 to 195 of SEQ ID NO:20, or an amino acid sequence that lacks amino acids 1-12 and 196-199 of SEQ ID NO:20 and is at least 95% identical to amino acids 13 to 195 of SEQ ID NO:20, and wherein the amino acid sequence of the APOBEC polypeptide comprises a residue other than aspartate at the position corresponding to position 131 of SEQ ID NO:20; and (b) a second portion comprising a Cas9 polypeptide having the ability to complex with a crRNA, but lacking nuclease activity.

6. The polypeptide of claim 5, wherein the amino acid sequence of the APOBEC polypeptide comprises a glutamate or threonine residue at the position corresponding to position 131 of SEQ ID NO:20.

7. A method for targeted modification of a selected DNA sequence, comprising contacting the DNA sequence with:
(a) a fusion polypeptide that comprises
  (i) a first portion comprising an APOBEC polypeptide that has deaminase activity, wherein the APOBEC polypeptide comprises an amino acid sequence that lacks amino acids 1-12 of SEQ ID NO:20 and is at least 95% identical to amino acids 13 to 199 of SEQ ID NO:20, lacks amino acids 196-199 of SEQ ID NO:20 and is at least 95% identical to amino acids 1 to 195 of SEQ ID NO:20, or lacks amino acids 1-12 and 196-199 of SEQ ID NO:20 and is at least 95% identical to amino acids 13 to 195 of SEQ ID NO:20, and
  (ii) a second portion comprising a Cas9 polypeptide having the ability to complex with a crRNA, but lacking nuclease activity; and
(b) a nucleic acid comprising a crRNA sequence and a tracrRNA sequence targeted to the selected DNA sequence,
such that the nucleic acid complexes with the fusion polypeptide and directs the fusion polypeptide to the selected DNA sequence, wherein the method comprises contacting the DNA sequence with the fusion polypeptide and the nucleic acid in an amount effective for deamination of a deoxycytidine within the selected DNA sequence.

8. The method of claim 7, wherein the fusion polypeptide comprises a third portion that comprises a functional domain from an inhibitor of uracil DNA glycosylase.

9. The method of claim 7, wherein the amino acid sequence of the APOBEC polypeptide comprises a residue other than aspartate at the position corresponding to position 131 of SEQ ID NO:20.

10. The method of claim 9, wherein the amino acid sequence of the APOBEC polypeptide comprises a glutamate or threonine residue at the position corresponding to position 131 of SEQ ID NO:20.

11. The method of claim 7, wherein the contacting comprises introducing into the cell a nucleic acid encoding the fusion polypeptide, and wherein the method further comprises maintaining the cell under conditions in which the nucleic acid encoding the fusion polypeptide is expressed.

12. The method of claim 11, wherein the nucleic acid encoding the fusion polypeptide and the nucleic acid comprising the crRNA sequence and the tracrRNA sequence are in a single vector.

13. The method of claim 11, wherein the nucleic acid encoding the fusion polypeptide and the nucleic acid comprising the crRNA sequence and the tracrRNA sequence are in separate vectors.

14. The method of claim 7, wherein the contacting is in vitro.

15. The method of claim 7, wherein the selected DNA sequence is associated with a clinical condition, and wherein deamination of the cytidine results in a sequence that is not associated with the clinical condition.

16. The method of claim 15, wherein the contacting is in vivo in a subject identified as having the clinical condition.

\* \* \* \* \*